(12) United States Patent
Bruns et al.

(10) Patent No.: US 11,439,391 B2
(45) Date of Patent: Sep. 13, 2022

(54) SURGICAL STAPLER WITH TOGGLING DISTAL TIP

(71) Applicant: Ethicon LLC, Guaynabo, PR (US)

(72) Inventors: Jeffery D. Bruns, Cincinnati, OH (US); Nicholas Fanelli, Morrow, OH (US); Robert J. Simms, Liberty Township, OH (US); Scott A. Jenkins, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/729,553

(22) Filed: Dec. 30, 2019

(65) Prior Publication Data

US 2020/0237368 A1     Jul. 30, 2020

Related U.S. Application Data

(60) Provisional application No. 62/840,602, filed on Apr. 30, 2019, provisional application No. 62/798,651, filed on Jan. 30, 2019.

(51) Int. Cl.
*A61B 17/072*     (2006.01)
*A61B 17/068*     (2006.01)

(52) U.S. Cl.
CPC ........ *A61B 17/072* (2013.01); *A61B 17/0684* (2013.01); *A61B 2017/07264* (2013.01);
(Continued)

(58) Field of Classification Search
CPC ...... A61B 2017/07214; A61B 17/0686; A61B 17/115; A61B 17/068; A61B 17/072;
(Continued)

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

| EP | 0537453 A1 | 4/1993 |
| EP | 2599452 A1 | 6/2013 |

(Continued)

OTHER PUBLICATIONS

International Search Report and Written Opinion dated Apr. 8, 2020 for International Application No. PCT/IB2020/050700, 12 pages.

(Continued)

*Primary Examiner* — Stephen F. Gerrity
*Assistant Examiner* — Linda J Hodge
(74) *Attorney, Agent, or Firm* — Frost Brown Todd LLC

(57) ABSTRACT

A surgical instrument end effector includes a first jaw configured to receive a staple cartridge and a second jaw that includes an anvil having a plurality of staple forming pockets. The first and second jaws are operable to clamp and staple tissue positioned therebetween. A tip member is movably disposed at a distal end of the anvil and is configured to toggle relative to the anvil between a first discrete position and a second discrete position. The tip member in the first discrete position is oriented angularly toward the first jaw, and the tip member in the second discrete position is oriented angularly away from the first discrete position.

20 Claims, 59 Drawing Sheets

(52) U.S. Cl.
CPC ............... *A61B 2017/07271* (2013.01); *A61B 2017/07285* (2013.01)

(58) Field of Classification Search
CPC .......... A61B 17/0684; A61B 17/07207; A61B 2017/07264; A61B 2017/07271; A61B 2017/07285; A61B 2017/0046; A61B 2017/00738; A61B 2017/07257; A61B 2090/0817; A61B 2090/08021
USPC .......................................... 227/175.1, 181.1
See application file for complete search history.

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,644,848 B2 | 1/2010 | Swayze et al. | |
| 7,682,368 B1 | 3/2010 | Bombard et al. | |
| 7,721,930 B2 | 5/2010 | McKenna et al. | |
| 7,866,523 B1 | 1/2011 | White et al. | |
| 8,210,411 B2 | 7/2012 | Yates et al. | |
| 8,403,196 B2 * | 3/2013 | Beardsley ............ | A61B 17/068 227/175.1 |
| 8,408,439 B2 | 4/2013 | Huang et al. | |
| 8,453,914 B2 | 6/2013 | Laurent et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,913,642 B2 | 3/2018 | Leimbach et al. | |
| 9,936,952 B2 | 4/2018 | Demmy | |
| 10,092,292 B2 | 10/2018 | Boudreaux et al. | |
| D833,010 S | 11/2018 | Harris et al. | |
| D836,198 S | 12/2018 | Harris et al. | |
| D836,199 S | 12/2018 | Schowalter et al. | |
| 10,182,813 B2 | 1/2019 | Leimbach et al. | |
| 10,786,252 B2 | 9/2020 | Harris et al. | |
| 10,973,516 B2 | 4/2021 | Shelton, IV et al. | |
| 2010/0094315 A1 | 4/2010 | Beardsley et al. | |
| 2011/0106150 A1 | 5/2011 | White et al. | |
| 2012/0143218 A1 | 6/2012 | Beardsley et al. | |
| 2013/0334280 A1 | 12/2013 | Krehel et al. | |
| 2014/0166723 A1 | 6/2014 | Beardsley et al. | |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2019/0000481 A1 | 1/2019 | Harris et al. | |
| 2019/0015100 A1 | 1/2019 | Yigit et al. | |
| 2020/0015812 A1 | 1/2020 | Harris et al. | |
| 2020/0015813 A1 | 1/2020 | Harris et al. | |
| 2020/0015814 A1 | 1/2020 | Harris et al. | |
| 2020/0015815 A1 | 1/2020 | Harris et al. | |
| 2020/0015817 A1 | 1/2020 | Harris et al. | |
| 2020/0205825 A1 | 7/2020 | Vendely et al. | |
| 2020/0237369 A1 | 7/2020 | Jenkins et al. | |
| 2020/0237370 A1 | 7/2020 | Fanelli et al. | |

FOREIGN PATENT DOCUMENTS

| | | |
|---|---|---|
| EP | 2674111 A2 | 12/2013 |
| EP | 2777523 A1 | 9/2014 |
| WO | WO 2013/151888 A1 | 10/2013 |
| WO | WO 2016/094236 A1 | 6/2016 |

OTHER PUBLICATIONS

International Search Report and Written Opinion dated May 4, 2020 for International Application No. PCT/IB2020/050701, 11 pages.
International Search Report and Written Opinion dated Apr. 21, 2020 for International Application No. PCT/IB2020/050703, 11 pages.
U.S. Appl. No. 16/729,557.
U.S. Appl. No. 16/729,559.
European Search Report and Written Opinion dated Apr. 8, 2020 for Application No. EP 20154700.7, 12 pgs.
European Search Report and Written Opinion dated May 8, 2020 for Application No. EP 20154723.9, 10 pgs.
European Search Report and Written Opinion dated Apr. 21, 2020 for Application No. EP 20154720.5, 10 pgs.

\* cited by examiner

SURGICAL STAPLER WITH TOGGLING DISTAL TIP

PRIORITY

This application claims priority to U.S. Provisional Patent App. No. 62/798,651, entitled "Surgical Stapler with Adjustable Tip Angulation," filed Jan. 30, 2019, and U.S. Provisional Patent App. No. 62/840,602, entitled "Surgical Stapler with Adjustable Tip Angulation," filed Apr. 30, 2019, the disclosures of which are incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents, U.S. patent Publications, and U.S. patent applications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
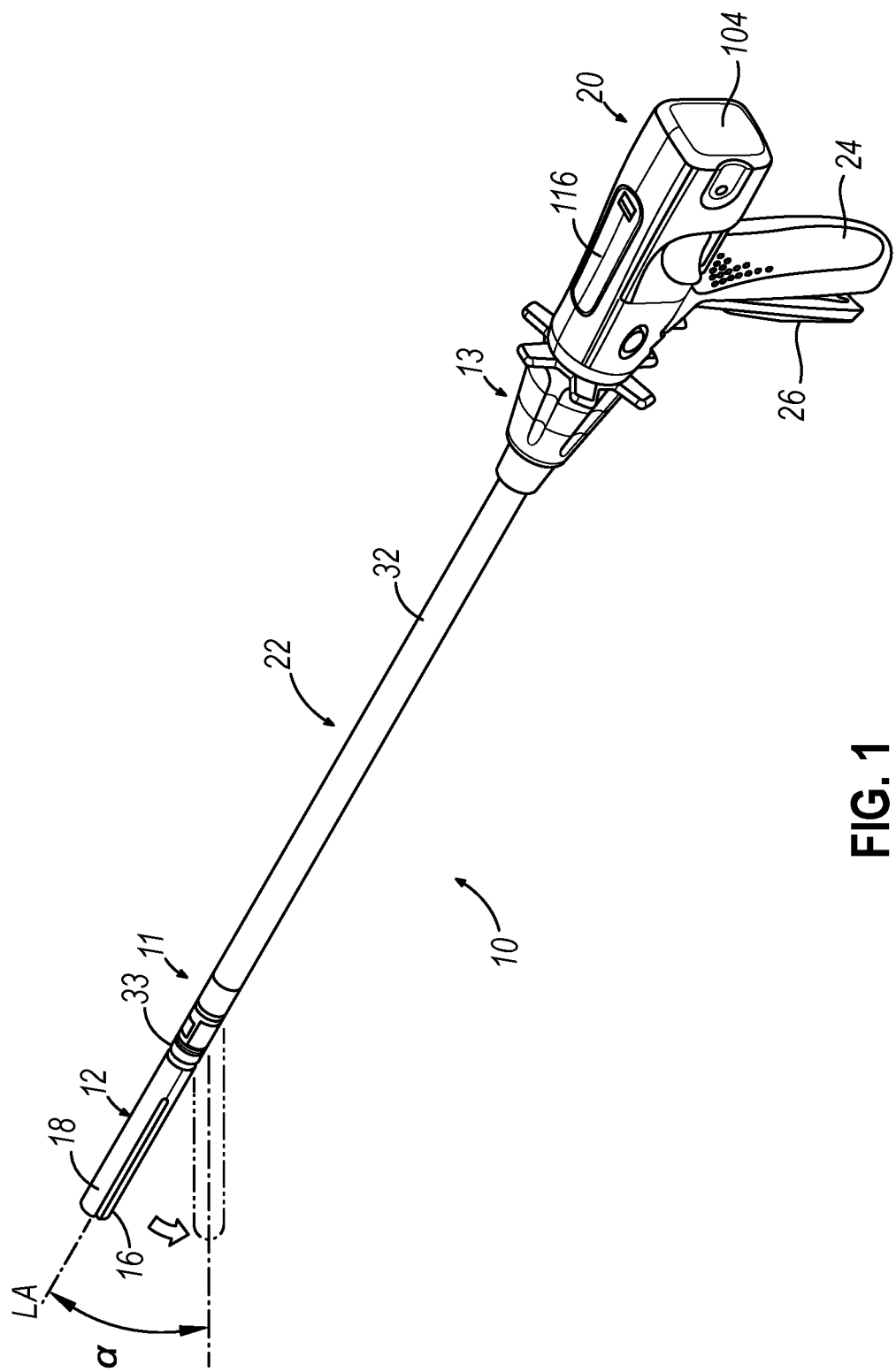
FIG. 1 depicts a perspective view of an exemplary articulating surgical stapling instrument.
Figure 2:
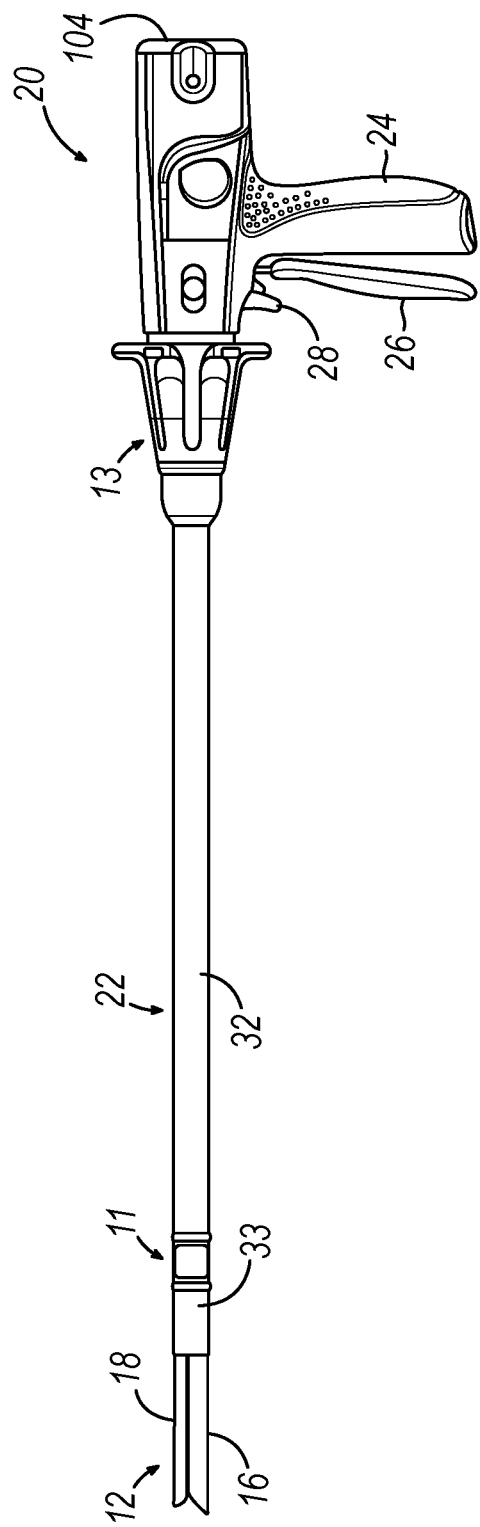
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795, 379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and an upper jaw in the form of a pivotable anvil (18). In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued on Dec. 13, 2016, the disclosure of which is incorporated by reference herein; at least some of the teachings of U.S. Pat. No. 9,839,421, entitled "Jaw Closure Feature for End Effector of Surgical Instrument," issued on Dec. 12, 2017, the disclosure of which is incorporated by reference herein; and/or at least some of the teachings of U.S. Pat. No. 10,092,292, entitled "Staple Forming Features for Surgical Stapling Instrument," issued Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
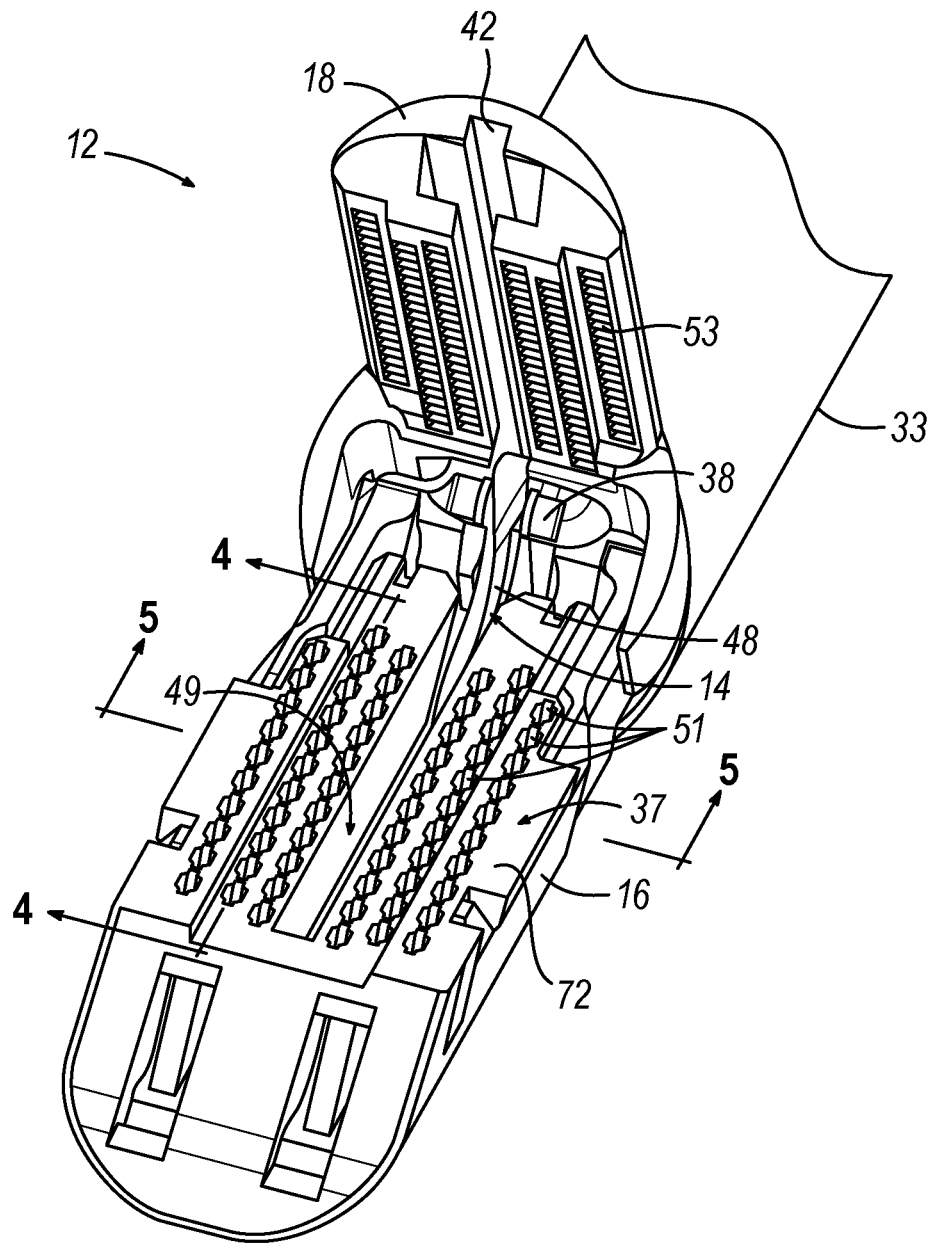
FIG. 3 depicts a perspective view of an opened end effector of the instrument of FIG. 1.
Figure 4A:
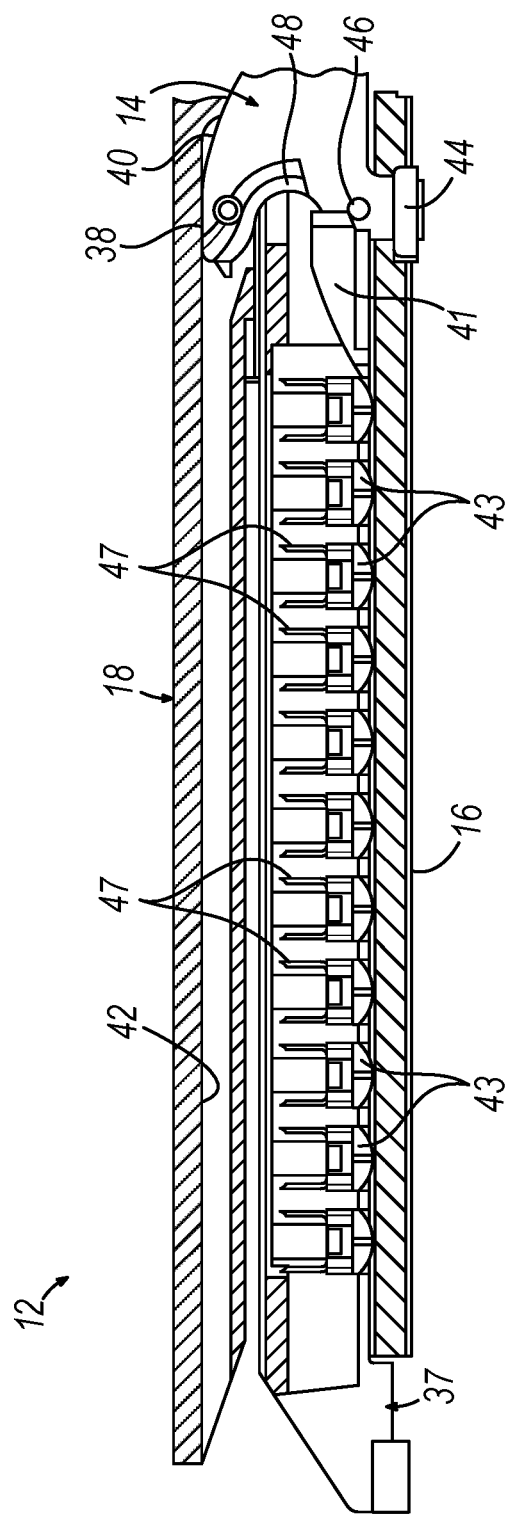
FIG. 4A depicts a side cross-sectional view of the end effector of FIG. 3, taken along line 4-4 of FIG. 3, with the firing beam in a proximal position.
Figure 4B:
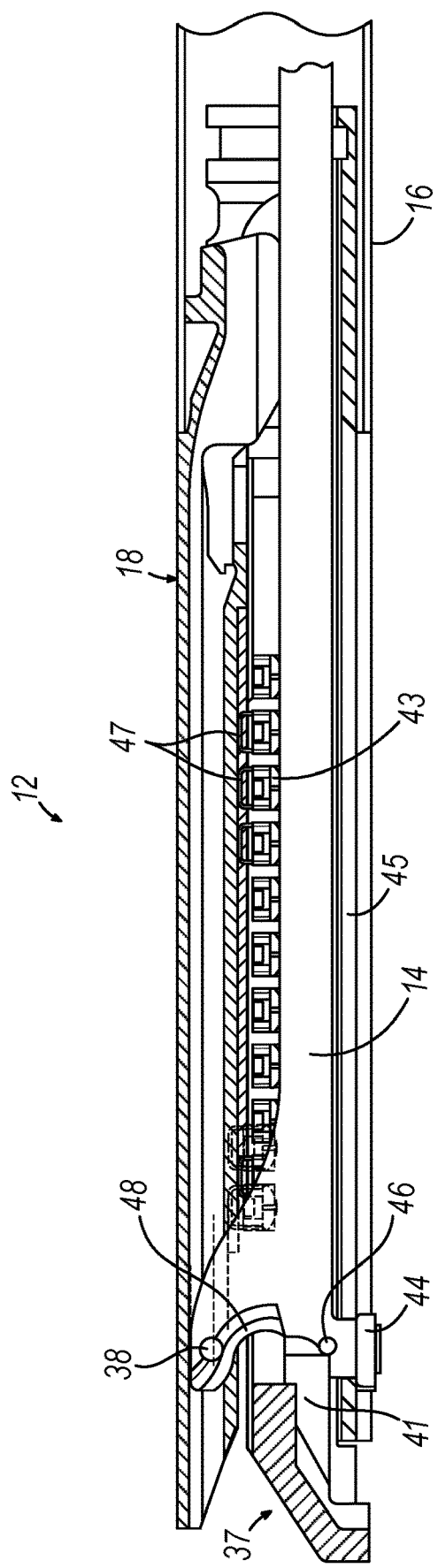
FIG. 4B depicts a side cross-sectional view of the end effector of FIG. 3, taken along line 4-4 of FIG. 3, with the firing beam in a distal position.
Figure 5:
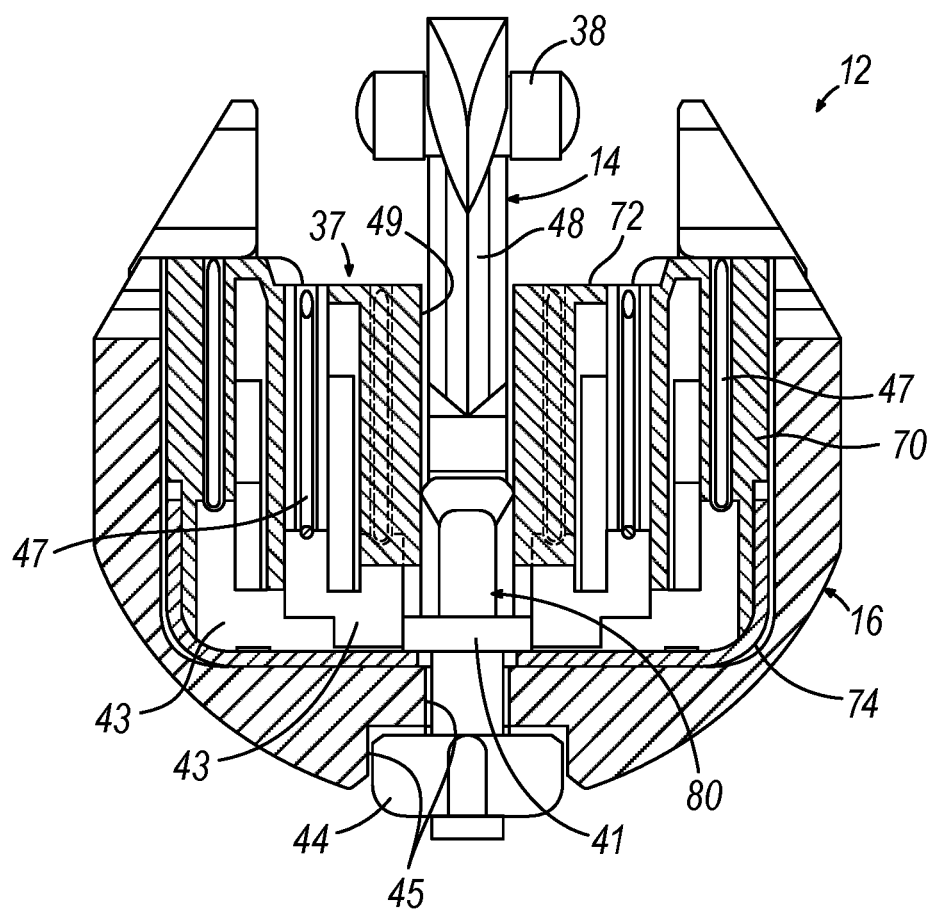
FIG. 5 depicts an end cross-sectional view of the end effector of FIG. 3, taken along line 5-5 of FIG. 3.
Figure 6:
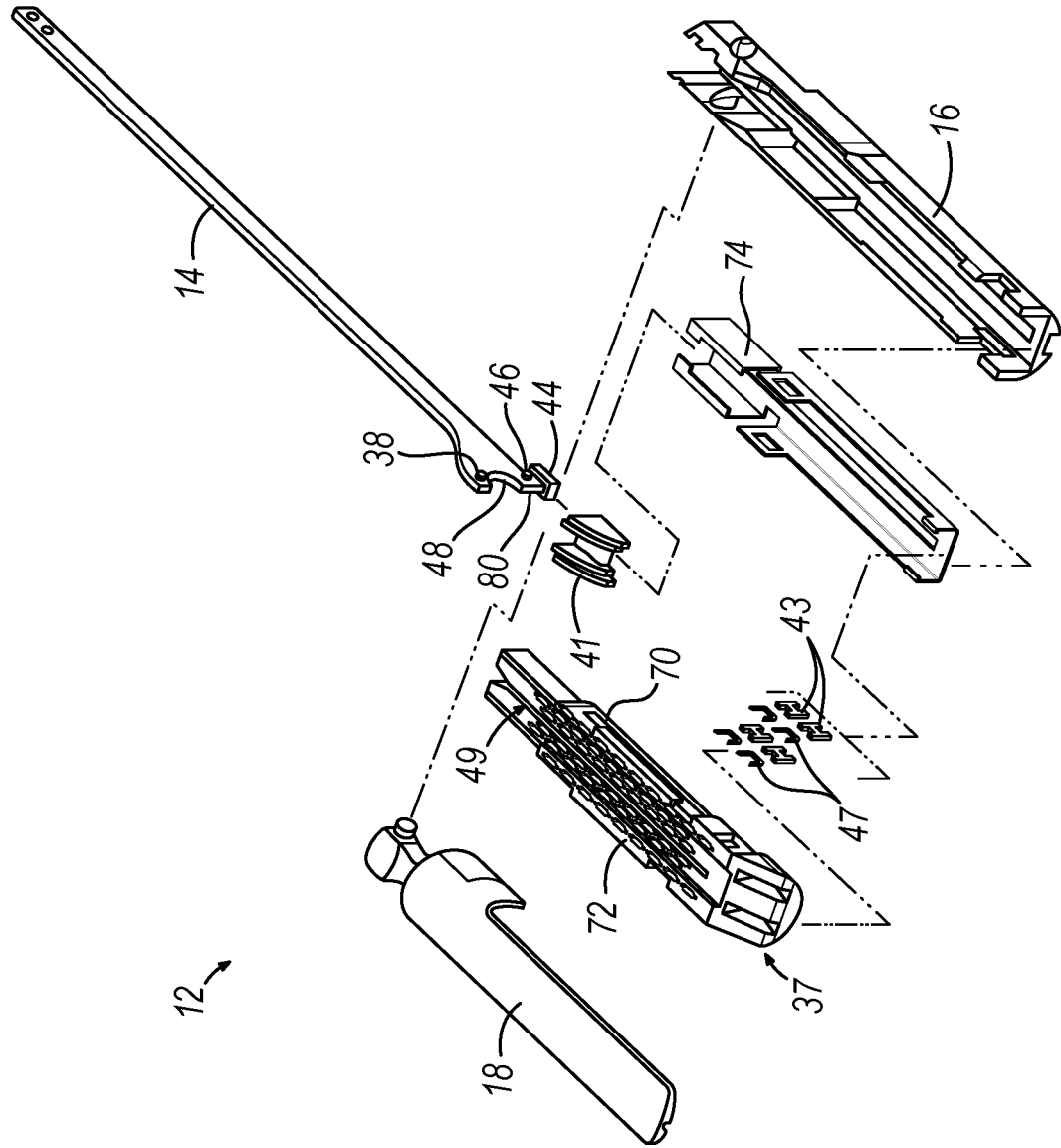
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
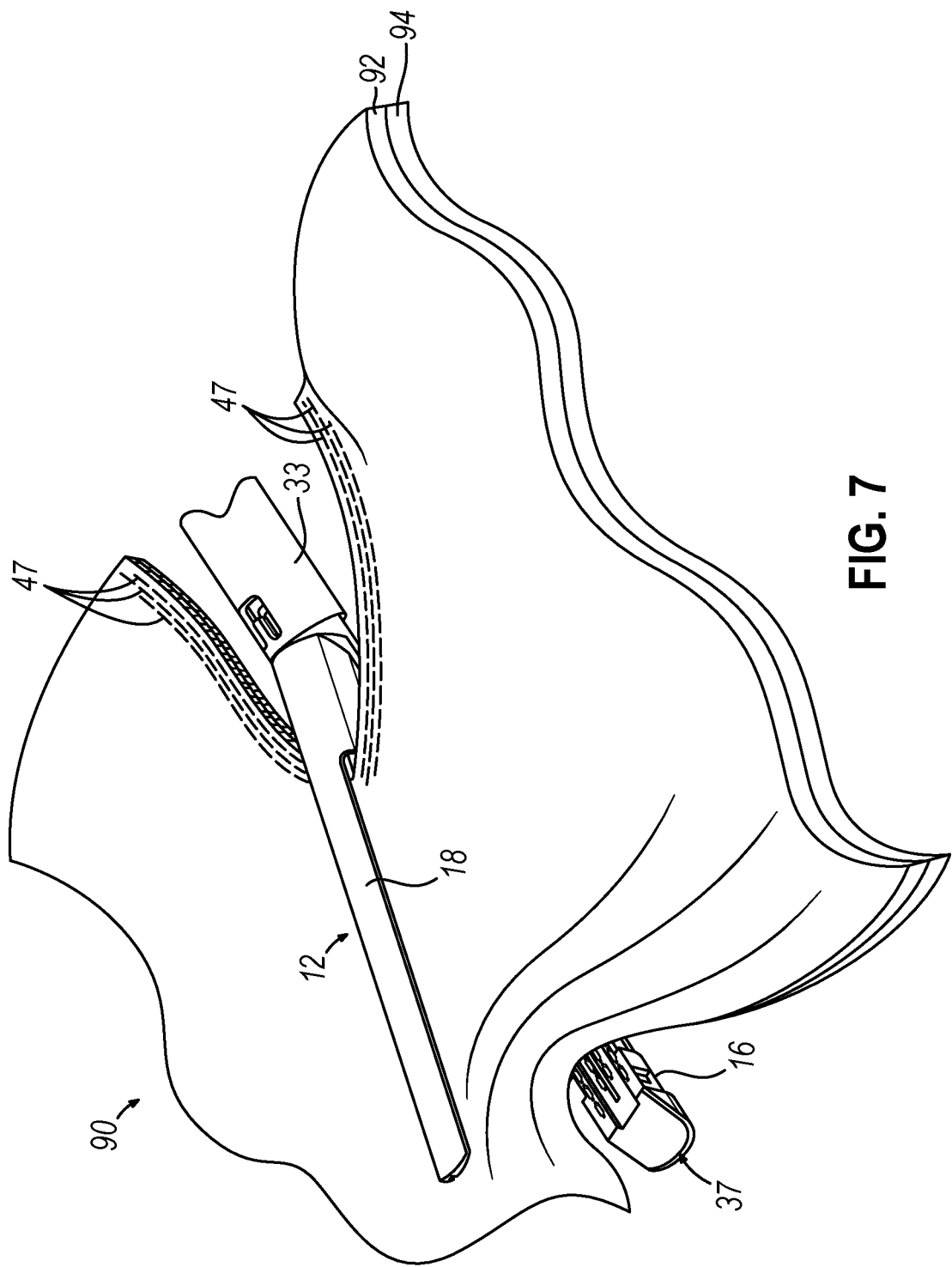
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644, 848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465, 895; 5,597,107; 5,632,432; 5,673,840; 5,704,534; 5,814, 055; 6,978,921; 7,000,818; 7,143,923; 7,303,108; 7,367, 485; 7,380,695; 7,380,696; 7,404,508; 7,434,715; 7,721, 930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-in, and Gathering Feature

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
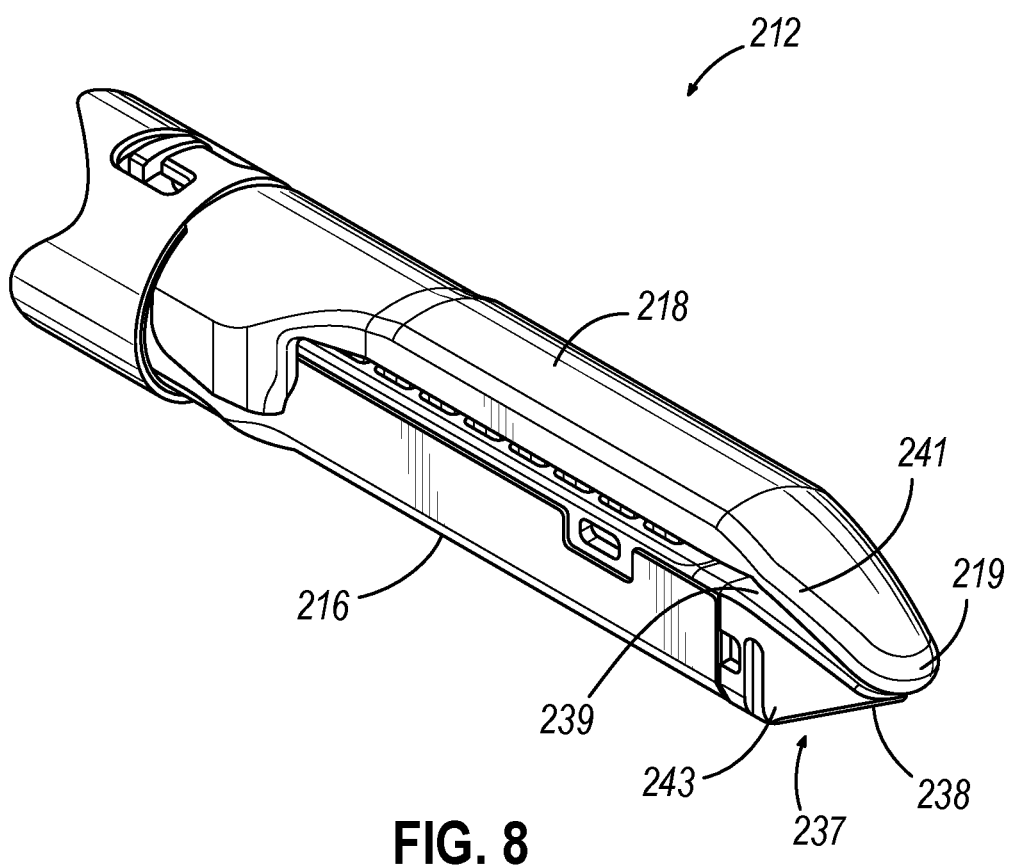
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
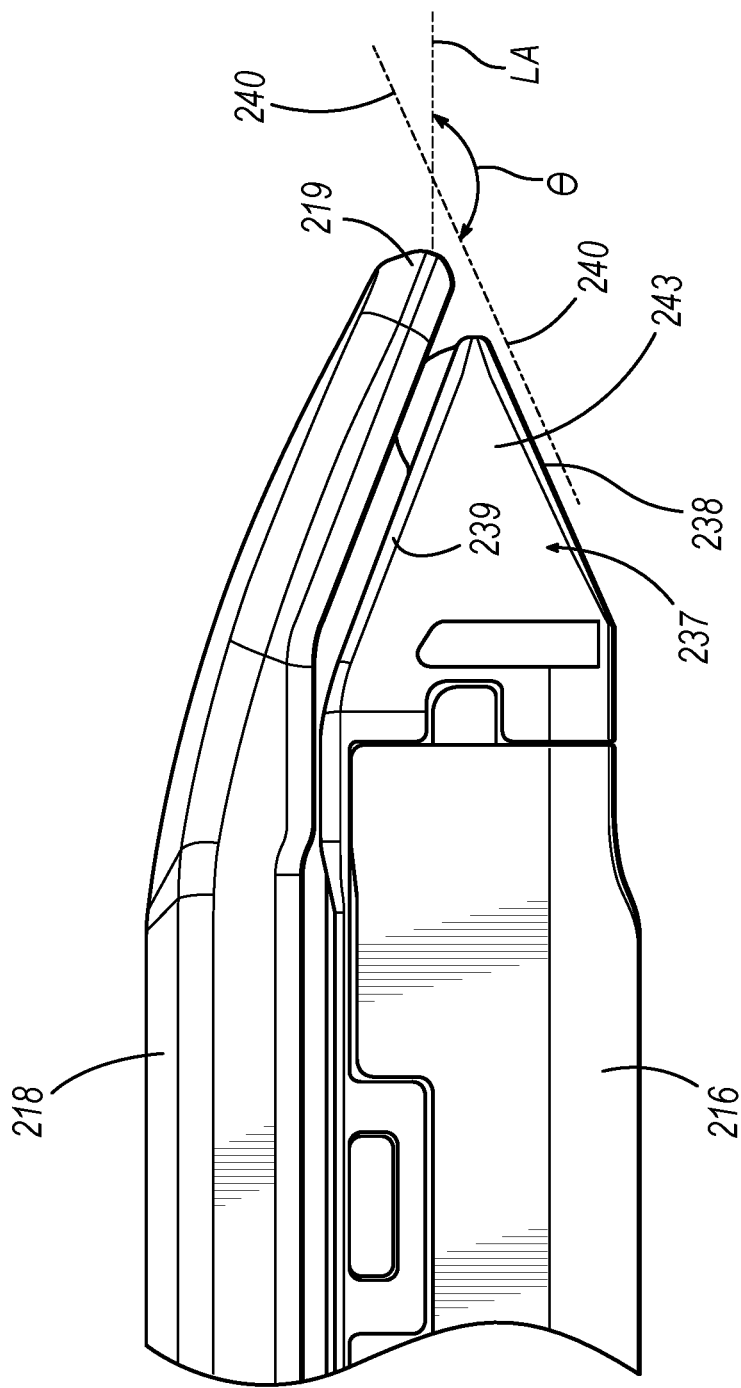
FIG. 9 depicts an enlarged, side view of the end effector of FIG. 8.
Figure 10:
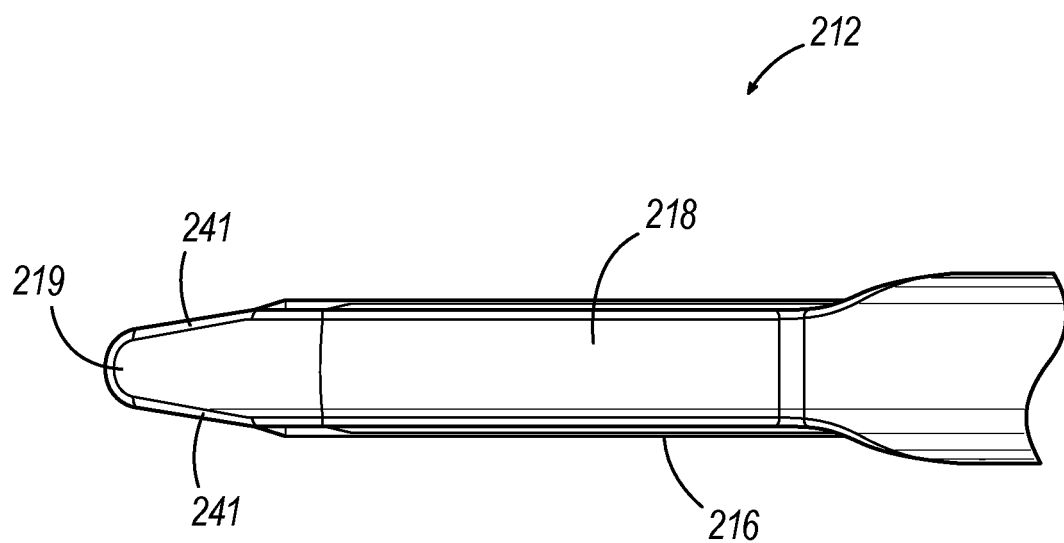
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. End Effectors with Angled Elastically Deformable Anvil Tips

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
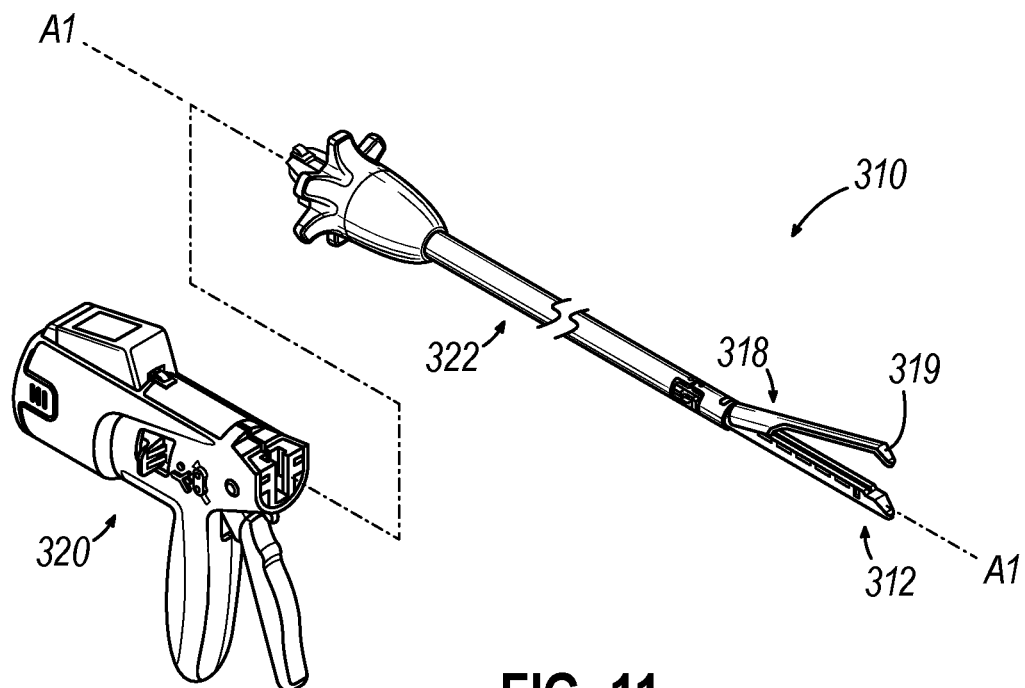
FIG. 11 depicts a perspective view of an exemplary surgical stapling instrument having an end effector with a curved elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
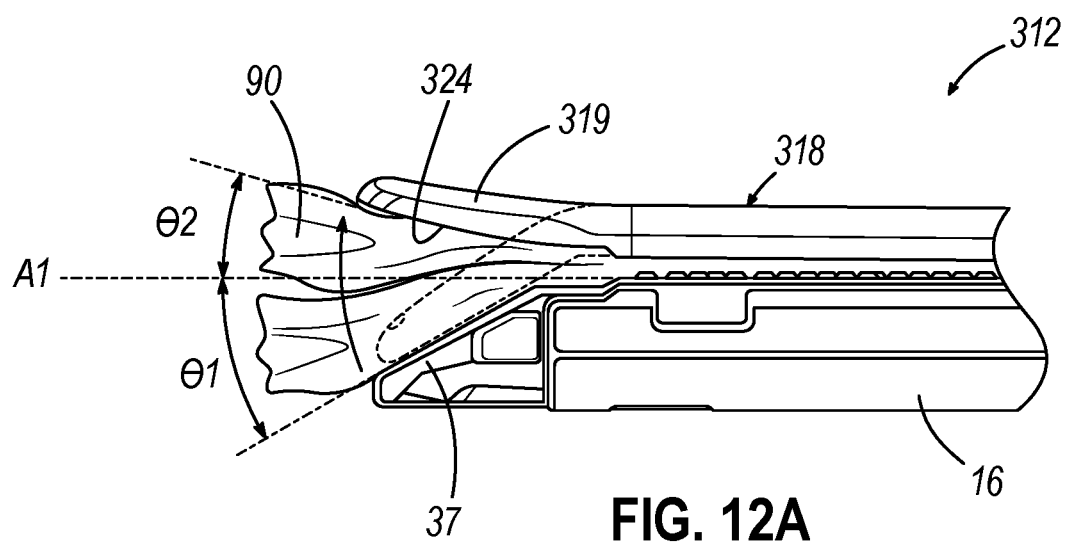
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle (θ1). When closed and clamping tissue (90) between anvil (318) and lower jaw (16), underside surface (324) of tip (319) contacts tissue (90). In this position, underside surface (324) of tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles (θ1, θ2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
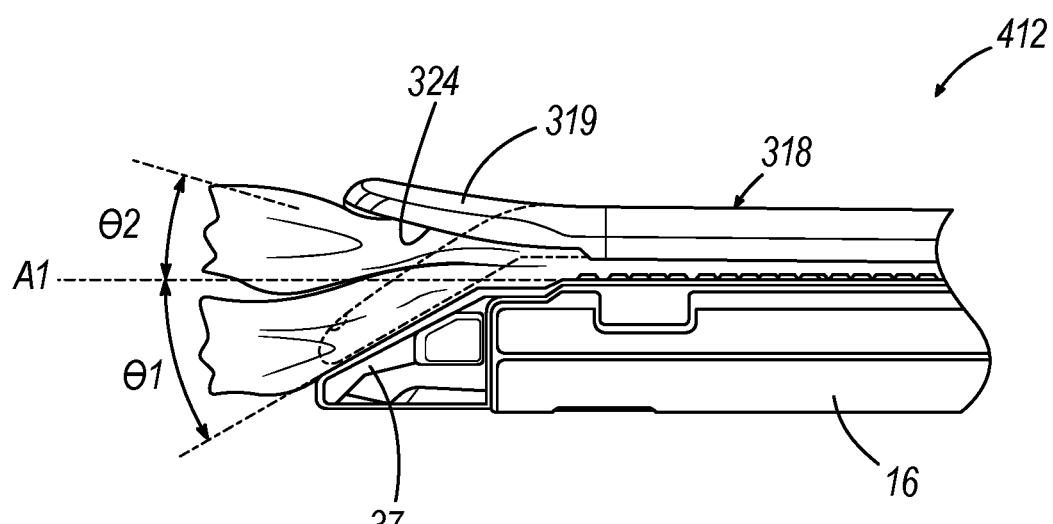
FIG. 12B depicts an enlarged side view of a distal portion of an alternate end effector similar to that of FIG. 11.
Figure 13:
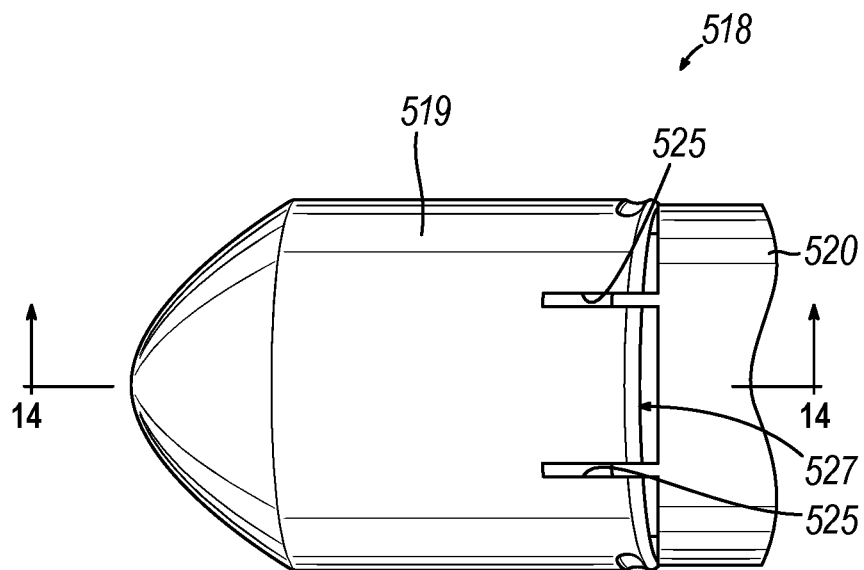
FIG. 13 depicts a partial top view of an alternate anvil of an end effector for use with the surgical instruments described herein.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

IV. Exemplary End Effectors with Discrete Position Pivoting Tips

In some instances, it may be desirable to provide the user with a versatile end effector with a tip that can take on different configurations for differing applications. For instance, it may be desirable or beneficial to a user to use an end effector with an angled (or "bent") tip for the visualization and placement benefits as described above. Furthermore, not only visualization of the distal end of the end effector may be desirable, but also it may be desirable to construct the end effector such that the distal end of the anvil is configured to urge tissue (e.g., a large vessel) proximally into the space between the anvil and the lower jaw as the anvil closes toward the lower jaw. Still, in other circumstances, it may be desirable or beneficial to a user to use an end effector with a straight or flared tip so the end effector better accommodates procedures involving marching as also discussed above. Furthermore, it may be desirable or beneficial for a user to be able to toggle a tip of the end effector out of the way when the user is concerned about the pressure on the tissue under the tip in use.

It will be appreciated that the terms "angled" and "bent" as used herein in connection with the various exemplary anvil tips disclosed encompass tip configurations in which the tip defines a flat planar exterior surface that extends angularly in a distal direction from the distal end of the anvil body; and also tip configurations in which the tip defines a curved exterior surface that extends arcuately in a distal direction from the distal end of the anvil body (e.g., where the tip is said to be in a "curved" configuration). In both such types of configurations, a distal end of the anvil tip is vertically offset from a longitudinal axis of the anvil body along an axis that extends transversely to the longitudinal axis and through the corresponding staple cartridge, such that the tip as a whole is "angled" or "bent" relative to the anvil body.

A. Exemplary End Effector Pinned Pivoting Tip with Detents

FIGS. 13-16 depict exemplary anvils (518, 118) usable with the end effectors described herein and others. For instance, anvils (518, 118) can be interchanged or used in place of anvils (18, 218, 318) of respective end effectors (12, 212, 312, 412) described above. It will be appreciated that end effectors (12, 212, 312, 412) incorporating either of anvils (518, 118) may be used with instruments (10, 310) and the other surgical instruments described herein. To this extent, end effectors (12, 212, 312, 412) incorporating either of anvils (518, 118) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvils (518, 118) are operable to pivot relative to lower jaws (16, 216). Anvils (518, 118) and lower jaws (16, 216) may clamp tissue (90) similarly to clamping performed by anvil (18) and lower jaw (16) shown in FIG. 7. Anvils (518, 118) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating either of anvils (518, 118) further comprises a cartridge (37, 237) containing staples where cartridge (37, 237) is operable to be placed in lower jaw (16, 216).

1. Single Section Pinned Pivoting Tip

Anvil (518) comprises a body (520) and a tip (519) extending distally from body (520). Proximal to tip (519), anvil (518) comprises an extension (502) on body (520). Anvil (518) further comprises a pair of spaced apart detents (504). A portion of detents (504) located on extension (502) are configured as raised portions or protrusions (510) as shown in the illustrated version. The other portion of detents (504) are located on tip (519) and are configured as recesses (523) as will be discussed further below. Anvil (518) also comprises a bore (506) that extends through the sides of body (520) of anvil (518) and bore (506) is configured to receive a pin (508). As will be discussed further below, pin (508) defines an axis of rotation about which tip (519) is rotatable.

Tip (519) comprises a bore (521) that extends through the sides of tip (519) and bore (521) is configured to also receive pin (508). In this manner, tip (519) is operable to rotate about pin (508) and thus rotate relative to a longitudinal axis (A2) of anvil (518). Bores (506, 521) have a circular shape, but in other examples have an elongated shape. In some instances an elongated shape for bores (506, 521) provides for or contributes to tip (519) assuming different discrete positions as discussed further below. As mentioned above, tip (519) comprises a pair of recesses (523) that are configured to be selectively engageable with raised portions or protrusions (510) of detents (504). At a proximal part of tip (519), tip (519) comprises a pair of slots (525) that extend longitudinally and define a resilient portion (527). In the present example, resilient portion (527) comprises recesses (523) along an underside of resilient portion (527).

Figure 14A:
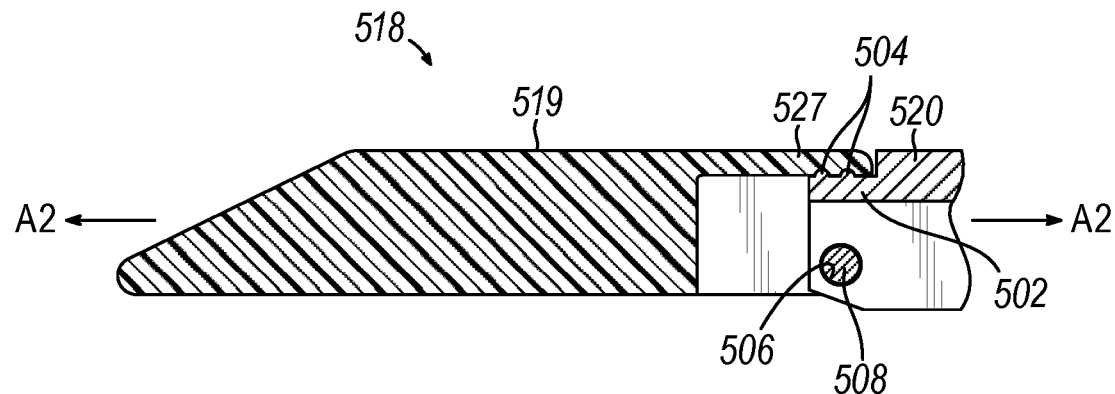
FIG. 14A depicts a cross sectional side view of the anvil of FIG. 13, taken along line 14-14 of FIG. 13, and showing a tip of the anvil in a first position.
Figure 14B:
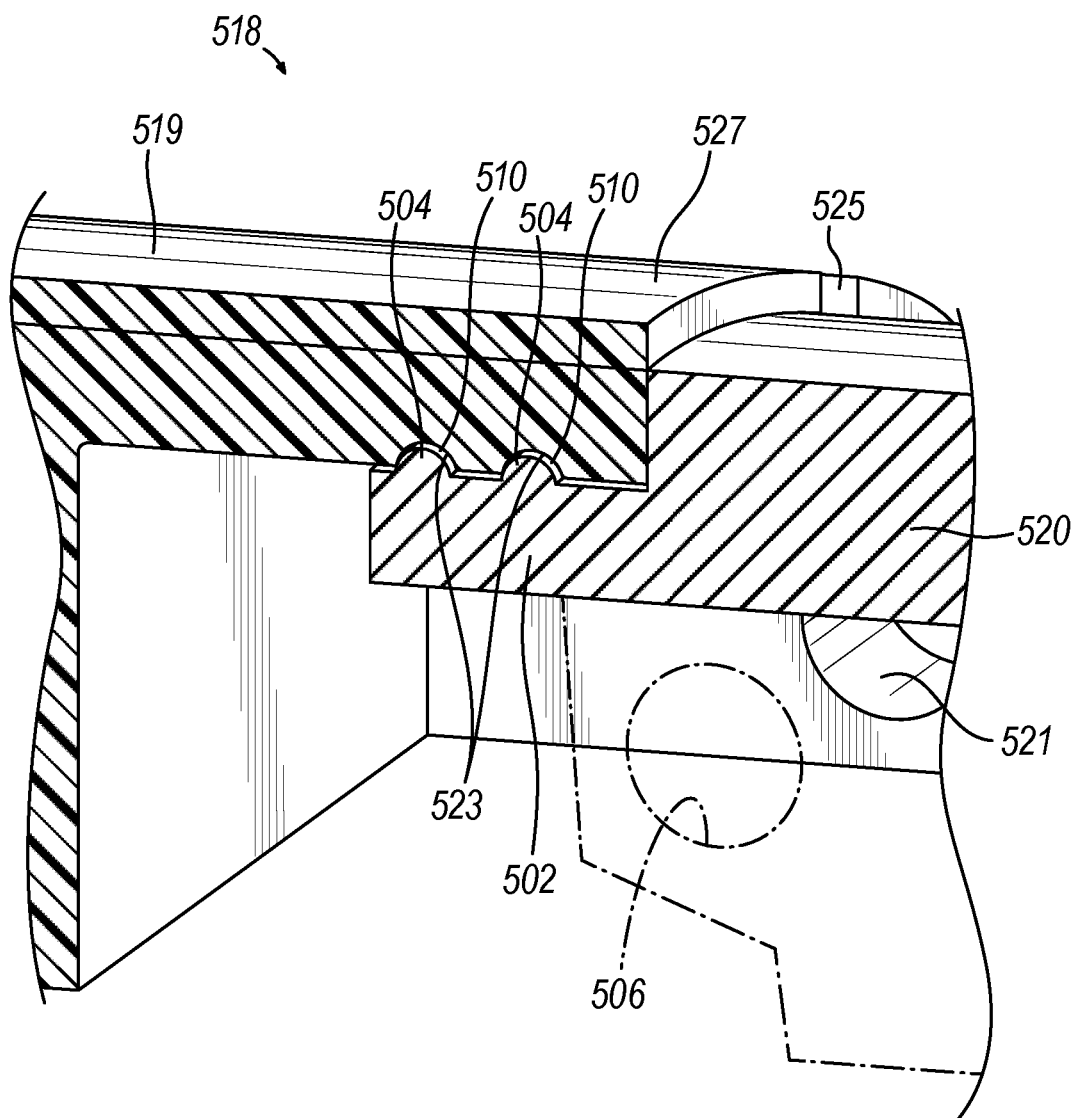
FIG. 14B depicts an enlarged perspective view of the anvil of FIG. 14A, shown with a portion of the anvil in phantom.
Figure 15:
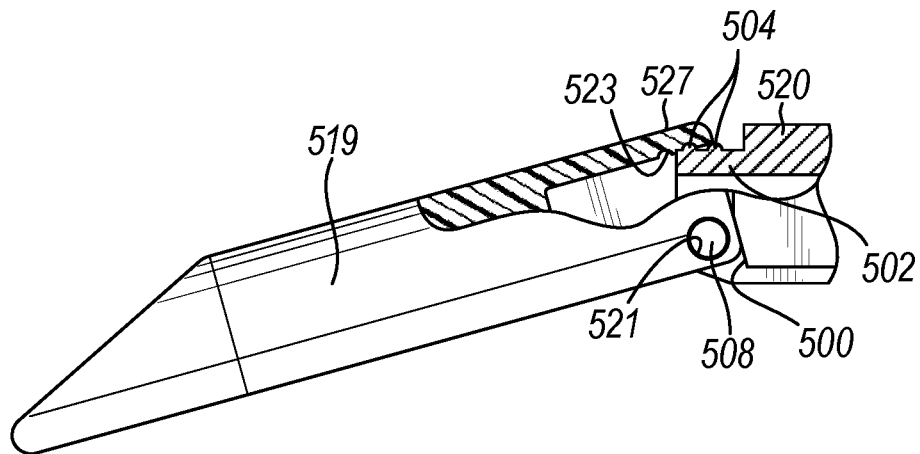
FIG. 15 depicts a side view of the anvil of FIG. 13, showing the tip of the anvil rotated to a second position.

Referring now to FIG. 14A and FIG. 15, anvil (518) is configured with tip (519) that can be moved into discrete positions. Detents (504) provide for selective engagement between raised portions (510) of detents (504) and recesses (523) of detents (504), which allow for tip (519) to move to different discrete positions. FIG. 14A illustrates tip (519) is a first position that has tip (519) in a straight orientation such that a longitudinal axis of tip (519) is generally parallel with or coincides with longitudinal axis (A2) of anvil (518). FIG. 15 illustrates tip (519) in a second position that has tip (519) in an angled orientation such that the longitudinal axis of tip (519) forms an angle with longitudinal axis (A2) of anvil (518) that is less than about 180 degrees.

As described above and illustrated in FIGS. 13-15, slots (525) define resilient portion (527), such that resilient portion (527) acts as a spring to thereby allow tip (519) to change positions by recesses (523) engaging raised portions (510) in different manners. For instance, when in the straight orientation as shown in FIG. 14A, the proximal most recess (523) engages with the proximal most raised portion (510). Similarly, in this straight orientation the distal most recess (523) engages with the distal most raised portion (510). When in the angled orientation as shown in FIG. 15, the proximal most recess (523) engages with the distal most raised portion (510). Furthermore, in this angled orientation the distal most recess (523) is not engaged with either raised portion (510). However, anvil (518) comprises a stop feature (500) that is configured to contact a proximal end of tip (519) and prevent tip (519) from moving to an even further angled position. With the engagement between one or more recesses (523) and one or more raised portions (510) in each of the straight orientations, tip (519) is adjustable or positionable in discrete positions rather than having a continuum of orientations. Thus tip (519) is configured to adopt discrete positions where tip (519) remains in one of the discrete positions until acted upon by a force sufficient to overcome the interference connection established between recesses (523) and raised portions (510) of detents (504).

Referring to FIG. 15, when tip (519) is rotated or pivoted to the angled orientation illustrated, a gap (529) can be present in some versions. An optional sleeve (not shown) can be added to anvil (518) to cover or extend over gap (529) to remove the possibility that gap (529) could present a pinch point for surrounding tissue. In some examples, such a sleeve could extend to reach the end of tip (519) and go as far back as the stapling line of anvil (518), although this would not be required in all versions.

In the one version of anvil (518), anvil (518) is constructed of a single material such as stainless steel, but other materials instead of stainless steel can be used in other versions. Furthermore, in some other versions, anvil (518) can be overcoated with another material to provide for visualization, sliding, or other material properties or attributes as will be apparent to those of ordinary skill in the art in view of the teachings herein.

In other examples of anvil (518), three detents (504) can be used such that three discrete positions for tip (519) can be defined. In such a version with three detents (504), tip (519) can be configured to adopt either a straight orientation, an angled orientation (which may form a curved configuration), or a flared or open orientation where tip (519) is bent upward away from lower jaw (16, 216). Also, in other examples of anvil (518), detents (504) can be located on the sides of tip (519) and body (520) of anvil (518) instead of the top. Still yet, in some other examples, the location of the features of detents (504) can be opposite. For instance, instead of raised portions (510) being located on body (520) of anvil (518), raised portions are located on tip (519). In such an example, instead of slots (525) and resilient portion (527) with recesses (523) being located on tip (519), slots (525) and resilient portion (527) with recesses (523) are located on body (520) of anvil (518). In such an example, these features still cooperate in the same manner as described above to provide for discrete positioning of tip (519). In view of the teachings herein, other ways to configure anvil (518) and detents (504) to achieve multiple discrete positions for tip (519) will be apparent to those of ordinary skill in the art.

2. Multiple Sections Pinned Pivoting Tip

Figure 16:
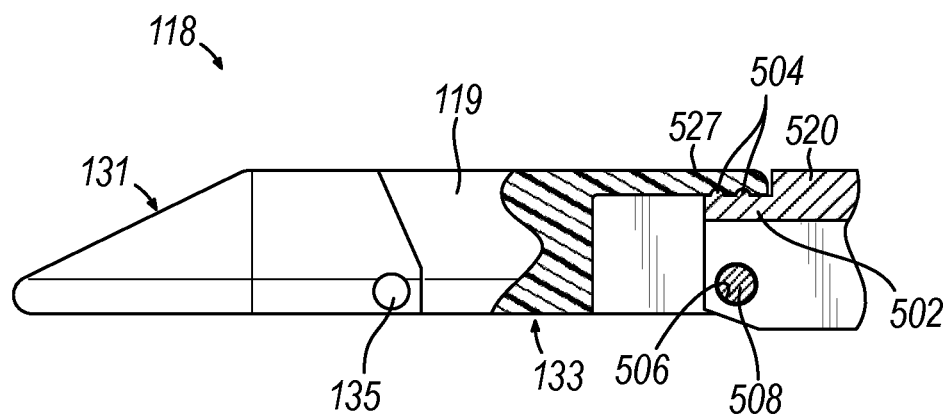
FIG. 16 depicts a cross sectional side view of an alternate anvil of an end effector for use with the surgical instruments described herein, and similar to the anvil of FIG. 14 but having multiple rotatable tip portions.

FIG. 16 illustrates another exemplary anvil (118) usable with the end effectors described herein and others. Anvil (118) is similar to anvil (518) described above except for the differences noted below. Thus, the description above for anvil (518) applies equally to anvil (118).

Anvil (118) comprises a body (520) and a tip (119) extending distally from body (520). The features and functions of anvil (518) apply equally to anvil (118) including the features and functions of tip (519) applying equally to tip (119). However, tip (119) includes additional features and functionality. Specifically, tip (119) comprises a distal portion (131) and a proximal portion (133). Furthermore, tip (119) is configured such that not only is proximal portion (133) rotatable to discrete positions relative to body (520) of anvil (118) as described above with respect to anvil (118), but distal portion (131) is rotatable to discrete positions relative to proximal portion (133) of tip (119).

Moreover, in the illustrated version, the rotatability of distal portion (131) relative to proximal portion (133) occurs in the same manner as the rotatability of proximal portion (133) relative to body (520) of anvil (118). As shown in FIG. 16, a pin (135) extends through and connects distal portion (131) and proximal portion (133). And further pin (135) provides and defines an axis of rotation about which distal portion (131) may rotate. In this manner, tip (119) is comprised of multiple pinned pieces or sections. This configuration allows for a greater angle and also in some versions an overall curvature-like shape to be achieved with otherwise straight but angled sections of tip (119).

As mentioned, the same or similar configuration of detents (504) can be used with distal and proximal portions (131, 133) of tip (119) to achieve the rotation to discrete positions. For example, in one version a first discrete position for distal portion (131) is a straight orientation relative to proximal portion (133) as shown in FIG. 16. A second discrete position for distal portion (131) is an angled or curved orientation relative to proximal portion (133) where distal portion (131) bends or angles downward toward lower jaw (16, 216) of the associated end effector. Of course, in some other versions, the second discrete position for distal portion (131) could be flared or bent upward relative to proximal portion (133). In view of the teachings herein, other configurations and ways to achieve such configurations for a tip (119) having multiple rotatable pinned sections will be apparent to those of ordinary skill in the art.

B. Exemplary End Effector Pivoting Tip with Fulcrum Feature

Figure 17:
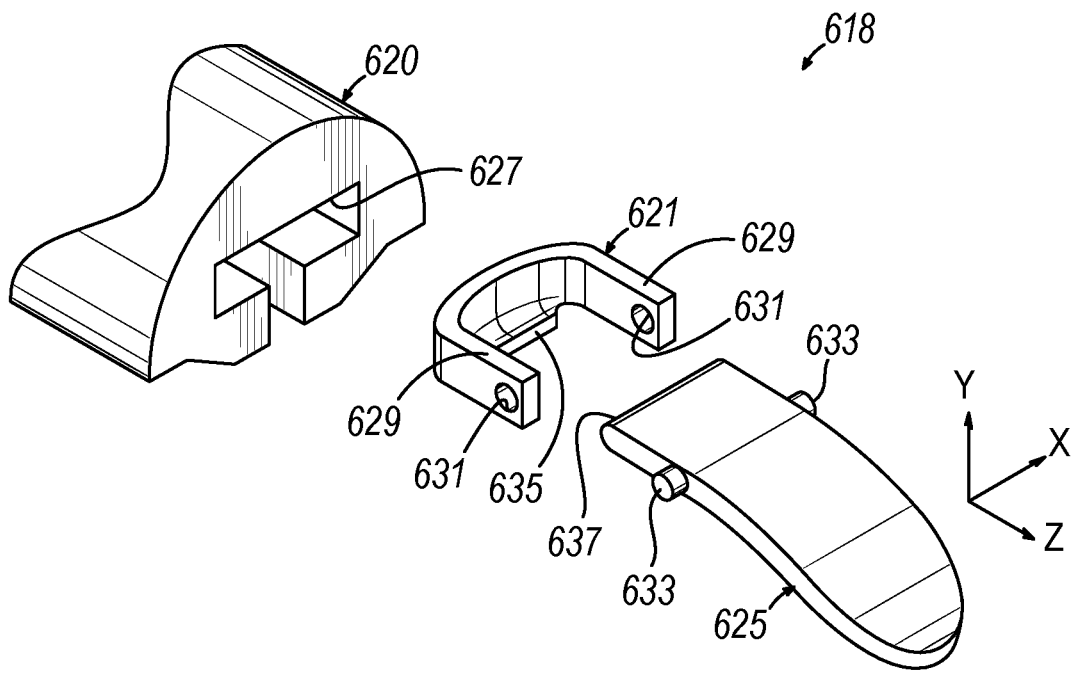
FIG. 17 depicts a perspective view of an alternate anvil of an end effector for use with the surgical instruments described herein.
Figure 18:
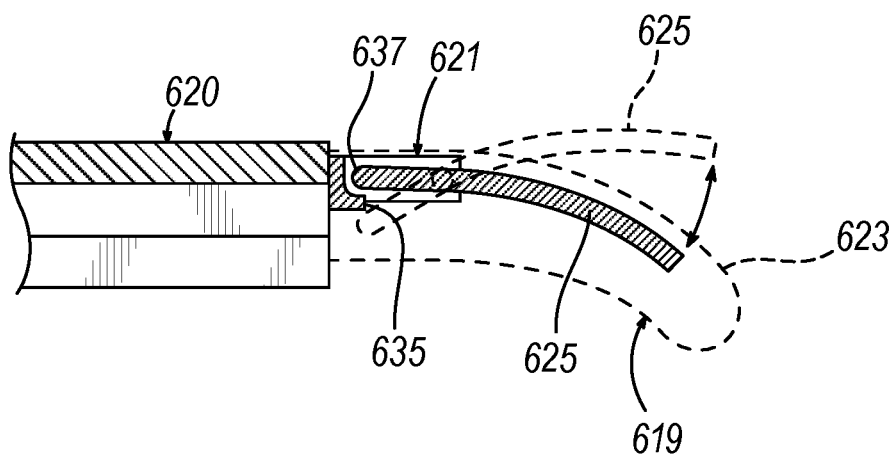
FIG. 18 depicts a cross sectional side view of the anvil of FIG. 17, shown with the elastomeric overmold in phantom, and showing a pivot member pivotable about a fulcrum feature.

FIGS. 17 and 18 depict a portion of an exemplary anvil (618) that is usable with the end effectors described herein and others. For instance anvil (618) can be interchanged or used in place of anvils (18, 218, 318) of respective end effectors (12, 212, 312, 412) described above. It will be appreciated that end effectors (12, 212, 312, 412) incorporating anvil (618) may be used with instruments (10, 310) and the other surgical instruments described herein. To this extent, end effectors (12, 212, 312, 412) incorporating anvil (618) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvil (618) is operable to pivot relative to lower jaws (16, 216). Anvil (618) and lower jaws (16, 216) may clamp tissue (90) similarly to clamping performed by anvil (18) and lower jaw (16) shown in FIG. 7. Anvil (618) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating anvil (618) further comprises a cartridge (37, 237) containing staples where cartridge (37, 237) is operable to be placed in lower jaw (16, 216).

Anvil (618) comprises body (620), tip (619), and connection member (621). Tip (619) comprises a polymeric or metallic covering (shown as an elastomeric overmold (623)) and a pivot member (625) as best seen in FIG. 18. Connection member (621) is configured to attach with body (620). In one version connection member (621) comprises a metal stamping configured to be welded to body (620) of anvil (618). In another version, connection member (621) is configured to be press-fit or clicked to body (620). In such versions, connection member (621) may comprise features that engage with slot (627) of body (620). In view of the teachings herein, other ways to attach connection member (621) with body (620) of anvil (618) will be apparent to those of ordinary skill in the art.

Connection member (621) comprises arms (629) that extend distally. Arms (629) each comprise bores (631) that are configured to receive projections (633) of pivot member (625). In this manner, bores (631) provides a pivot axis or axis of rotation for tip (619). Connection member (621) further comprises a curved lip (635) that acts like a fulcrum feature. Curved lip (635) protrudes distally and is configured to interact with a proximal end (637) of pivot member (625) of tip (619).

Pivot member (625) is connectable with connection member (621) as mentioned, with projections (633) being received within bores (631) of connection member (621). With this configuration, pivot member (625) is rotatably adjustable relative to connection member (621) and body (620) of anvil (618). When projections (633) are within bores (631), proximal end (637) of pivot member (625) is located in a slight overlapping orientation relative to curved lip (635). The remainder of pivot member (625) extends distally from connection member (621). As shown in FIG. 18, elastomeric overmold (623), shown in phantom to reveal internal components, covers pivot member (625) and connection member (621).

With the above configuration for anvil (618), tip (619) is configured to rotate or pivot about the pivot axis defined by bores (631), whereby proximal end (637) of pivot member (625) can adopt discrete positions relative to curved lip (635), such that tip (619) adopts discrete positions relative body (620). For instance, as shown in FIG. 18 by the solid lines illustrating pivot member (625), in a first position, pivot member (625) can have an angled orientation. In the illustrated version, this corresponds to when proximal end (637) of pivot member (625) is above curved lip (635). As shown in FIG. 18 by the broken lines illustrating pivot member (625), in a second position, pivot member (625) can have a straight or slightly flared orientation. In the illustrated version, this corresponds to when proximal end (637) of pivot member (625) is below curved lip (635).

In the present example, elastomeric overmold (623) acts as the spring that holds pivot member (625) in place on either side of curved lip (635) until a sufficient force is applied to tip (619) to overcome the bias provided by elastomeric overmold (623) and the contact between proximal end (637) and curved lip (635). For instance, when in the angled or curved orientation, when a sufficient upward force is applied to tip (619), proximal end (637) of pivot member (625) will rotate downward and click past curved lip (635) allowing tip (619) to adopt the other discrete position. Similarly, when in the straight or flared orientation, when a sufficient downward force is applied to tip (619), proximal end (637) of pivot member (625) will rotate upward and click past curved lip (635) allowing tip (619) to adopt the other discrete position.

In the present example, proximal end (637) is rounded and toleranced so that it clicks past curved lip (635), which acts as the fulcrum feature. In some other versions, curved lip (635) can incorporate a rounded and toleranced distal end to facilitate movement of proximal end (637) from one side of curved lip (635) to the other side of curved lip (635). Again, as mentioned, once on either side of curved lip (635) or other fulcrum feature, tip (619) will remain in place because of elastomeric overmold (623) acting as the spring to hold pivot member (625) in place.

In one version of anvil (618), tuning for force or sound feedback could be accomplished by configuring the fulcrum feature with a deformable dome-type geometry that proximal end (637) moves past when changing discrete positions. In other words, greater or lesser deformation can be used with the fulcrum feature so that a user gets haptic and/or audible feedback confirming tip (619) has changed position. In view of the teachings herein, other ways to modify anvil (618), connection member (621), and tip (619) to achieve a pivoting tip that adopts discrete positions will be apparent to those of ordinary skill in the art.

C. Exemplary End Effector Pivoting Tip with Triangular Pivot Member

Figure 19:
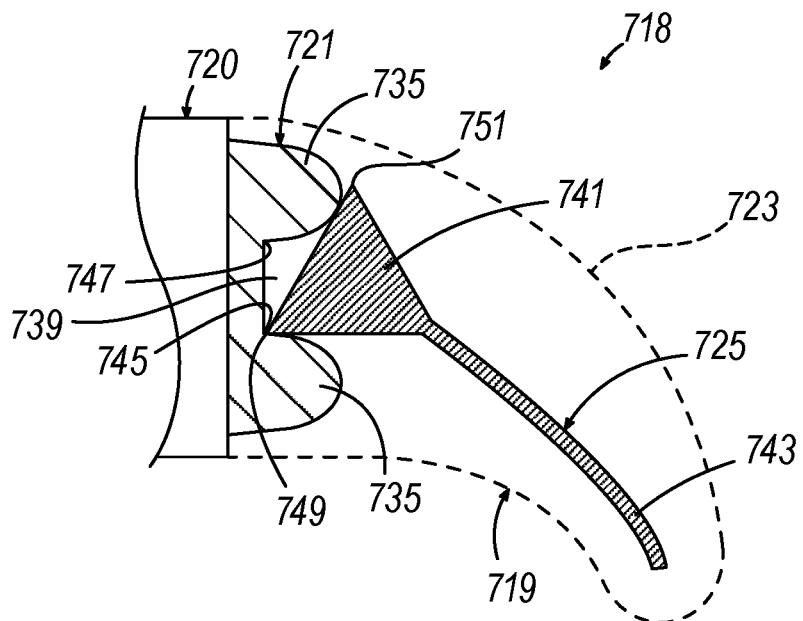
FIG. 19 depicts a perspective view of an alternate tip of an anvil of an end effector for use with the surgical instruments described herein, shown with the tip in a first position.
Figure 20:
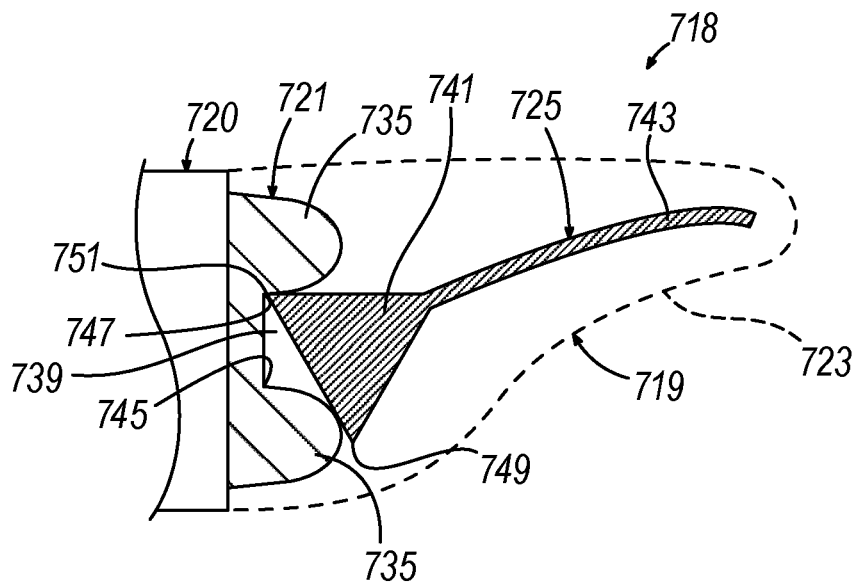
FIG. 20 depicts a perspective view of the tip of FIG. 19, shown with the tip in a second position.

FIGS. 19 and 20 depict a portion of an exemplary anvil (718) that is usable with the end effectors described herein and others. For instance, anvil (718) can be interchanged or used in place of anvils (18, 218, 318) of respective end effectors (12, 212, 312, 412) described above. It will be appreciated that end effectors (12, 212, 312, 412) incorporating anvil (718) may be used with instruments (10, 310) and the other surgical instruments described herein. To this extent, end effectors (12, 212, 312, 412) incorporating anvil (718) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvil (718) is operable to pivot relative to lower jaws (16, 216). Anvil (718) and lower jaws (16, 216) may clamp tissue (90) similarly to clamping performed by anvil (18) and lower jaw (16) shown in FIG. 7. Anvil (718) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating anvil (718) further comprises a cartridge (37, 237) containing staples where cartridge (37, 237) is operable to be placed in lower jaw (16, 216).

Anvil (718) comprises body (720), tip (719), and connection member (721). Tip (719) comprises a polymeric or metallic covering (shown as an elastomeric overmold (723)) and a pivot member (725). Connection member (721) is configured to attach with body (720). In one version connection member (721) comprises a metal stamping configured to be welded to body (720) of anvil (718). In another version, connection member (721) is configured to be press-fit or clicked to body (720). In such versions, connection member (721) may comprise features that engage with a slot of body (720), similar to slot (627) of body (620). In view of the teachings herein, other ways to attach connection member (721) with body (720) of anvil (718) will be apparent to those of ordinary skill in the art.

Connection member (721) comprises a dual bump feature (735) that extends distally. As shown in the illustrated version, connection member (721) further comprises a space or gap (739) between the bumps of dual bump feature (735). In the present example, but not required in all versions, dual bump feature (735) is rigid. Pivot member (725) comprises triangular body (741) and elongated member (743) connected with and extending distally from triangular body (741). In the present example, but not required in all versions, pivot member (725) comprises a metallic structure.

In the present example, dual bump feature (735) is dimensioned and toleranced to interact with triangular body (741) of pivot member (725). For instance, dual bump feature (735) defines base corners (745, 747), and triangular body (741) defines vertexes (749, 751). As shown in FIG. 19, when tip (719) is in a first discrete position where tip (719) has a downward angled orientation, vertex (749) is biased into base corner (745). At the same time, vertex (751) is pivoted away from base corner (747) and is instead near a distal end of dual bump feature (735). As shown in FIG. 20, when tip (719) is in a second discrete position where tip (719) has a straight or upward angled orientation, vertex (751) is biased into base corner (747). At the same time, vertex (749) is pivoted away from base corner (745) and is near a distal end of dual bump feature (735).

In the present example, elastomeric overmold (723) biases triangular body (741) proximally. Thus, elastomeric overmold (723) acts as the spring that holds triangular body (741) of pivot member (725) in place against dual bump feature (735). However, when a sufficient force is applied to tip (719) to overcome the proximal bias imposed by elastomeric overmold (723), triangular body (741) pivots between dual bump feature (735) as illustrated by the change in position of triangular body (741) in FIGS. 19 and 20. For instance, when in the angled or curved orientation, shown in FIG. 19, when a sufficient upward and/or distally directed force is applied to tip (719), vertex (749) of triangular body (741) travels distally along a lower bump of dual bump feature (735). Meanwhile, vertex (751) of triangular body (741) of pivot member (725) travels proximally along an upper bump of dual bump feature (735) until locking into base corner (747). Similarly, when in the straight or upward bent orientation shown in FIG. 20, when a sufficient downward and/or distally directed force is applied to tip (719), vertex (749) of triangular body (741) travels proximally along a lower bump of dual bump feature (735) until locking into base corner (745). Meanwhile, vertex (751) of triangular body (741) of pivot member (725) travels distally along an upper bump of dual bump feature (735). In one version, toggling the position of tip (719) may involve a user pinching and pulling distally on tip (719) thereby temporarily deforming elastomeric overmold (723) when relocating tip (719). Still in other versions, toggling the position of tip (719) may involve a user pushing upward or downward such that the force is largely orthogonally applied to the longitudinal axis of anvil (718).

D. Exemplary End Effector Elastomeric Tip Having Internal Snap Clip

FIGS. 21-29 and FIGS. 30-32 depict exemplary end effectors (812, 912) with respective anvils (818, 918). End effectors (812, 912) can be interchanged or used in place of end effectors (12, 212, 312, 412) described above. It will be appreciated that end effectors (812, 912) may be used with instruments (10, 310) and the other surgical instruments described herein. To this extent, end effectors (812, 912) with respective anvils (818, 918) may be integrally formed with instruments (10, 310) and the other surgical instruments described herein, or in the alternative may be interchangeable end effectors of instruments (10, 310) and the other surgical instruments described herein.

End effectors (812, 912) are operable to clamp tissue (90) similarly to clamping performed by end effector (12) shown in FIG. 7. End effectors (812, 912) are further operable to cut and staple clamped tissue (90) similarly to the cutting and stapling performed by end effector (12) shown in FIG. 7.

1. Internal Snap Clip with Distal Rivet Connection

Figure 21:
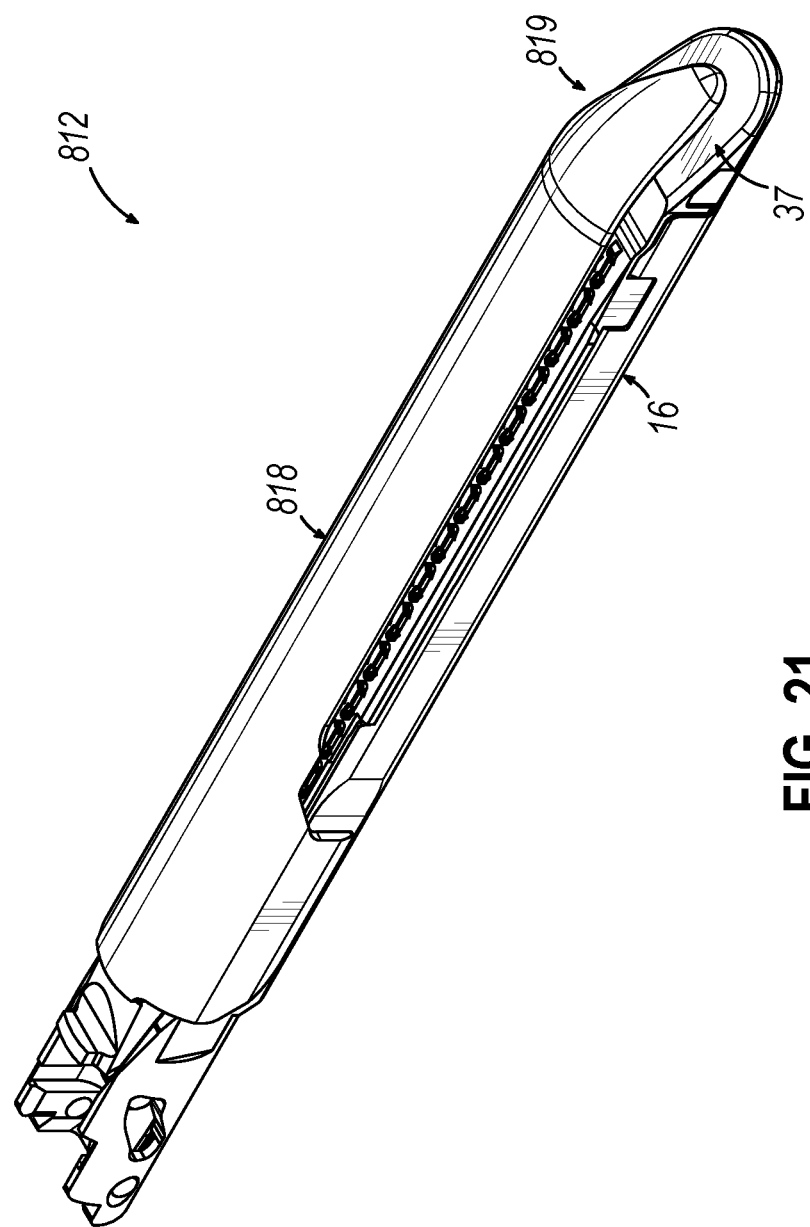
FIG. 21 depicts a perspective view of an exemplary alternate end effector for use with the surgical instruments described herein, showing a tip of an anvil in a first position.
Figure 22:
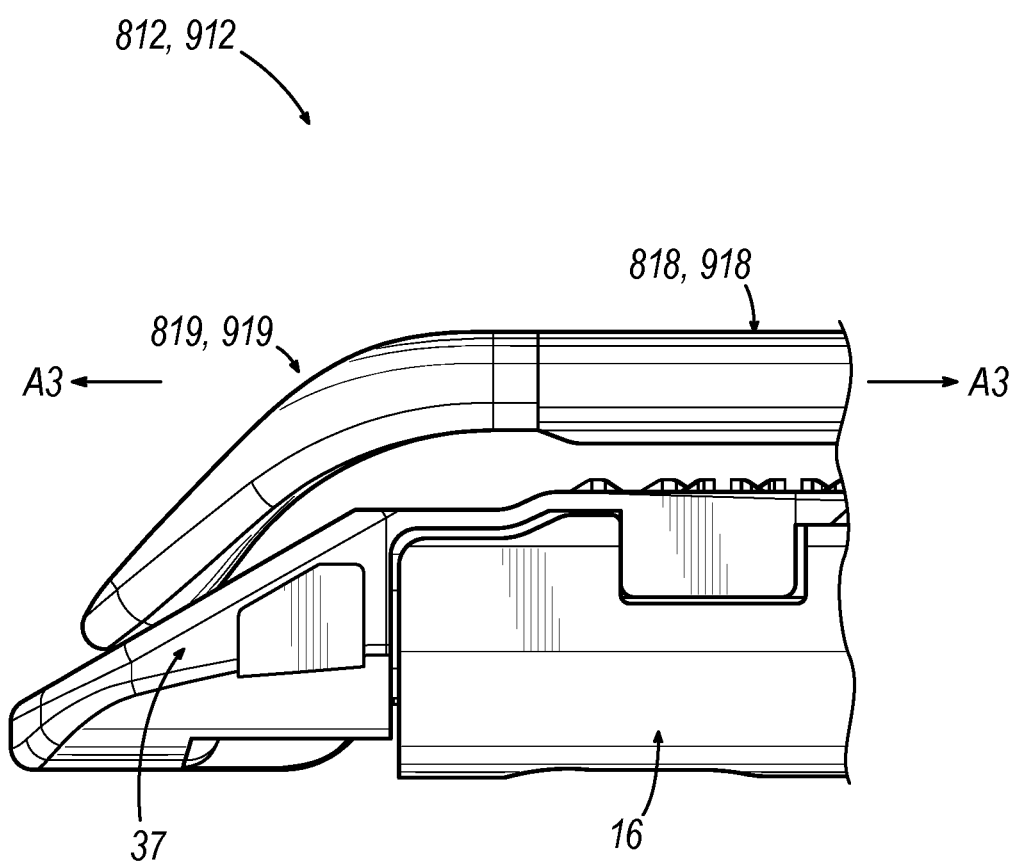
FIG. 22 depicts an enlarged side view of the end effector of FIG. 21.
Figure 23:
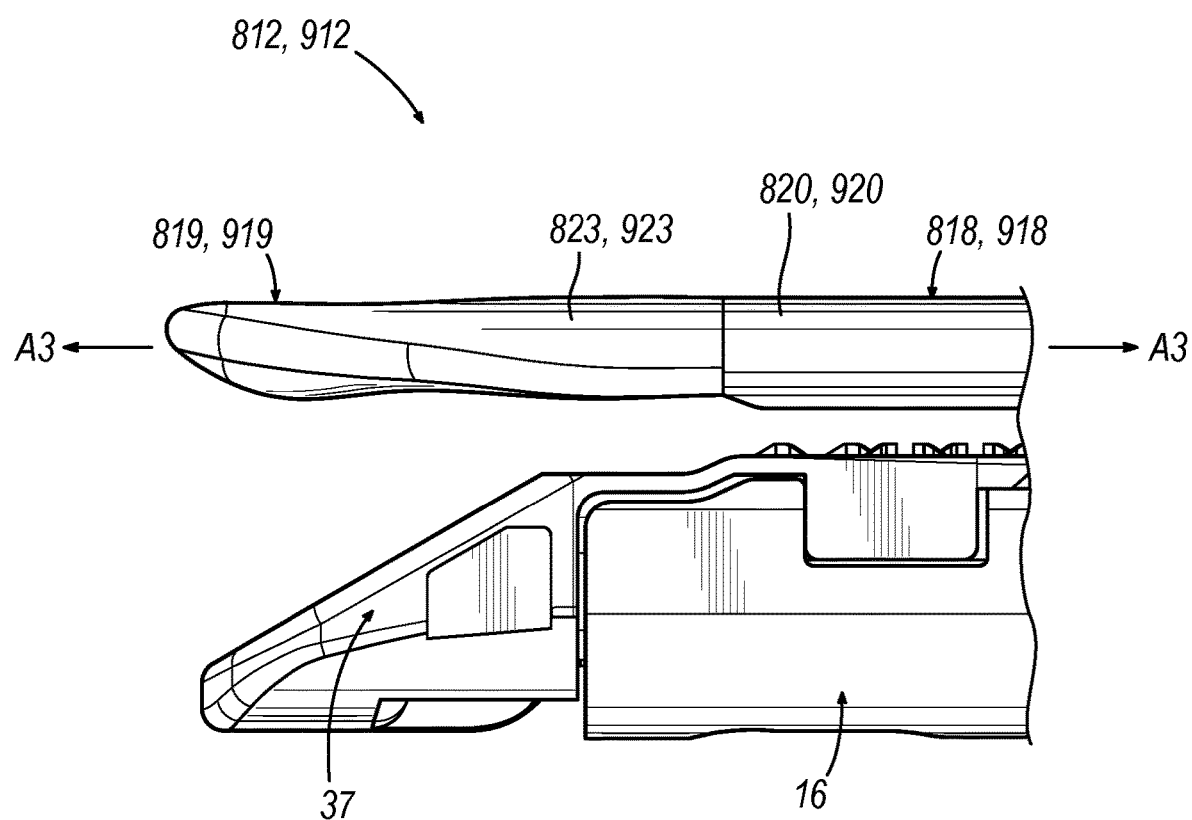
FIG. 23 depicts an enlarged side view of the end effector of FIG. 21, showing the tip of the anvil in a second position.

FIGS. 21-23 illustrate an exemplary end effector (812) comprising anvil (818), lower jaw (16), and staple cartridge (37) positioned within lower jaw (16). Lower jaw (16) and cartridge (37) are described above with respect to other end effectors and those descriptions apply equally here to end effector (812). Anvil (818) comprises a tip (819). Tip (819) includes a deformable member that is flexible, such that tip (819) is movable relative to anvil (818) between a first discrete position and a second discrete position using the deformable member. For instance, the first discrete position is illustrated in FIGS. 21 and 22 where tip (819) has an angled or curved orientation relative to a longitudinal axis (A3) of anvil (818) until the deformable member is acted upon by an external input force. The second discrete position is illustrated in FIG. 23 where tip (819) has a straight orientation relative to longitudinal axis (A3) until the deformable member is acted upon by an external input force. With the straight orientation, tip (819) is generally aligned with the remainder of anvil (818), and tip (819) extends parallel to longitudinal axis (A3). With the angled orientation, tip (819) is angled relative to longitudinal axis (A3) such that tip (819) extends towards lower jaw (16) and cartridge (37). In some embodiments, the angled orientation may form a curved orientation.

When using end effector (812), a user may select a desired discrete position for tip (819). This may be done, for example, when reloading a new cartridge (37) onto end effector (812). The user may select the angled orientation for tip (819) when the user is trying to position and navigate anvil (818) around tissue such as a vessels and other tubular structures. The user may select the straight orientation for tip (819) when the user is trying to get over tissue as the straight orientation for tip (819) gives a larger aperture compared to the angled orientation for tip (819). The user may also select the straight orientation for tip (819) when the user is performing a procedure involving marching as described above.

Figure 24:
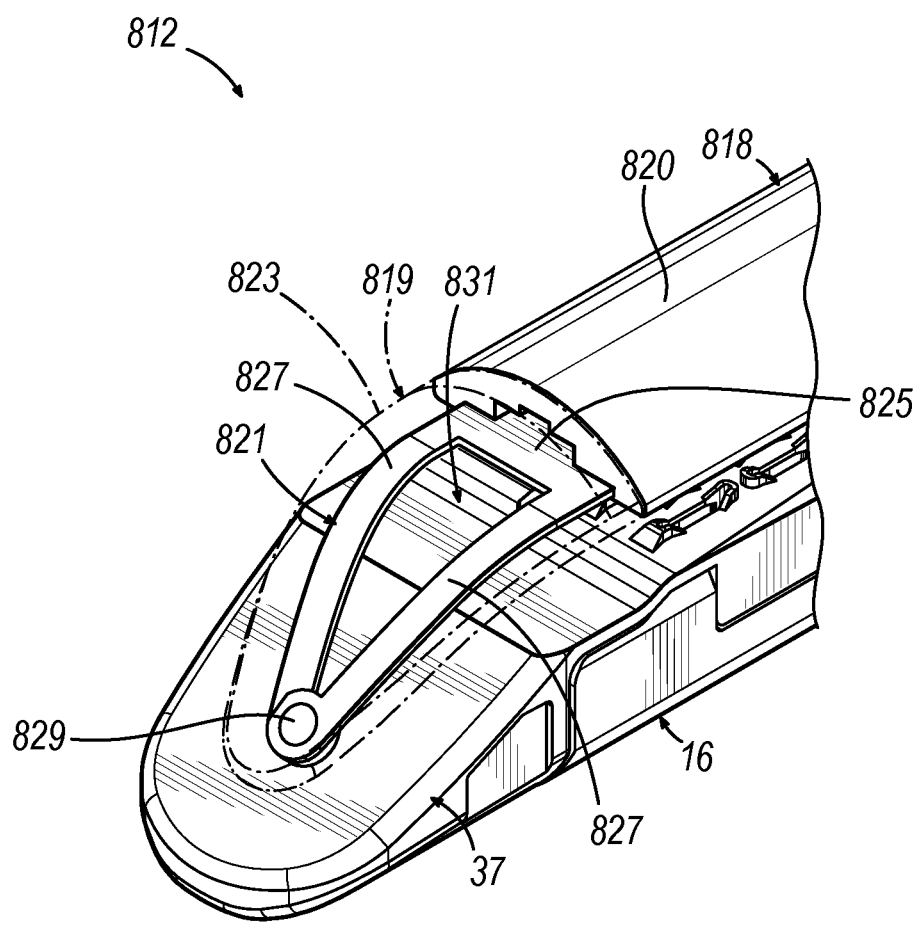
FIG. 24 depicts an enlarged perspective view of the end effector of FIG. 21, showing an elastomeric overmold in phantom to reveal an internal clip, and showing the tip of the anvil in the first position.

The deformable member may include a polymeric or metallic covering and an internal support structure. FIG. 24 illustrates an enlarged perspective view of a distal end of end effector (812), where a polymeric or metallic covering (shown as an elastomeric overmold (823)) of tip (819) is shown transparently to reveal internal components of tip (819). Deformable member of tip (819) may include an internal support structure (shown as an internal clip (821) in FIG. 24) so that tip (819) remains in the desired discrete position until acted upon by an external input force. While internal clip (821) shows one such suitable support structure, other support structures having various shapes and sizes are also envisioned. In the illustrated version, internal clip (821) connects with and extends distally from a body (820) of anvil (818). Internal clip (821) comprises a base (825) and a pair of arms (827) extending distally from base (825). Arms (827) converge as they extend distally, and arms (827) are joined at their respective distal end by a rivet (829) as shown in the present example. Internal clip (821) further comprises a space (831) between arms (827), and in the present example, space (831) has a triangular shape.

Internal clip (821) is configured as an over-center snap clip having two discrete positions that correspond to the angled orientation and straight orientation of tip (819) as described above. Furthermore, internal clip (821) may be overmolded with an elastomeric material such that tip (819) comprises elastomeric overmold (823) as mentioned above. Still in some other versions, internal clip (821) may be inserted within an otherwise formed flexible tip such that it is not required that internal clip (821) be overmolded to be surrounded by elastomeric material.

Figure 25:
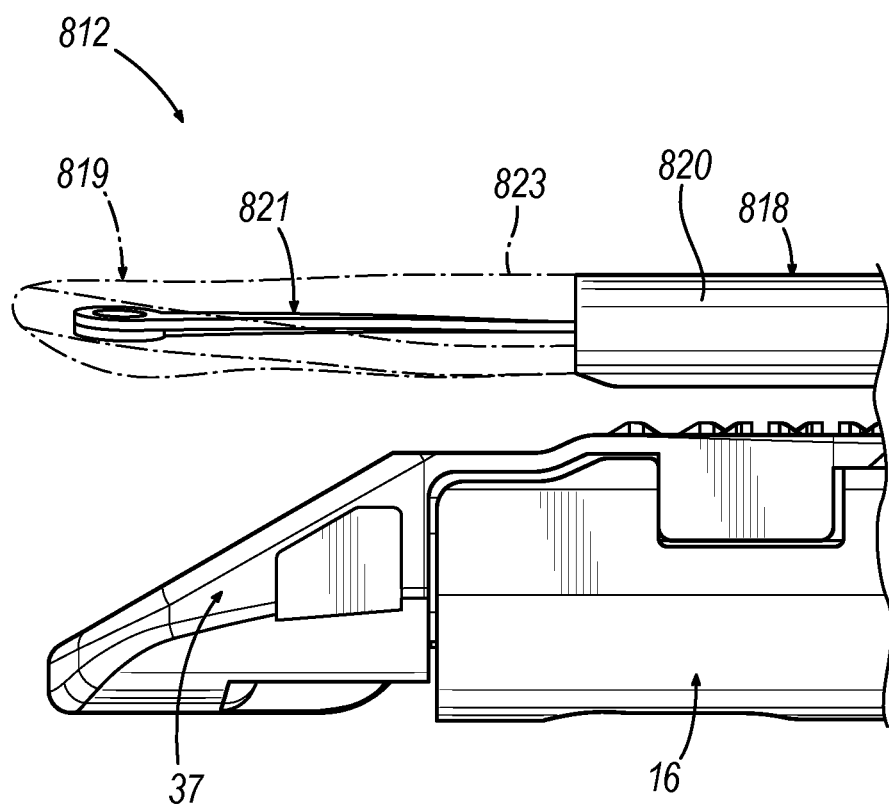
FIG. 25 depicts a side view of the end effector of FIG. 24, showing the tip of the anvil in the second position.

When using end effector (812) having anvil (818) and tip (819), to toggle or switch the discrete position of tip (819), a user would apply a force to tip (819) in the direction the user wanted tip (819) to move. For instance, where the deformable member of tip (819) is in the first discrete position with the angled orientation as shown in FIG. 24, by opening end effector (812) and applying an upward force from an underside of tip (819), internal clip (821) will snap into its straight orientation associated with the second discrete position as described above. FIG. 25 illustrates tip (819) in the straight orientation and showing the elastomeric overmold (823) as transparent to reveal internal clip (821) in this state or position. Similarly, where deformable member of tip (819) is in the second discrete position with a straight orientation as shown in FIG. 25, when applying a sufficient downward force from a top side of tip (819), internal clip (821) will snap into its angled (e.g. bent or curved) orientation associated with the first discrete position as described above. In this manner, internal clip (821) is deflectable and comprises a bias to assume either a first position associated with an angled orientation for tip (819), or a second discrete position associated with a straight orientation for tip (819).

Figure 26:
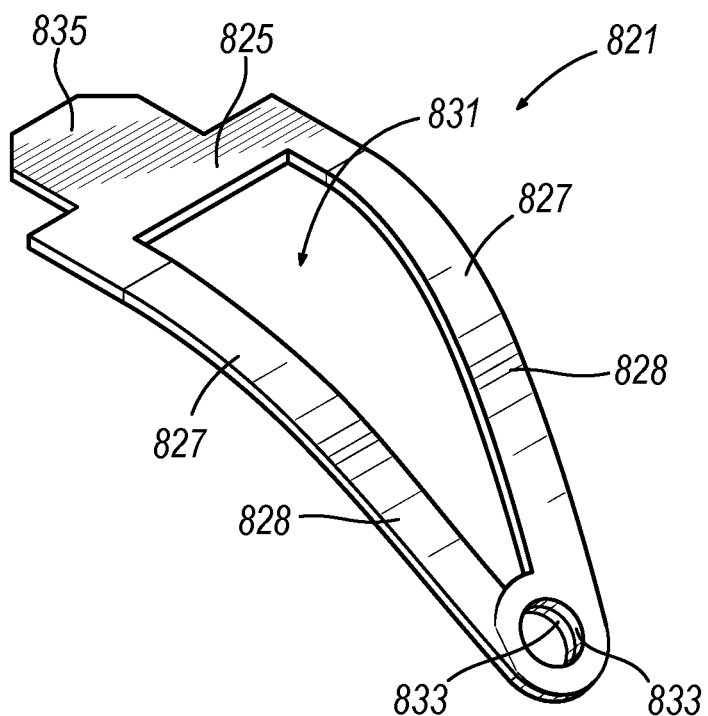
FIG. 26 depicts a perspective view of the internal clip of the end effector of FIG. 24.
Figure 27:
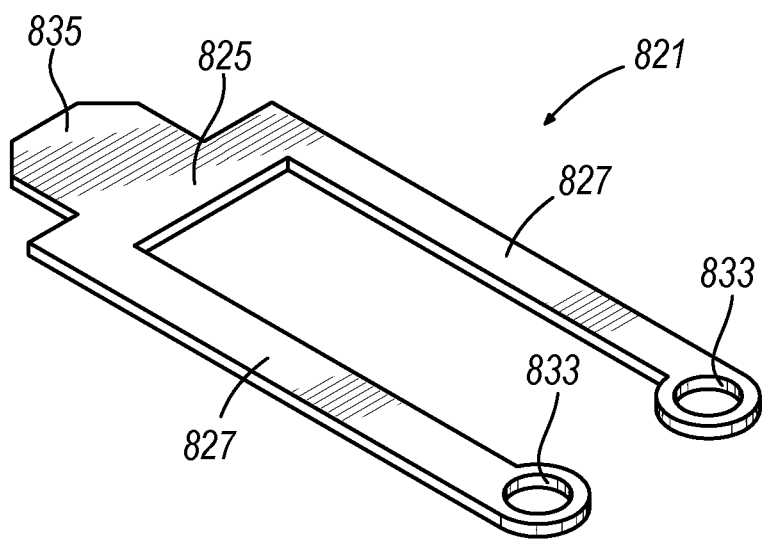
FIG. 27 depicts a perspective view of the internal clip of FIG. 26, shown with a pair of arms of the internal clip prior to joining their distal ends.

FIGS. 26 and 27 illustrate internal clip (821) and further features thereof. As shown, rivet (829) is omitted from FIGS. 26 and 27, revealing that arms (827) each comprise a bore (833) at their distal ends. Bores (833) are each configured and sized to receive rivet (829) and thereby join arms (827). FIG. 26 shows internal clip (821) in its assembled or shaped form where arms (827) have been forced toward one another to align bores (833) of each to ultimately receive rivet (829). FIG. 27 shows internal clip (821) in its unassembled or stamped form where arms (827) do not converge and bores (833) do not align. In the illustrated version of FIGS. 26 and 27, internal clip (821) comprises a stamped metal structure. However, in other examples, other materials besides metal may be used to construct internal clip (821).

Referring to FIG. 26, a proximal extension (835) of internal clip (821) is configured to be received by and connected to body (820) of anvil (818). In this manner, internal clip (821) is secured to anvil (818). In some versions, internal clip (821) may be welded to body (820) of anvil (818), for instance, welding proximal extension (835) to body (820). In view of the teachings herein, various other ways to connect internal clip (821) with anvil (818) will be apparent to those of ordinary skill in the art.

Figure 28:
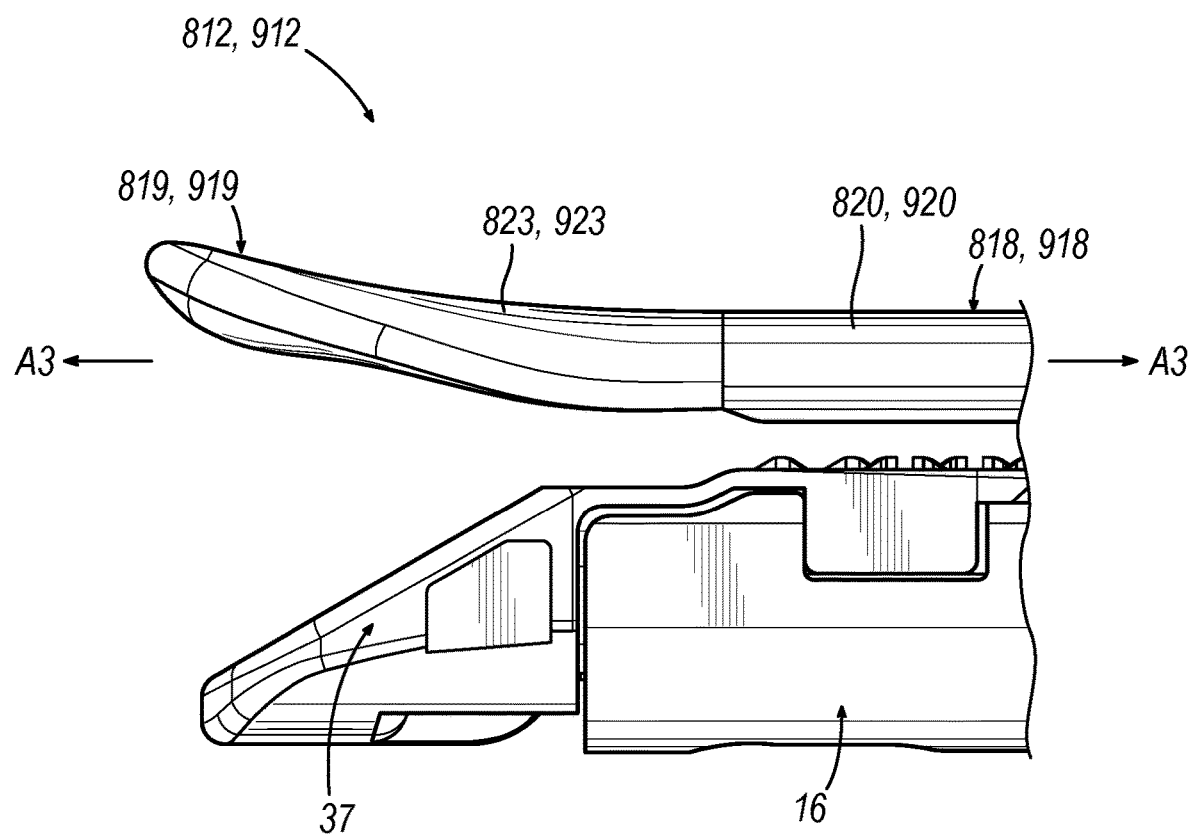
FIG. 28 depicts an enlarged side view of the end effector of FIG. 21, showing the tip of the anvil in an alternate second position.
Figure 29:
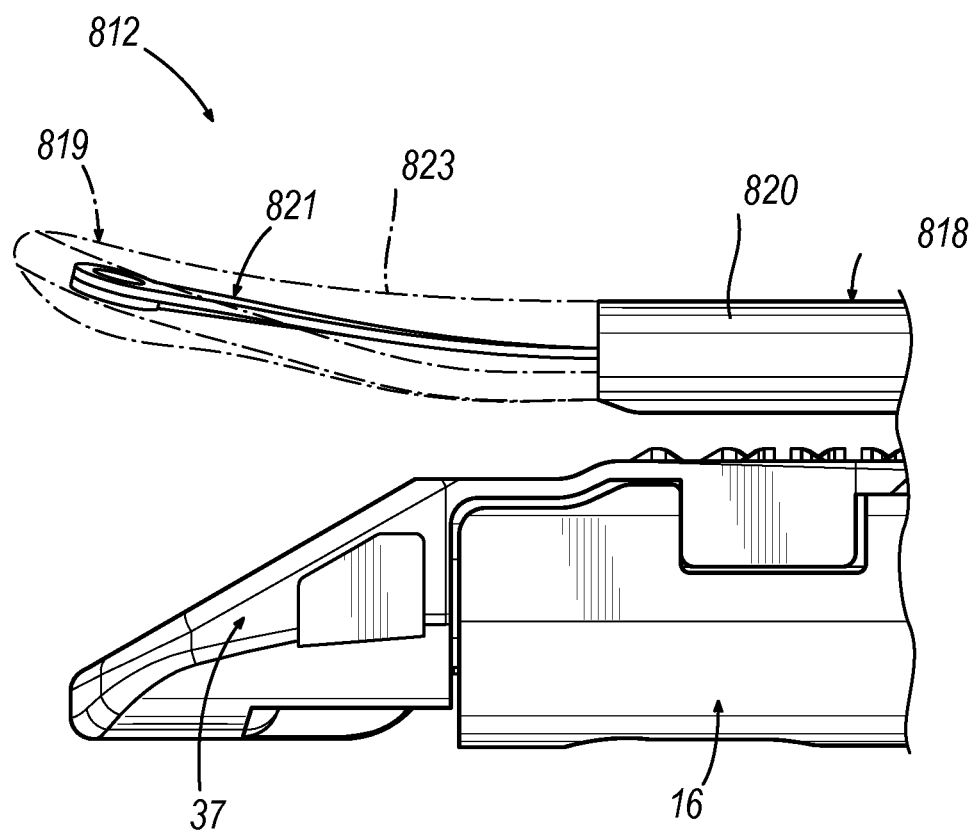
FIG. 29 depicts a side view of the end effector of FIG. 28, showing an elastomeric overmold in phantom to reveal an internal clip.

FIGS. 28 and 29 depict another version of end effector (812) where internal clip (821) is configured with a bias to assume either a first discrete position associated with a curved orientation for tip (819) as shown and described above with respect to FIGS. 21, 22, and 24, or to assume a second discrete position associated with a flared orientation for tip (819) as shown in FIGS. 28 and 29. In some examples, a flared orientation may also be referred to as a crowned orientation. With a flared orientation, tip (819) is angled upward relative to longitudinal axis (A3) of anvil (818). As compared with the straight orientation for tip (819) shown and described above, a flared orientation provides for an even greater aperture, which may be useful when trying to get over tissue, and/or when conducting procedures involving marching. Other than changing the second discrete position from straight to flared, the remaining features and functions of end effector (812) as shown in FIGS. 28 and 29 are the same as that shown and described above with respect to FIGS. 21-27.

In some examples, the geometry and material of both elastomeric overmold (823) and/or internal clip (821) may contribute to the discrete positions of tip (819). For instance, in one example, a change to a more flexible elastomer for elastomeric overmold (823) may permit internal clip (821) to change positions to a greater extent. In one version, this is a way to change the configuration of tip (819) from having angled and straight orientations to instead having angled and flared orientations. In another example, internal clip (821)

may be made stiffer by increasing its mass, altering its material, or altering the geometry of internal clip (821). Such an increase in stiffness may overcome the counterforce or bias imparted on the tip (819) by elastomeric overmold (823). This may be another way to change the configuration of tip (819) from having a angled and straight orientations to instead having a angled and flared orientation. Still yet in some versions of end effector (812) with anvil (818), tip (819) may be configured to provide angled, straight, and flared orientations, and thus, tip (819) would have three discrete positions available to the user. In view of the teachings herein, various other ways to configure the components of tip (819) to achieve the desired discrete positions for tip (819) will be apparent to those of ordinary skill in the art.

2. Proximally Pinned Internal Snap Clip

Figure 30:
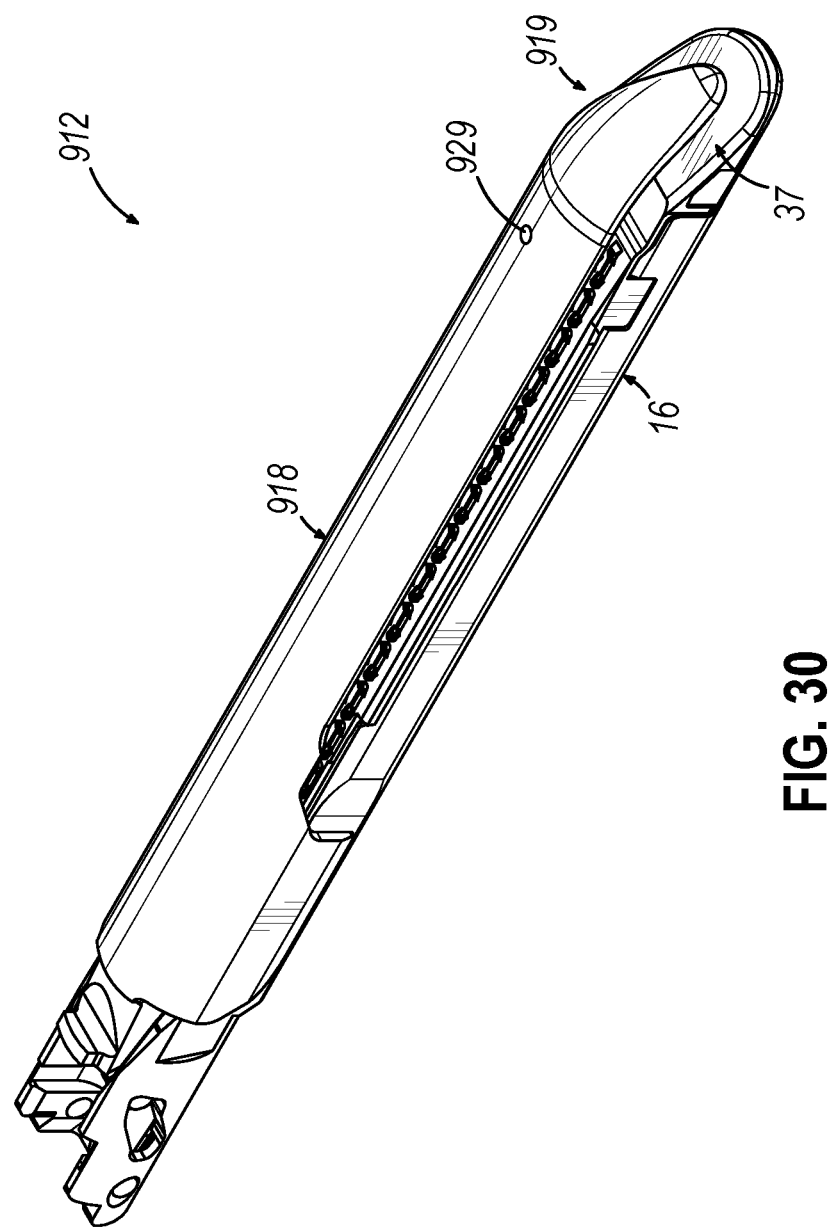
FIG. 30 depicts a perspective view of an exemplary alternate end effector for use with the surgical instruments described herein, showing a tip of an anvil in a first position.
Figure 31:
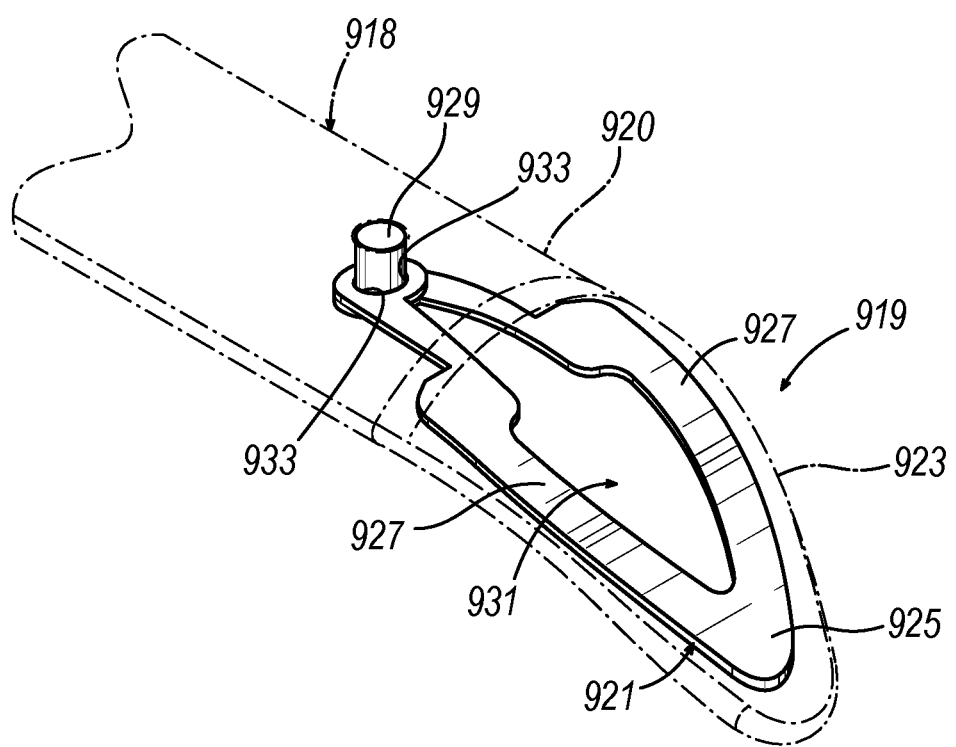
FIG. 31 depicts an enlarged perspective view of a tip of the anvil of the end effector of FIG. 30, showing an elastomeric overmold in phantom to reveal an internal clip.
Figure 32:
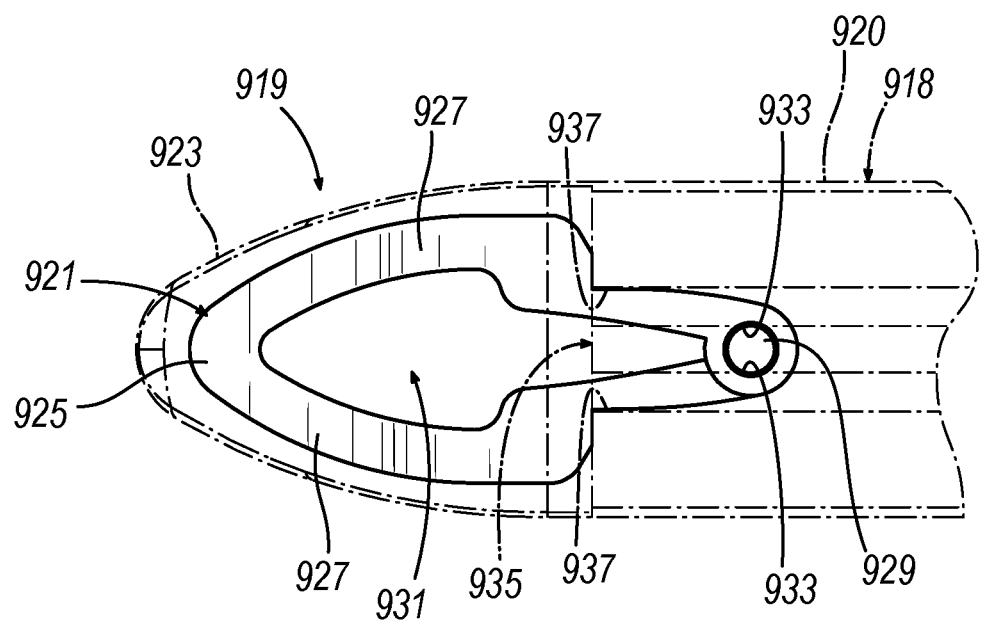
FIG. 32 depicts a top view of the tip of the anvil of the end effector of FIG. 31.

FIGS. 30-32 illustrate an exemplary end effector (912) comprising anvil (918), lower jaw (16), and staple cartridge (37) positioned within lower jaw (16). Lower jaw (16) and cartridge (37) are described above with respect to other end effectors and those descriptions apply equally here to end effector (912). Anvil (918) comprises a tip (919). Tip (919) includes a deformable member that is flexible, such that tip (919) is movable relative to anvil (918) between a first discrete position and a second discrete position using the deformable member. For instance, the first discrete position is illustrated in FIGS. 30 and 22 where tip (919) has a angled (e.g., curved) or bent orientation relative to a longitudinal axis (A3) of anvil (918) until the deformable member is acted upon by an external input force. The second discrete position is illustrated in FIG. 23 where tip (919) has a straight orientation relative to longitudinal axis (A3) until the deformable member is acted upon by an external input force. With the straight orientation, tip (919) is generally aligned with the remainder of anvil (918), and tip (919) extends parallel to longitudinal axis (A3). With the angled orientation, tip (919) is angled relative to longitudinal axis (A3) such that tip (919) extends towards lower jaw (16) and cartridge (37). In some embodiments, the angled orientation may form a curved orientation, as described above.

When using end effector (912), a user may select a desired discrete position for tip (919). This may be done, for example, when reloading a new cartridge (37) onto end effector (912). The user may select the angled orientation for tip (919) when the user is trying to position and navigate anvil (918) around tissue such as a vessels and other tubular structures. The user may select the straight orientation for tip (919) when the user is trying to get over tissue as the straight orientation for tip (919) gives a larger aperture compared to the angled orientation for tip (919). The user may also select the straight orientation for tip (919) when the user is performing a procedure involving marching as described above.

Deformable member may include a polymeric or metallic covering and an internal support structure. FIG. 31 illustrates an enlarged perspective view of a distal end of anvil (918) of end effector (912), where the polymeric or metallic covering (shown as an elastomeric overmold (923)) of tip (919) and body (920) of anvil (918) are shown transparently to reveal internal components. Deformable member of tip (919) may comprise an internal support structure (shown as internal clip (921)) that connects with and extends distally from a body (920) of anvil (918). Internal clip (921) comprises an apex portion (925) and a pair of arms (927) extending proximally from apex portion (925). Arms (927) initially diverge as they extend proximally, and then converge as they approach their respective proximal ends. Arms (927) are joined at their respective proximal ends by a pin (929) within body (920) of anvil (918) that extends through respective aligned bores (933) of arms (927) as shown in the present example. In some versions, pin (929) may be replaced by a rivet or by a spiral pin. Internal clip (921) further comprises a space (931) between arms (927), and in the present example, space (931) has a triangular shape.

Internal clip (921) is configured as an over-center snap clip having two discrete positions that correspond to the angled orientation and straight orientation of tip (919) as described above. Furthermore, internal clip (921) may be overmolded with an elastomeric material such that tip (919) comprises elastomeric overmold (923) as mentioned above. Still in some other versions, internal clip (921) may be inserted within an otherwise formed flexible tip such that it is not required that internal clip (921) be overmolded to be surrounded by elastomeric material.

When using end effector (912) having anvil (918) and tip (919), to toggle or switch the discrete position of tip (919), a user would apply a force to tip (919) in the direction the user wanted tip (919) to move. For instance, where tip (919) is in the first position with the angled orientation as shown in FIG. 30, by opening end effector (912) and applying an upward force from an underside of tip (919), internal clip (921) will snap into its straight orientation associated with the second discrete position as described above. Similarly, where tip (919) is in the second discrete position with a straight orientation as shown in FIG. 23, when applying a sufficient downward force from a top side of tip (919), internal clip (921) will snap into its curved or bent orientation associated with the first discrete position as described above. In this manner, internal clip (921) is deflectable and comprises a bias to assume either a first position associated with an angled orientation for tip (919), or a second discrete position associated with a straight orientation for tip (919).

FIG. 32 illustrates a top view of internal clip (921) and further features thereof. As shown, pin (929) extends orthogonally relative to the longitudinal axis of body (920) of anvil (918). Arms (927) are positioned to align bores (933) such that bores (933) are each configured and sized to receive pin (929) and thereby join arms (927). As shown in FIG. 32, internal clip (921) is in its assembled or shaped form where arms (927) have been forced toward one another to align bores (933) of each to ultimately receive pin (929). Similar to internal clip (821) described above, internal clip (921) also has an unassembled or stamped form where arms (927) do not converge and bores (933) do not initially align. In one version, internal clip (921) comprises a stamped metal structure. However, in other examples, other materials besides metal may be used to construct internal clip (921). In view of the teachings herein, various other ways to connect internal clip (921) with anvil (918) will be apparent to those of ordinary skill in the art.

FIG. 28 depicts another version of end effector (912) where internal clip (921) is configured with a bias to assume either a first discrete position associated with a curved orientation for tip (919) as shown and described above with respect to FIG. 30, or to assume a second discrete position associated with a flared orientation for tip (919) as shown in FIG. 28. In some examples a flared orientation may also be referred to as a crowned orientation. With a flared orientation, tip (919) is angled upward relative to longitudinal axis (A3) of anvil (918). As compared with the straight orientation for tip (919) shown and described above, a flared orientation provides for even greater aperture, which may be useful when trying to get over tissue, and/or when conducting procedures involving marching. Other than changing the second discrete position from straight to flared, the remaining features and functions of end effector (912) as shown in FIG. 28 are the same as that shown and described above with respect to FIGS. 30-32.

To alter the discrete positions that internal clip (921) may take, in some examples both elastomeric overmold (923) and/or internal clip (921) geometry and material can contribute to the discrete positions that tip (919) will adopt. For instance, in one example, a change to a more flexible elastomer for elastomeric overmold (923) can permit internal clip (921) to change positions to a greater extent. In one version, this is a way to change the configuration of tip (919) from having curved and straight orientations to instead having curved and flared orientations. In another example, internal clip (921) may be made stiffer by increasing its mass, altering its material, and/or altering its geometry. Such an increase in stiffness can overcome the counterforce or bias imparted on the tip (919) by elastomeric overmold (923). This can be another way to change the configuration of tip (919) from having curved and straight orientations to instead having curved and flared orientations. Still yet in some versions of end effector (912) with anvil (918), tip (919) may be configured to provide curved, straight, and flared orientations and thus tip (919) would have three discrete positions available to the user. In view of the teachings herein, various other ways to configure the components of tip (919) to achieve the desired discrete positions for tip (919) will be apparent to those of ordinary skill in the art.

Another consideration with tip (919) in terms of configuring the discrete positions relates to the proximal portions of arms (927) that ultimately engage with pin (929). More specifically, the degree of the freedom of movement of the proximal portions of arms (927) with respect to the pin (929) influence the positions that internal clip (921) will adopt when changing from a first discrete position to a second discrete position. For instance, when internal clip (921) snaps from one discrete position to another discrete position, bores (933) of arms (927) can travel along pin (929) to some extent. In one example, a larger travel length of bores (933) of arms (927) along pin (929) equates to a larger difference in position from the first discrete position to the second discrete position when internal clip (921) snaps from one to the other. Furthermore, with pin (929) within body (920) of anvil (918), body (920) can be configured to allow greater or lesser freedom of movement of bores (933) along pin (929) depending on the space available for bores (933) to travel along pin (929). Similarly, having the connection of arms (927) within body (920) of anvil (918), instead of within elastomeric overmold (923), can promote greater freedom of movement of arms (927) along pin (929). Also, the diameter of pin (929) can influence the friction between pin (929) and bores (933) and thus freedom of movement of arms (927) relative to pin (929).

Referring to FIG. 32, another feature that contributes to controlling the lateral movement of arms (927), and hence the discrete positions adopted by tip (919), is geometry of the slot within body (920) of anvil (918). For example, in the illustrated version, anvil (918) comprises slot (935) within body (920) where slot (935) is defined as the space between two walls (937) extending within body (920). As shown, the proximal portion of arms (927) are moved close enough to one another to fit within slot (935) and ultimately connect with pin (929). With this configuration, the dimensions of slot (935) defined by walls (937) acts to limit the lateral movement ability of arms (927). This limited lateral movement impacts the degree of change in position when internal clip (921) snaps from its first discrete position to its second discrete position. Thus, altering the width of slot (935) can provide another way to control the range of motion of internal clip (921). Additionally, the height of slot (935) can influence the range of motion arms (927) have to travel along pin (929). For instance, a small height may be more restrictive and thereby impede arms (927) from traveling along pin (929) when tip (919) moves from the first discrete position to the second discrete position. Similarly, a larger height may be less restrictive and allow arms (927) to travel further along pin (929) when tip (919) is toggled.

3. Elastomeric Tip Incorporating a Cut-Out Window

Figure 33:
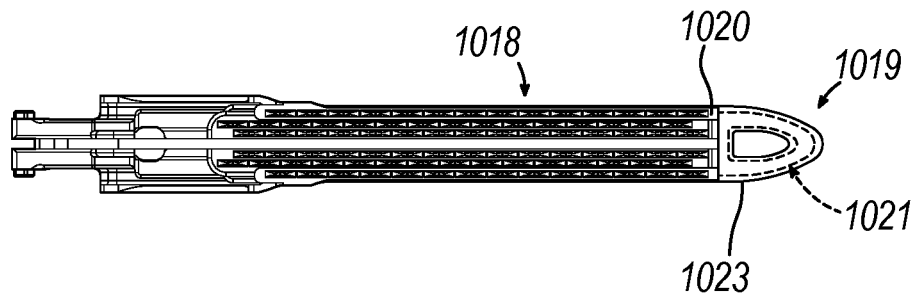
FIG. 33 depicts bottom view of an alternate anvil of an end effector for use with the surgical instruments described herein.
Figure 34:
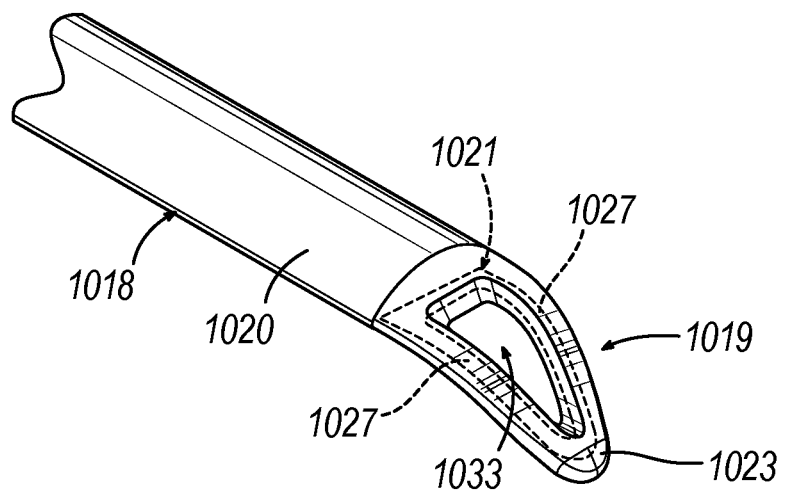
FIG. 34 depicts an enlarged perspective view of a tip of the anvil of FIG. 33, showing the tip in a first position.
Figure 35:
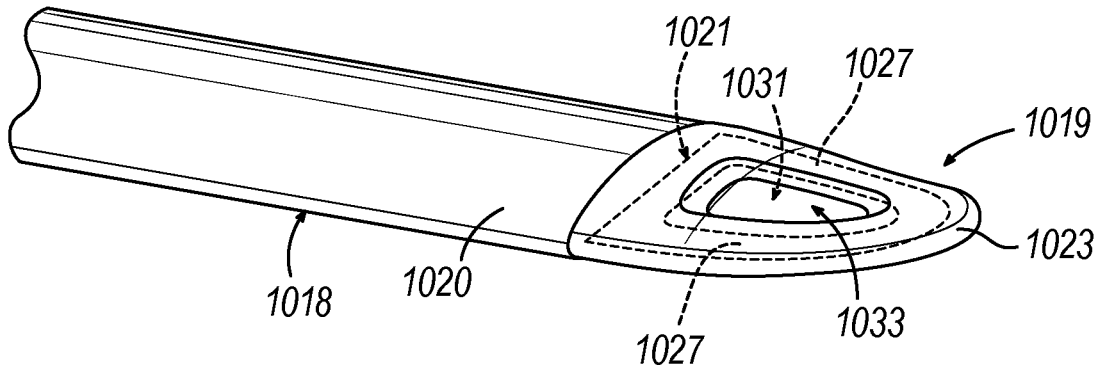
FIG. 35 depicts an enlarged perspective view of a tip of the anvil of FIG. 33, showing the tip in a second position.

FIGS. 33-35 depict an exemplary anvil (1018) that is usable with the end effectors described herein and others. For instance, anvil (1018) can be interchanged or used in place of anvils (18, 218, 318) of respective end effectors (12, 212, 312, 412) described above. It will be appreciated that end effectors (12, 212, 312, 412) incorporating anvil (1018) may be used with instruments (10, 310) and the other surgical instruments described herein. To this extent, end effectors (12, 212, 312, 412) incorporating anvil (1018) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvil (1018) is operable to pivot relative to lower jaws (16, 216). Anvil (618) and lower jaws (16, 216) may clamp tissue (90) similarly to clamping performed by anvil (18) and lower jaw (16) shown in FIG. 7. Anvil (1018) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating anvil (1018) further comprises a cartridge (37, 237) containing staples where cartridge (37, 237) is operable to be placed in lower jaw (16, 216).

Still referring to FIGS. 33-35, anvil (1018) comprises body (1020) and tip (1019). Tip (1019) connects with and extends distally from body (1020). Tip (1019) comprises a support structure (shown as internal clip (1021) in phantom), and a polymeric or metallic covering (shown as an elastomeric overmold (1023)). As with prior anvil tips, tip (1019) is configured such that internal clip (1021) can be toggled from a first discrete position having an angled orientation as shown in FIG. 34, to a second discrete position having a straight orientation as shown in FIG. 35 by applying an external input force.

Internal clip (1021) comprises arms (1027) and a space (1031) between arms (1027). Furthermore, elastomeric overmold (1023) comprises an opening (1033) extending though tip (1019). Opening (1033) aligns with space (1031) of internal clip (1021). By altering the size and shape of opening (1033) as well as space (1031), the deflection of tip (1019) to discrete positions can be controlled to achieve desired curved and straight or flared orientations. In view of the teachings herein, other ways to control the discrete positions of internal clip (1021) will be apparent to those of ordinary skill in the art.

4. Internal Clip with Central Deflecting Rib

Figure 36:
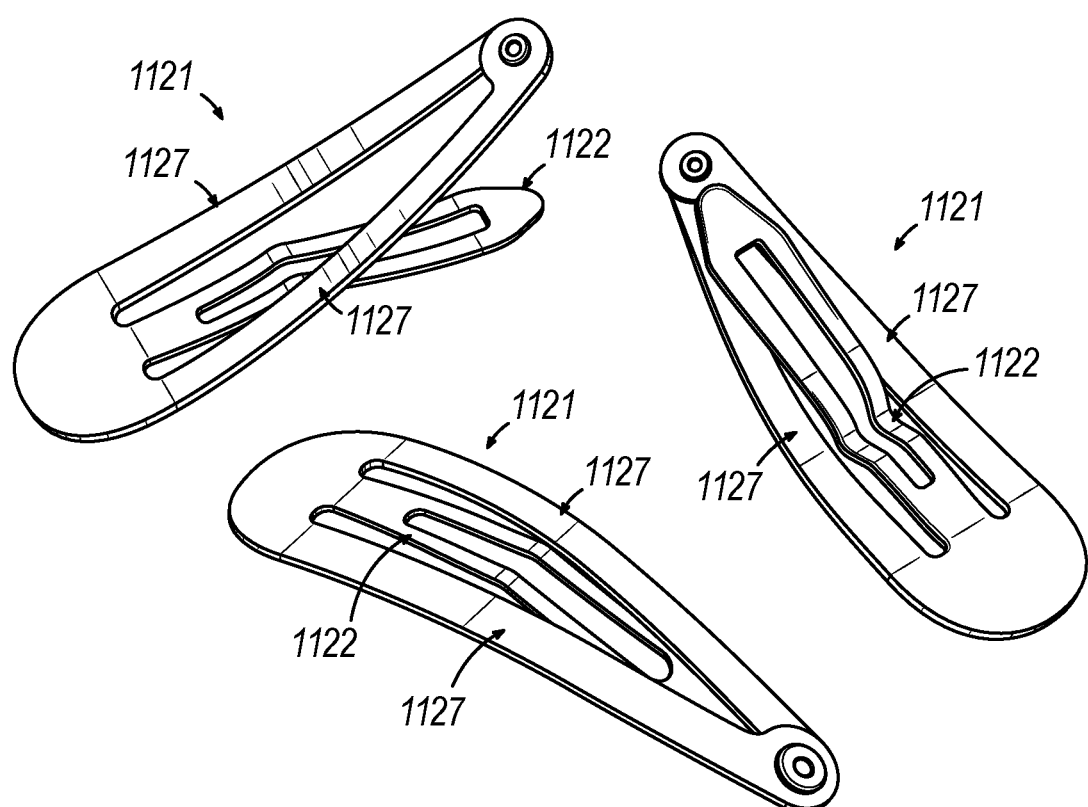
FIG. 36 depicts a plurality of alternate internal clips, each internal clip being usable within a tip of an anvil of an end effector for use with the surgical instruments described herein.

FIG. 36 illustrates a plurality of alternate internal clips (1121), each internal clip (1121) being usable within a tip of an anvil of an end effector for use with the surgical instruments described herein. For instance, internal clips (1121) may be used in place of internal clips (821, 921, 1021). Internal clips (1121) comprise a resilient middle rib (1122)

that extends longitudinally between a pair of arms (1127) of internal clip (1121). Middle rib (1122) is deflectable and comprises a bias to adopt discrete positions. In the present example, internal clip (1121) is configured as a barrette style clip. As described above, where internal clip (1121) replaces internal clip (821, 921, 1021), internal clip (1121) may be overmolded with an elastomeric overmold as described above. Additionally, in view of the teachings herein various ways to control the discrete positions of internal clip (1121) to thereby control discrete positions of a tip using internal clip (1121) will be apparent to those of ordinary skill in the art.

E. Exemplary Elastomeric Overmold Configurations

With respect to anvil tips described above that incorporate an elastomeric overmold, various attributes of the elastomeric overmold can be configured to provide for various functional parameters. Moreover, as stated above, the elastomeric overmold may work in conjunction with certain internal clips, pivot members, or other internal features as a system or assembly to provide for multiple discrete tip positions. The tip can be toggled or adjusted between these discrete positions by applying an external force, i.e., by the user, the user's hand tool, a robotic manipulator, or the patient's anatomy. In this manner, modifications to the various configurations and designs of the elastomeric overmold can impact the ease or difficulty of moving or toggling a tip from one discrete position to another. As already mentioned above, one example of this involves using elastomers of varying stiffness. And another example of this mentioned above involves changing the elastomer mass and/or geometry, e.g., by including an opening such as opening (1033) described above.

Still, there are other considerations and ways to configure the elastomeric overmold to work with internal clips and/or pivot members to provide a desired range of tip functionality. In one version, the tips described herein include elastomeric overmolds, the overmold may surround all structures of the tip, and may bond to all structures of the tip. However, in other versions of the tips described herein with elastomeric overmolds, the overmold is configured to not surround and/or bond to all structures of the tip. Below are some further exemplary configurations for the elastomeric overmold of the tips. These configurations, among others, can apply to any of the tips having elastomeric overmolds described herein, which include at least tips (219, 319, 619, 719, 819, 919, 1019) and at least elastomeric overmolds (623, 723, 823, 923, 1023).

In one example, elastomeric overmold (623, 723, 823, 923, 1023) of tip (219, 319, 619, 719, 819, 919, 1019) is bonded directly to anvil (218, 318, 618, 718, 818, 918, 1018), or directly to an intermediate connector such as connection member (621, 721) so that it forms a contiguous smooth surface, free of openings or gaps when the tip is deformed. In such an example, bonding to certain locations allows the elastomer to be have a spring bias and act as a spring and thus source of the tension that could aid in providing the tip with discrete positions.

In another example, elastomeric overmold (623, 723, 823, 923, 1023) of tip (219, 319, 619, 719, 819, 919, 1019) can be specifically blocked from being bonded to certain locations. By way of example only, and not limitation, with tips having pivot member (625, 725) or internal clip (821, 921, 1021, 1121), bonding of elastomeric overmold (623, 723, 823, 923, 1023) is partially or completely blocked such that pivot member (625, 725) or internal clip (821, 921, 1021, 1121) is not bonded to elastomeric overmold (623, 723, 823, 923, 1023). In this manner, the dynamics of the toggle can be varied by allowing relative slip between pivot member (625, 725) or internal clip (821, 921, 1021, 1121), and elastomeric overmold (623, 723, 823, 923, 1023). For instance, one way to block bonding in this manner is to dip pivot member (625, 725) or internal clip (821, 921, 1021, 1121) in wax or another coating, so that the elastomer does not bond to it, thereby allowing relative slip.

Referring to FIGS. 17 and 26, pivot member (625) comprises coating (628), and internal clip (821) comprises coating (828). In the present example, coatings (628, 828) comprise a wax, but other coating materials may be used. Also, coatings (628, 828) can be applied to the entirety of pivot member (625) and internal clip (821) in some versions. However, in other versions coating (628, 828) can be applied to portions of pivot member (625) and internal clip (821). For instance, with respect to internal clip (821), in one example coating (828) is applied to pair of arms (827) only. Still yet, coatings (628, 828) are omitted entirely in other examples of pivot member (625) and internal clip (821). In view of the teachings herein, other ways to block bonding of the elastomeric overmold to certain structures of the tip will be apparent to those of ordinary skill in the art.

In another example, elastomeric overmold (623, 723, 823, 923, 1023) of tip (219, 319, 619, 719, 819, 919, 1019) some portions of the pivot member (625, 725) or internal clip (821, 921, 1021, 1121) may not be covered with the elastomeric material at all. In such an example, this represents an opportunity to slim down or reduce the size of the tip and to allow pivot member (625, 725) or internal clip (821, 921, 1021, 1121) to have a more powerful or stronger detenting toggle. By way of example only, and not limitation, in one version a base or proximal portion of tip (619, 719, 819, 919, 1019) is covered, while the raw or partially raw pivot member (625, 725) or internal clip (821, 921, 1021, 1121) extends distally. As used herein, the terms "raw" or "partially raw" here shall be understood to mean that such portion of pivot member (625, 725) or internal clip (821, 921, 1021, 1121) is uncovered by elastomeric overmold or otherwise exposed to the surrounding environment.

F. Exemplary Toggling or Detenting Mechanism

With respect to internal clips (821, 921, 1021, 1121), in one example such internal clips (821, 921, 1021, 1121) are described as configured with a barrette design so that internal clips (821, 921, 1021, 1121) contain elastic energy after they are riveted. In this manner internal clips (821, 921, 1021, 1121) can have stored elastic energy. After assembly and connected with the body of the anvil, an external force is applied. For example, this external force may be applied by the user, the user's hand tool, a robotic manipulator, or the patient's anatomy. During this external force application, the arms of internal clips (821, 921, 1021, 1121) undergo elastic deformation and reactive force builds until it reaches a state instability. If the force continues in the same direction, the arms of internal clips (821, 921, 1021, 1121) will pass over or through the instability zone to another lower energy state. Thus, in this manner, internal clips (821, 921, 1021, 1121) are comprised with bistability in some cases, and even multi-stability in other cases. With bistability, internal clips (821, 921, 1021, 1121) comprise two positions with low energy states where internal clips (821, 921, 1021, 1121) will maintain their shape and position absent an external force being applied thereto. With multi-stability, internal clips (821, 921, 1021, 1121) comprises more than two positions with low energy states where internal clips (821, 921, 1021, 1121) will maintain their shape and position absent an external force being applied thereto. In some examples of bistability and multi-stability, internal clips (821, 921, 1021, 1121) can be described as comprising the ability to twist, bend, or buckle from one state or position to another. In view of the teachings herein, various ways to modify and control the stability and positioning of internal clips (821, 921, 1021, 1121) will be apparent to those of ordinary skill in the art.

G. Exemplary Anvil with Swiveling Tip

In some instances, it may be desirable to provide the anvil of a surgical stapler end effector with a selectively adjustable distal tip that is configured to transition between first and second discrete positions via rotation about a longitudinal axis. Such configurations may provide different benefits than other configurations in which the distal trip transitions between first and second discrete positions via upward and downward pivoting about a lateral axis as described above in connection with FIGS. 13-20, or via flexion as described above in connection with FIGS. 21-36. Advantageously, in such versions the anvil tip may be configured with a rigid construction, an elastically deformable construction, or any suitable combination thereof while still be selectively transitionable between first and second discrete positions exhibiting the advantages described above. Furthermore, in some instances, it may be desirable to rotatably couple the anvil tip with the anvil body such that the tip is rotatable about an axis that extends in a vertical plane containing the longitudinal axes of the anvil body and the opposing lower jaw of the end effector. In such versions, the anvil tip is said to rotatably "swivel" relative to the anvil body between the first and second discrete positions.

FIGS. 37-45 depict exemplary anvils (1218, 1318, 1418, 1518, 1618, 1718, 1818) having distal tips (1222, 1322, 1422, 1522, 1622, 1722, 1822) that are selectively rotatable relative to the respective anvil body in such a manner that the tip (1222, 1322, 1422, 1522, 1622, 1722, 1822) is configured to swivel relative to the anvil body between first and second discrete positions. Anvils (1218, 1318, 1418, 1518, 1618, 1718, 1818) and their respective end effectors described below may be interchanged with any of the exemplary anvils (18, 218, 318, 518, 618, 718, 818, 918, 1018) and end effectors (12, 212, 312, 412, 812, 912) described above, and may be used with surgical instruments (10, 310) and other exemplary surgical instruments described herein. It will be understood that anvils (1218, 1318, 1418, 1518, 1618, 1718, 1818) are similar to anvils (18, 218, 318, 518, 618, 718, 818, 918, 1018) described above in that anvils (1218, 1318, 1418, 1518, 1618, 1718, 1818) are operable to clamp tissue (90) against a staple cartridge supported within the lower jaw of a corresponding end effector, such as staple cartridge (37) supported within lower jaw (16) described above, and are further operable to form staples ejected by the staple cartridge into the clamped tissue. As described below, anvils (1218, 1318, 1418, 1518, 1618, 1718, 1818) may be provided with a tip locking mechanism operable to releasably retain the anvil tip within the discrete positions and thereby protect against inadvertent rotation of the anvil tip out of a discrete position.

It will be appreciated that any of the exemplary anvil tips (1222, 1322, 1422, 1522, 1622, 1722, 1822) described below may be formed of one or more materials as desired, which may include rigid materials, elastically deformable materials, or combinations thereof. For instance, in some versions an anvil tip (1222) may be include a core or proximal base portion formed of a rigid material such as a metal, and an elastomeric body portion coupled to or otherwise overmolded about the rigid core or proximal base portion.

1. Overview of Exemplary Anvil with Swiveling Tip

Figure 37:
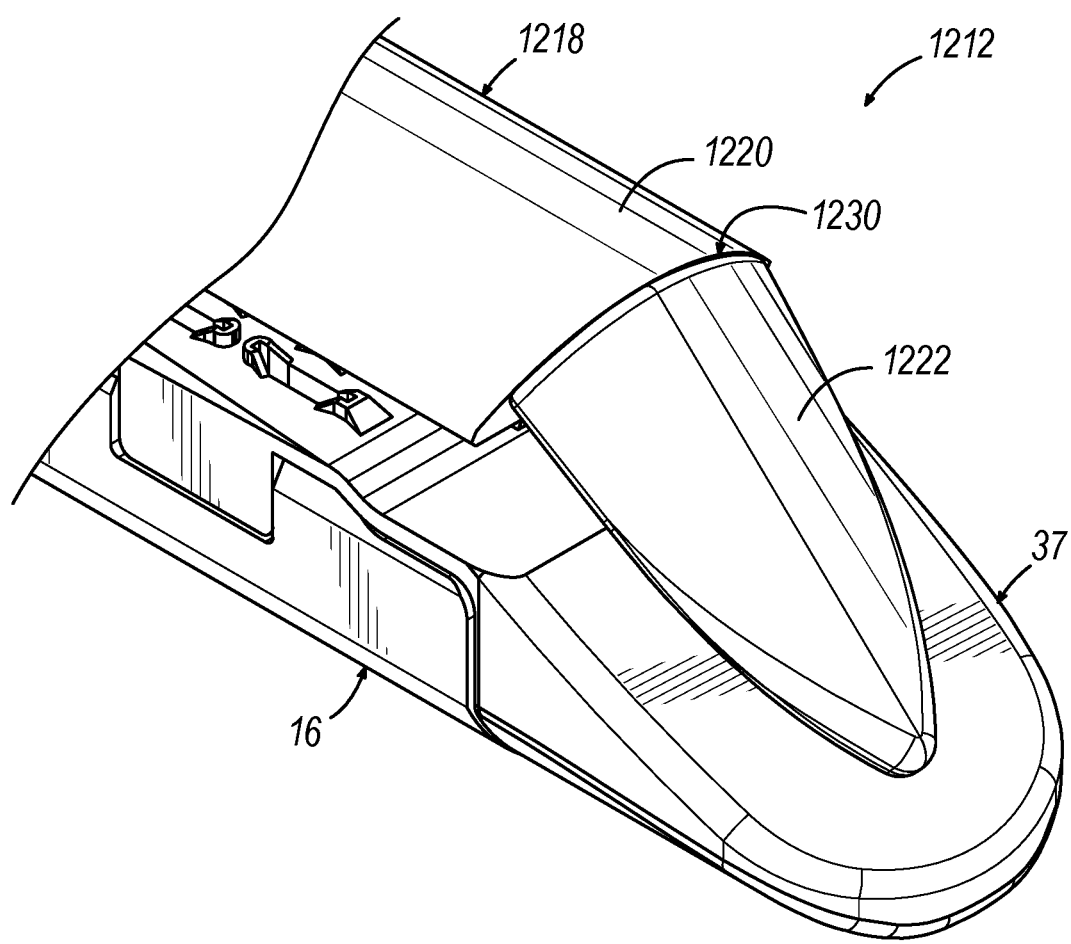
FIG. 37 depicts a perspective view of a distal portion of another exemplary end effector having an anvil with a selectively rotatable distal tip, showing the distal tip in a first discrete position relative to an anvil body.
Figure 38:
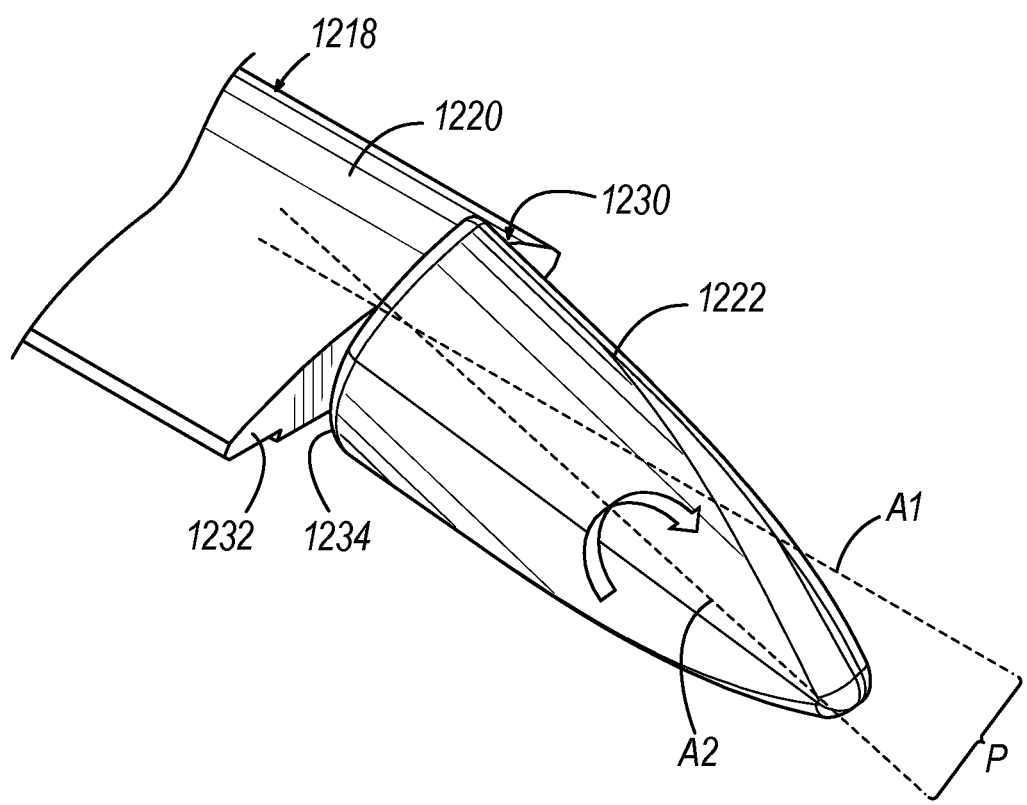
FIG. 38 depicts a perspective view of the body and the distal tip of the anvil of FIG. 37, showing the distal tip rotating relative to the body between the first discrete position and a second discrete position.
Figure 39A:
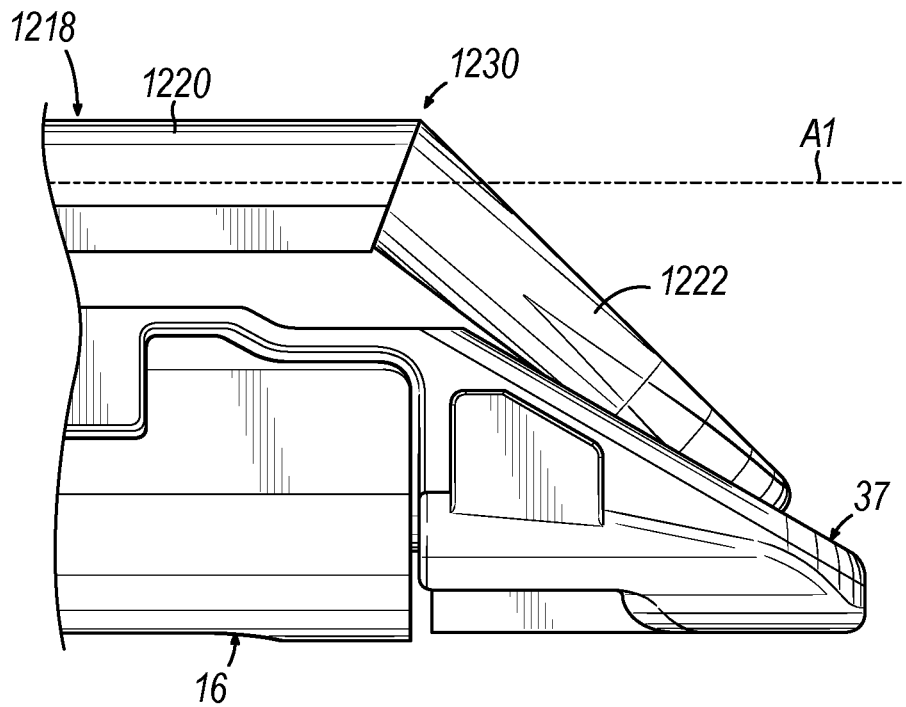
FIG. 39A depicts a side elevational view of a distal portion of the end effector of FIG. 37, showing the distal tip in the first discrete position relative to the body.
Figure 39B:
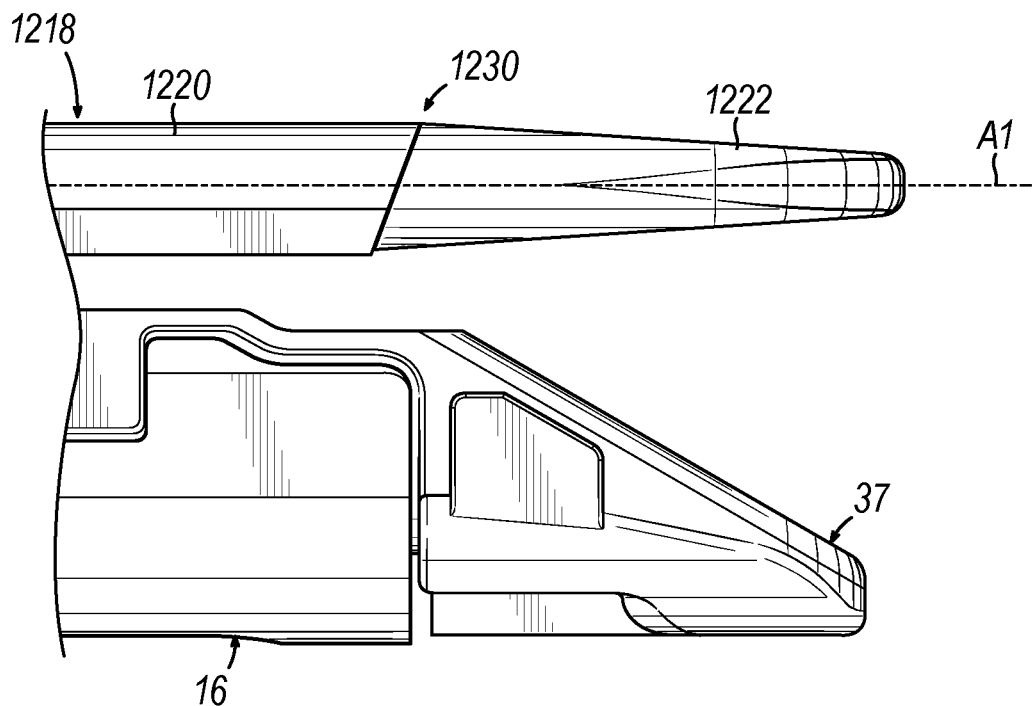
FIG. 39B depicts a side elevational view of a distal portion of the end effector of FIG. 37, showing the distal tip in the second discrete position relative to the body.

FIGS. 37-39B illustrate an exemplary end effector (1212) that includes an anvil (1218) pivotably coupled with lower jaw (16), and staple cartridge (37) positioned within lower jaw (16). Anvil (1218) includes an elongate anvil body (1220) having a plurality of staple forming pockets (not shown) similar to pockets (53) of anvil (18) arranged along a length thereof. A tapered distal anvil tip (1222) is rotatably coupled to a distal end of anvil body (1220), and is selectively rotatable relative to anvil body (1220) between first and second discrete positions in response to an external rotational force applied to tip (1222) by a user or by an adjacent anatomical structure. As shown in FIGS. 37 and 39A, anvil tip (1222) in the first discrete position is angled relative to anvil body (1220) such that a distal end of anvil tip (1222) extends toward staple cartridge (37) and is configured to contact a distal end of staple cartridge (37) when anvil (1218) is closed to clamp tissue therebetween. As shown in FIG. 39B, anvil tip (1222) in the second discrete position is oriented straight relative to anvil body (1220) such that when end effector (1212) is in the closed state, anvil tip (1222) extends generally parallel to lower jaw (16) and staple cartridge (37), and the distal end of anvil tip (1222) is thus spaced apart from the distal end of staple cartridge (37) to define a gap therebetween. Thus, anvil tip (1222) in the straight position is configured to provide end effector (1212) with a distally opening aperture throughout its clamping range that is larger than a corresponding aperture exhibited by end effector (1212) when anvil tip (1222) is in angled position. Accordingly, similar to other exemplary versions described above, anvil tip (1222) in the angled position is suitably oriented to draw tissue proximally between anvil (1218) and staple cartridge (37) and to facilitate visualization of the target tissue during closure of end effector (1212). Additionally, anvil tip (1222) in the straight position is suitably oriented to facilitate marching during a stapling procedure, as also described above. A user may thus select the angled position or the straight position of anvil tip (1222) as desired to best facilitate a particular procedure being performed.

As shown in FIG. 38, anvil body (1220) extends along a longitudinal body axis (A1), and anvil tip (1222) is configured to rotate about a rotational axis (A2) that intersects and is obliquely angled relative to body axis (A1) while still extending in a generally proximal-to-distal direction. Axes (A1, A2) thus define and are contained by a vertical plane (P) that extends along a longitudinal centerline of end effector (1212), so as to also contain a longitudinal axis (not shown) of lower jaw (16). In other words, each axis (A1, A2) extends within and along vertical plane (P). The rotational axis (A2) of anvil tip (1222) is defined by a rotary member (not shown), which may be in the form of a shaft similar to any of shafts (1324, 1524, 1634, 1740) described below in connection with exemplary anvils (1318, 1518, 1618, 1718) of FIGS. 40-48. In the present version, the rotary member is suitably configured such that rotational axis (A2) extends obliquely to the longitudinal axis of anvil tip (1222).

As shown in FIGS. 38-39B, anvil (1218) includes an angled interface (1230) defined by an angled distal face (1232) of anvil body (1220) and an angled proximal face (1234) of anvil tip (1222). Angled faces (1232, 1234) are configured to engage one another in first and second mating configurations to define the first and second discrete positions of anvil tip (1222). As shown in FIGS. 39A and 39B, angled faces (1232, 1234) are obliquely angled relative to the longitudinal axes of anvil body (1220) and anvil tip (1222). As shown in FIG. 39A, the oblique angles of angled interface (1230) are summated when anvil tip (1222) is in the first rotational orientation relative to anvil body (1220), thus orienting the longitudinal axis of anvil tip (1222) obliquely relative to the longitudinal axis (A1) of anvil body (1220) to provide anvil tip (1222) in the angled position. The anvil tip (1222) includes first and second opposing surfaces (1236, 1238) that are shown as being generally arcuate. In the first rotational orientation of FIG. 23A, first surface (1236) is the outer surface, and first surface (1238) is the inner surface relative to staple cartridge (37).

The second rotational orientation may be obtained by rotating anvil tip (1222) 180-degrees relative to the first rotational orientation. As shown in FIG. 39B, the oblique angles of angled interface (1230) are configured to negate one another when anvil tip (1222) is in the second rotational orientation relative to anvil body (1220), thus aligning the longitudinal axes of anvil body (1220) and anvil tip (1222) coaxially such that anvil tip (1222) extends distally straight from anvil body (1220). In other words, angled faces (1232, 1234) are oriented relative to one another in the second discrete position, shown in FIG. 39B, such that angled faces (1232, 1234) define supplementary angles that together define a 180-degree angle. In other versions, angled faces (1232, 1234) could be alternatively configured to define an angle of greater than 180 degrees when anvil tip (1222) is in the second discrete position. In such versions, anvil tip (1222) in the second discrete position would flare upwardly away from the distal end of staple cartridge (37) and anvil body axis (A1), for example similar to the configuration described above in connection with anvil (818) in FIG. 29. In the second rotational orientation of FIG. 23B, second surface (1238) is the outer surface, and first surface (1236) is the inner surface relative to staple cartridge (37).

Though not shown, anvil (1218) may further include a tip locking mechanism operable to releasably retain anvil tip (1222) in the first and second discrete positions, and thus prevent inadvertent rotation of tip (1222) away from a selected position. Such a tip locking mechanism may comprise one or more detent features, protrusions, recesses, resilient members, interference features, and the like of various types that will be readily apparent to those of ordinary skill in the art in view of the teachings herein. For instance, anvil (1218) may include any one or more of the exemplary tip locking mechanisms described below in connection with anvils (1318, 1418, 1518, 1618, 1718, 1818), such as detent protrusions (1340) and detent recesses (1342). Additionally, though not shown, anvil (1218) may further include a connection member rigidly secured to a distal end of anvil body (1220) and to which anvil tip (1222) is rotatably coupled. Such a connection member may be similar to any of the exemplary connection members (1330, 1430, 1530, 1630, 1730, 1830) described below. Moreover, anvil tip (1222) may be secured axially relative to anvil body (1220) using any of the exemplary methods described below.

2. Anvil with Swiveling Tip Having Tip Locking Mechanism with Detent Bumps

Figure 40:
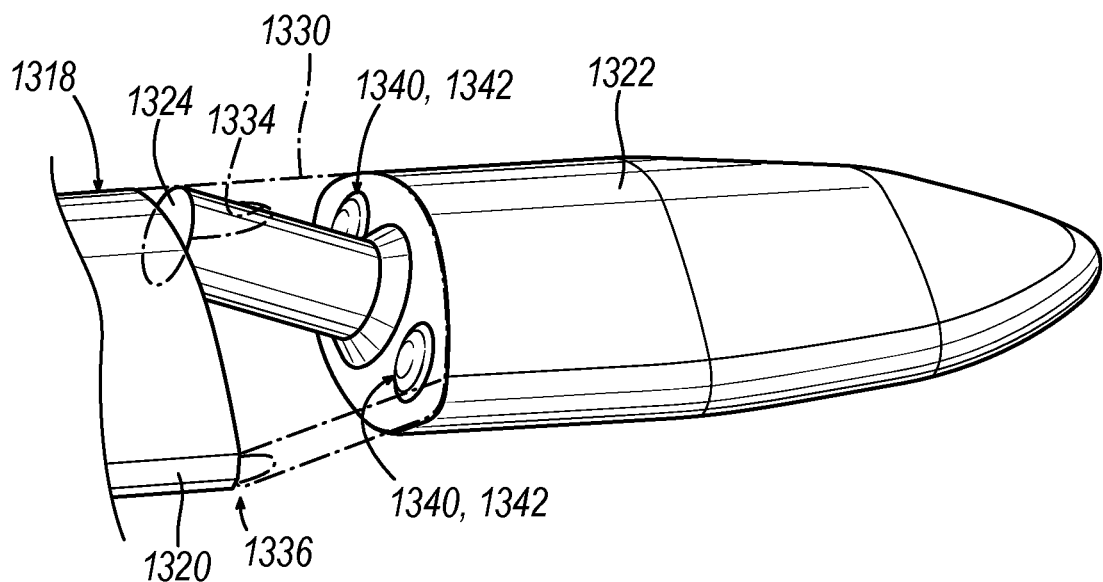
FIG. 40 depicts a perspective view of a distal portion of another exemplary anvil having a body, a selectively rotatable distal tip, and a tip locking mechanism, showing the distal tip in a pre-finalized state of assembly and in a second discrete position relative to the body.
Figure 41:
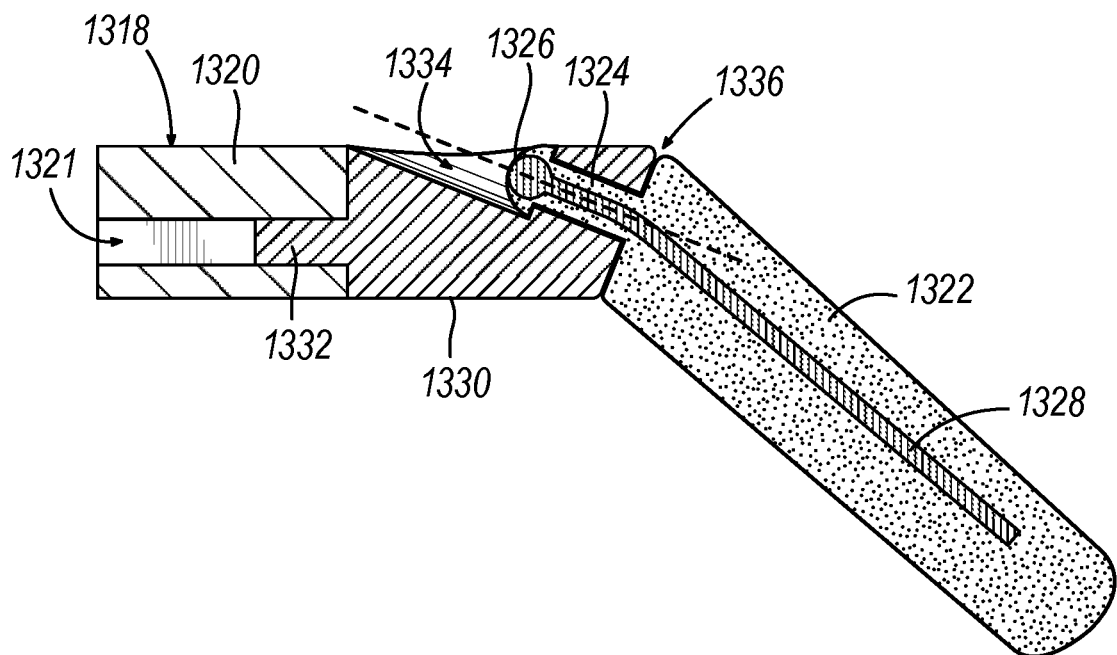
FIG. 41 depicts a side sectional view of the distal portion of the anvil of FIG. 40, showing the distal tip in a finalized state of assembly and in a first discrete position relative to the body.

FIGS. 40-41 illustrate a distal portion of another exemplary anvil (1318) suitable for use with any of the exemplary end effectors described above. Anvil (1318) is similar to anvil (1218) described above except as otherwise described below. Like anvil (1218), anvil (1318) includes an elongate anvil body (1320) having a plurality of staple forming pockets (not shown) arranged along an underside thereof, and a tapered distal tip (1322) rotatably disposed at a distal end of anvil body (1320). Like anvil tip (1222), anvil tip (1322) is configured to swivel relative to anvil body (1320) about a rotational axis disposed within a plane that contains the longitudinal axis of anvil body (1320) and a longitudinal centerline of a corresponding end effector having lower jaw (16). In particular, anvil tip (1322) is configured to swivel about the rotational axis between a first discrete position in which anvil tip (1322) is angled relative to anvil body (1320) in a direction toward lower jaw (16), and a second discrete position in which anvil tip (1322) extends distally straight from anvil body (1320) so as to be oriented away from lower jaw (16).

Anvil (1318) further includes a connection member (1330) that is rigidly secured to a distal end of anvil body (1320) and rotatably supports anvil tip (1322). As seen in FIG. 41, connection member (1330) includes a proximal plug (1332) that is securely received (e.g., via an interference fit) within an open distal end of a longitudinal anvil slot (1321) of anvil body (1320), which may be similar to longitudinal anvil slot (42) of anvil (18) described above. Connection member (1330) further includes an internal bore (1334) that extends obliquely to a longitudinal axis of anvil body (1320) and connection member (1330), and is configured to rotatably receive a proximally extending shaft (1324) of anvil tip (1322). Shaft (1324) may be formed integrally with a body of anvil tip (1322) and extends obliquely to a longitudinal axis thereof. Bore (1334) and shaft (1324) cooperate to define a rotational axis (A2) of anvil tip (1322) that is obliquely angled relative to the longitudinal axes of anvil body (1320) and anvil tip (1322). Anvil tip (1322) and connection member (1330) include angled end faces that adjustably mate with one another to define an angled interface (1336) that provides for the angled and straight orientations of anvil tip (1322) relative to anvil body (1320) in the first and second discrete positions, similar to angled interface (1230) of anvil (1218) described above.

A proximal end of shaft (1324) of anvil tip of anvil tip (1322) of the present version includes a retention feature (1326) configured to engage an internal shoulder of bore (1334) and thereby retain shaft (1324) axially within bore (1334) while still permitting shaft (1324) to rotate therein to enable rotation of anvil tip (1322) between the straight and angled positions. Retention feature (1326) of the present example is shown in FIG. 41 the form of a rounded protrusion, which may be formed through deformation (e.g., thermal deformation, or "heat staking") of the proximal end of shaft (1324) following its insertion into bore (1334) during initial assembly of anvil (1318). In that regard, FIG. 40 shows anvil (1318) in a pre-finalized state of assembly prior to the formation of rounded protrusion (1326), and FIG. 41 shows anvil (1318) in a finalized state of assembly following deformation of rounded protrusion (1326). Various other suitable types of retention features that may be provided integrally with or independently from shaft (1324) will be readily apparent to those of ordinary skill in the art in view of the teachings herein.

As shown in FIG. 41, anvil tip (1322) of the present example further includes an optional stiffening member (1328) embedded therein and which extends proximally through shaft (1324) and distally through a least a portion of a body of anvil tip (1322). Stiffening member (1328) may be formed of a material having greater rigidity than the body of anvil tip (1322), such that a distal-most portion of anvil tip (1322) through which stiffening member (1328) does not extend has greater flexibility that a proximal portion of anvil tip (1322), including shaft (1324). In some versions, the body of anvil tip (1322) may be formed of a flexible elastomeric material while stiffening member (1328) is formed of a more rigid material, which may be bendable. In some versions, the material of stiffening member (1328)

may compatible with magnetic resonance imaging (MRI) devices, and/or may be configured to serve as a marker for fluoroscopic identification. In the present version, a proximal end of stiffening member (1328) joins within an inner core element of retention feature (1326), thus enabling retention feature (1326) to maintain its engagement with the inner shoulder of bore (1334) when an axial load is exerted on shaft (1324), for instance during swiveling of anvil tip (1322).

As shown best in FIG. 40, anvil (1318) further includes a tip locking mechanism configured to releasably retain anvil tip (1322) in the first and second discrete positions. The tip locking mechanism of the present example is shown in the form of detent features provided at angled interface (1336) of anvil tip (1322) and connection member (1330). In particular, a pair of detent protrusions (1340) is provided on the angled proximal face of anvil tip (1322), and a corresponding pair of detent recesses (1342) is provided in the angled distal face of connection member (1330). Detent protrusions (1340) are configured to fully seat within detent recesses (1342) when anvil tip (1322) is in either of the first or second discrete positions. Detent protrusions (1340) and/or shaft (1324) may resiliently deform as anvil tip (1322) is rotated between the discrete positions to permit detent protrusions (1340) to temporarily disengage detent recesses (1342). Upon anvil tip (1322) reaching one of the first or second discrete positions relative to anvil body (1320), detent protrusions (1340) then snap back into respective detent recesses (1342), thus providing the user with tactile confirmation that anvil tip (1322) has fully assumed the selected tip position. In place of or in addition to detent protrusions (1340) and/or detent recesses (1342), anvil (1318) may include various other suitable types of tip locking mechanisms, such as those described below.

3. Anvil with Swiveling Tip Having Tip Locking Mechanism with Detent Arms

Figure 42:
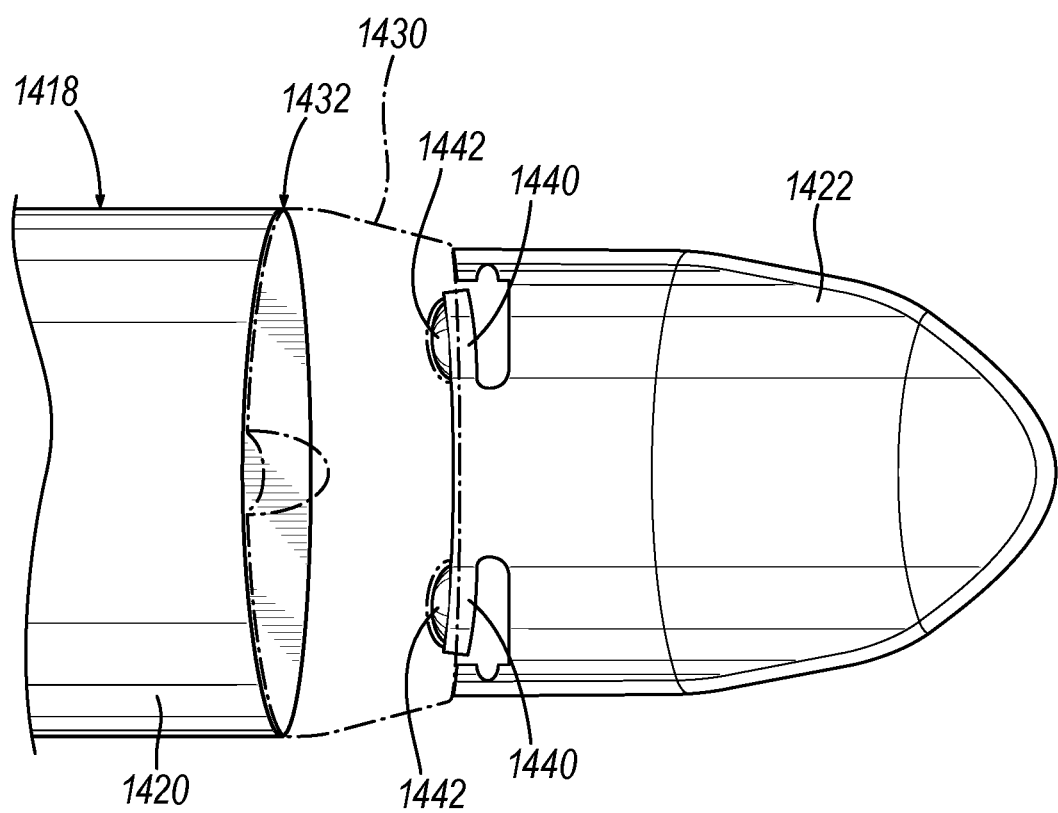
FIG. 42 depicts a top plan view of a distal portion of another exemplary anvil having a body, a selectively rotatable distal tip, and a tip locking mechanism, showing the distal tip in a first discrete position relative to the body.

FIG. 42 shows a distal portion of another exemplary anvil (1418) suitable for use with any of the exemplary end effectors described above. Anvil (1418) is similar to anvil (1318) described above except as otherwise described below. Like anvil (1318), anvil (1418) includes an elongate anvil body (1420) having a plurality of staple forming pockets (not shown) arranged along an underside thereof, a connection member (1430) secured to a distal end of anvil body (1420), and a tapered distal tip (1422) rotatably coupled to connection member (1430). Like anvil tip (1322), anvil tip (1422) is configured to swivel relative to connection member (1430) and anvil body (1420) about a rotational axis disposed within a plane that contains the longitudinal axis of anvil body (1420) and a longitudinal centerline of a corresponding end effector having lower jaw (16). In particular, anvil tip (1422) is configured to swivel about the rotational axis between a first discrete position in which anvil tip (1422) is angled relative to anvil body (1420) in a direction toward lower jaw (16), and a second discrete position in which anvil tip (1422) extends distally straight from anvil body (1420) so as to be oriented away from lower jaw (16). Connection member (1430) and anvil tip (1422) define an angled interface (1432) therebetween that provides for the angular reorientation of anvil tip (1322) relative to the longitudinal axis of anvil body (1420) during rotation of anvil tip (1422) between the first and second discrete positions.

Anvil (1418) of the present example further includes a tip locking mechanism disposed at angled interface (1432) and configured to releasably retain anvil tip (1422) in each of the first and second discrete positions relative to anvil body (1420). The present tip locking mechanism is shown in the form of a pair of resilient detent arms (1440) extending laterally from the angled proximal end of anvil tip (1422), and a corresponding pair of detent recesses (1442) disposed on the angled distal face of connection member (1430). Detent arms (1440) are configured to seat within detent recesses (1442) when anvil tip (1422) is in either of the first or second discrete positions. As anvil tip (1422) is rotated relative to anvil body (1420), detent arms (1440) resiliently deflect distally to thereby disengage detent recesses (1442). As anvil tip (1422) reaches one of the first or second discrete positions, detent arms (1440) snap back into respective detent recesses (1442), thus providing the user with tactile confirmation that anvil tip (1422) has fully assumed the selected tip position.

Figure 43A:
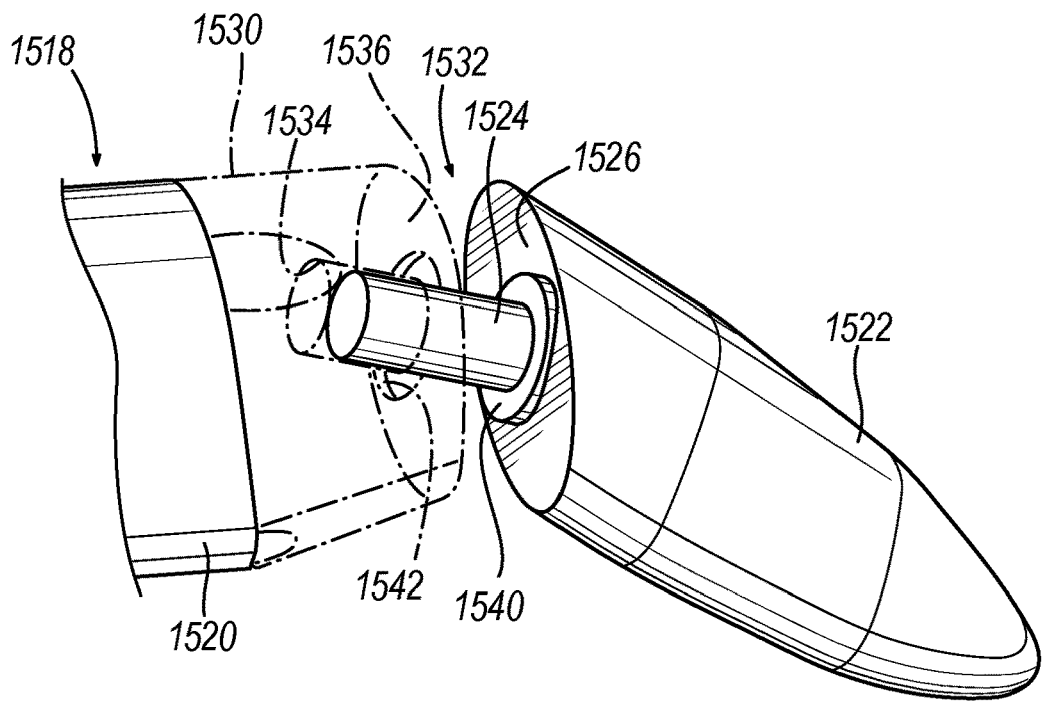
FIG. 43A depicts a perspective of a distal portion of another exemplary anvil having a body, a rotatable distal tip, and a tip locking mechanism, showing the distal tip partially decoupled from and in a second discrete position relative to the body.
Figure 43B:
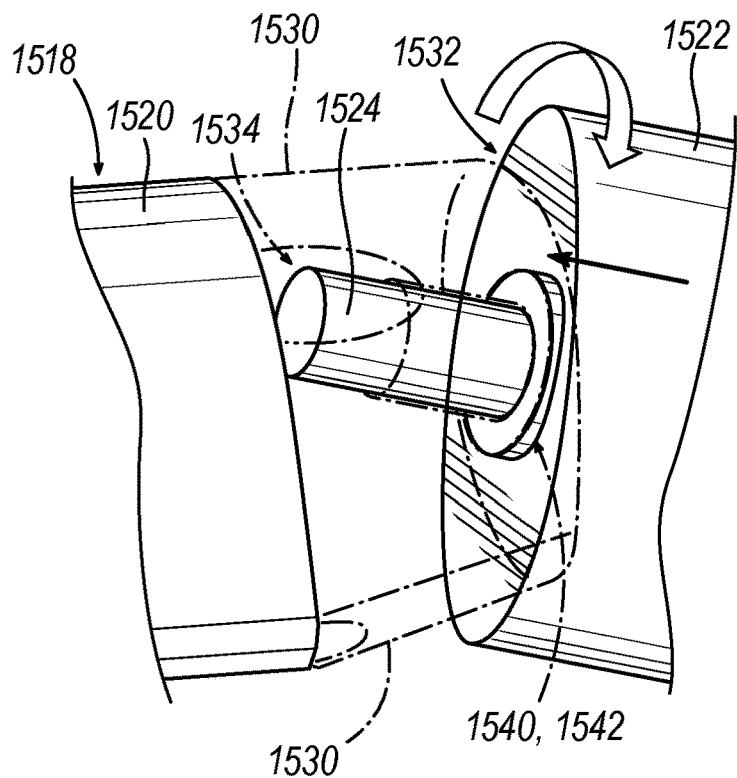
FIG. 43B depicts an enlarged perspective view of the distal portion of the anvil of FIG. 43A, showing the distal tip rotating relative to the body between a first discrete position and the second discrete position.

4. Anvil with Swiveling Tip Having Tip Locking Mechanism with Annular Wave Feature FIGS. 43A-43B show a distal portion of another exemplary anvil (1518) suitable for use with any of the exemplary end effectors described above. Anvil (1518) is similar to anvils (1318, 1418) described above except as otherwise described below. Like anvils (1318, 1418), anvil (1518) includes an elongate anvil body (1520) having a plurality of staple forming pockets (not shown) arranged along an underside thereof, a connection member (1530) secured to a distal end of anvil body (1520), and a tapered distal tip (1522) rotatably coupled to connection member (1530). Like anvil tips (1322, 1422), anvil tip (1522) is configured to swivel relative to connection member (1530) and anvil body (1520) about a rotational axis disposed within a plane that contains the longitudinal axis of anvil body (1520) and a longitudinal centerline of a corresponding end effector having lower jaw (16). In particular, anvil tip (1522) is configured to swivel about the rotational axis between a first discrete position in which anvil tip (1522) is angled relative to anvil body (1520) in a direction toward lower jaw (16), and a second discrete position in which anvil tip (1522) extends distally straight from anvil body (1520) so as to be oriented away from lower jaw (16). Connection member (1530) and anvil tip (1522) define an angled interface (1432) therebetween that provides for the angular reorientation of anvil tip (1522) relative to the longitudinal axis of anvil body (1520) during rotation of anvil tip (1522) between the first and second discrete positions.

Anvil (1518) of the present example further includes a tip locking mechanism disposed at angled interface (1532) and configured to releasably retain anvil tip (1522) in each of the first and second discrete positions relative to anvil body (1520). As shown best in the disassembled view of FIG. 43A, the present tip locking mechanism is shown in the form of an annular wave projection (1540) disposed at the base of shaft (1524) on an angled proximal face (1526) of anvil tip (1522); and a corresponding annular wave recess (1542) formed at the opening of bore (1534) on an angled distal face (1536) of connection member (1530). Though not shown, shaft (1524) may be retained axially within bore (1534) by a retention feature similar to rounded protrusion (1326) described above.

Axially raised portions of annular wave projection (1540) are configured to be received by corresponding axially recessed portions of annular wave recess (1542), and vice versa, when anvil tip (1522) is rotatably oriented in either the angled position shown in FIG. 43A or a straight position similar to that shown in FIG. 40. In any intermediate positions therebetween, raised portions of annular wave projection (1540) and of annular wave recess (1542) engage and drive axially against one another, thereby creating tension in shaft (1524). This resulting tension in shaft (1524) urges anvil tip (1522) rotationally toward the nearest straight or angled position, thus defining these positions as discrete positions.

Figure 44A:
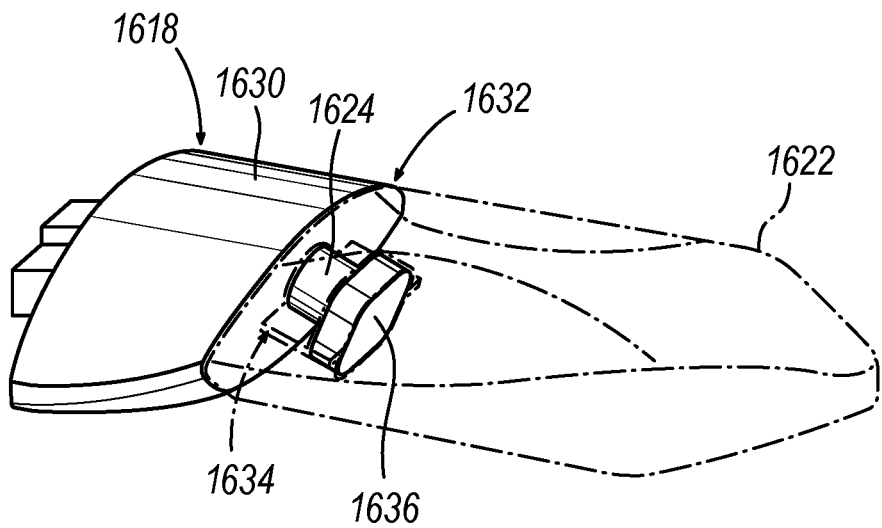
FIG. 44A depicts a perspective view of a distal portion of another exemplary anvil having a selectively rotatable distal and a tip locking mechanism, showing the distal tip in a second discrete position and in phantom to reveal features of the tip locking mechanism.
Figure 44B:
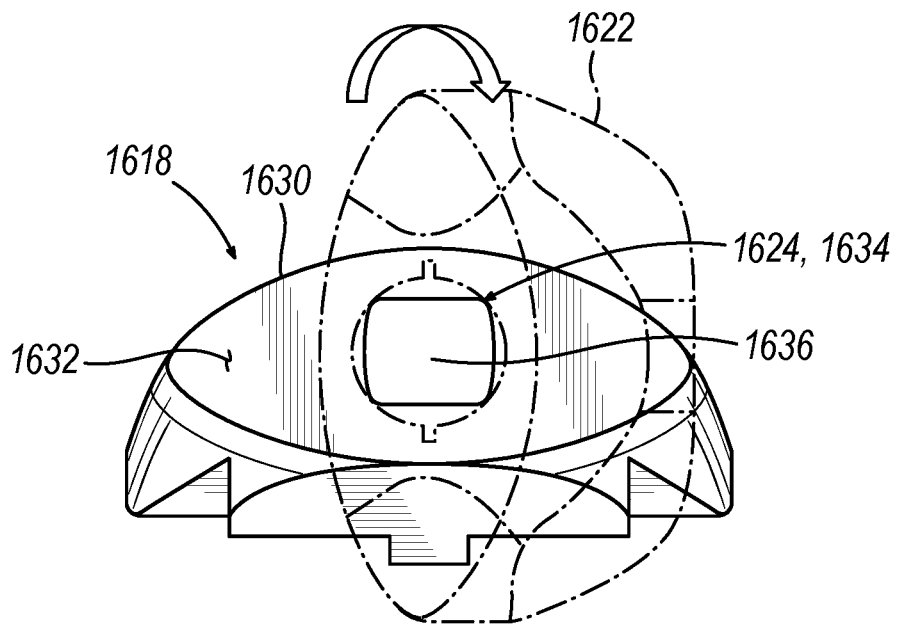
FIG. 44B depicts an end view of the distal portion of the anvil of FIG. 44A, showing the distal tip rotating relative to a connection member between the second discrete position and a first discrete position.

5. Anvil with Swiveling Tip Having Tip Locking Mechanism with Rotational Interference Feature FIGS. 44A-44B show a distal portion of another exemplary anvil (1618) suitable for use with any of the exemplary end effectors described above. Anvil (1618) is similar to anvils (1318, 1418, 1518) described above except as otherwise described below. Like anvils (1318, 1418, 1518), anvil (1618) includes an elongate anvil body (not shown) having a plurality of staple forming pockets arranged along an underside thereof, a connection member (1630) secured to a distal end of the anvil body, and a tapered distal tip (1622) rotatably coupled to connection member (1630). Like anvil tips (1322, 1422, 1522), anvil tip (1622) is configured to swivel relative to connection member (1630) about a rotational axis disposed within a plane that contains the longitudinal axis of the anvil body and a longitudinal centerline of a corresponding end effector having lower jaw (16). In particular, anvil tip (1622) is configured to swivel about the rotational axis between a first discrete position in which anvil tip (1622) is angled relative to the anvil body in a direction toward lower jaw (16), and a second discrete position in which anvil tip (1622) extends distally straight from the anvil body so as to be oriented away from lower jaw (16). Connection member (1630) and anvil tip (1622) define an angled interface (1632) therebetween that provides for the angular reorientation of anvil tip (1622) relative to the longitudinal axis of the anvil body during rotation of anvil tip (1622) between the first and second discrete positions.

In the present version, connection member (1630) includes a shaft (1634) that extends distally from an angled distal face thereof and is rotatably received within a corresponding bore (1624) formed within anvil tip (1622). Shaft (1634) and bore (1624) thus cooperate to define the axis about which anvil tip (1622) rotates relative to connection member (1630) between the first and second discrete positions. As shown best in FIG. 44A, shaft (1634) includes a cylindrical proximal portion and a distal cap (1636) having a non-circular cross-sectional shape. Shaft (1634) and bore (1624) also cooperate to define a tip locking mechanism configured to releasably retain anvil tip (1522) in each of the first and second discrete positions relative to connection member (1630). In particular, shaft cap (1636) and bore (1624) are suitably shaped to contact one another with an interference engagement when anvil tip (1622) is rotated between the angular and straight positions. This interference engagement results in resilient deflection of shaft cap (1636) and/or anvil tip (1622), which urges anvil tip (1622) toward the nearest straight or angled position.

6. Anvil with Swiveling Tip and Independent Captured Shaft

Figure 45:
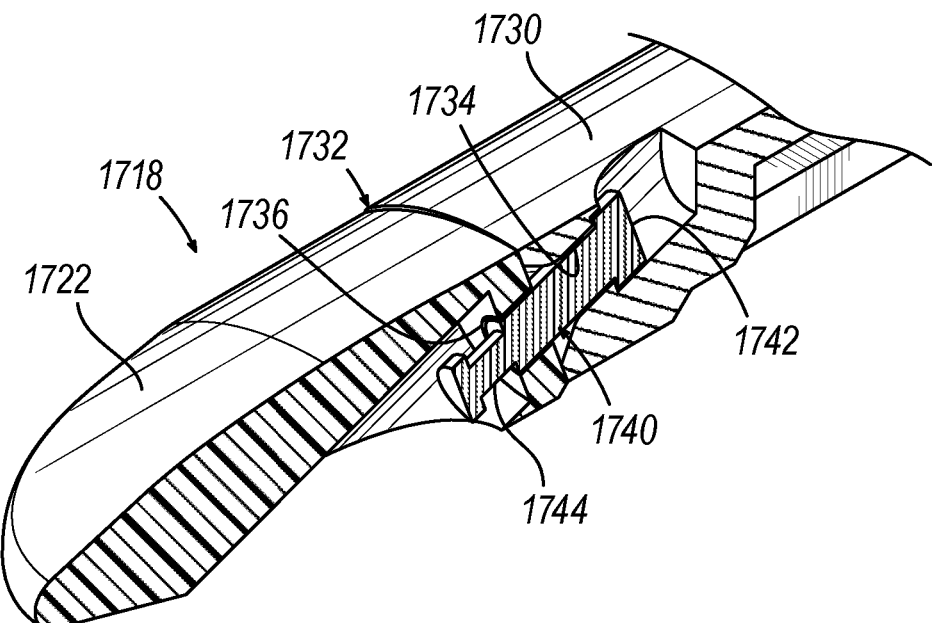
FIG. 45 depicts a partially sectioned perspective view of a distal portion of another exemplary anvil having a selectively rotatable distal tip and a tip locking mechanism, showing the distal tip in phantom to reveal internal features.

FIG. 45 shows a distal portion of another exemplary anvil (1718) suitable for use with any of the exemplary end effectors described above. Anvil (1718) is similar to anvils (1318, 1418, 1518, 1618) described above except as otherwise described below. Like anvils (1318, 1418, 1518, 1618), anvil (1718) includes an elongate anvil body (not shown) having a plurality of staple forming pockets arranged along an underside thereof, a connection member (1730) secured to a distal end of the anvil body, and a tapered distal tip (1722) rotatably coupled to connection member (1730). Like anvil tips (1322, 1422, 1522, 1622), anvil tip (1722) is configured to swivel relative to connection member (1730) about a rotational axis disposed within a plane that contains the longitudinal axis of the anvil body and a longitudinal centerline of a corresponding end effector having lower jaw (16). In particular, anvil tip (1722) is configured to swivel about the rotational axis between a first discrete position in which anvil tip (1722) is angled relative to the anvil body in a direction toward lower jaw (16), and a second discrete position in which anvil tip (1722) extends distally straight from the anvil body so as to be oriented away from lower jaw (16). Connection member (1730) and anvil tip (1722) define an angled interface (1732) therebetween that provides for the angular reorientation of anvil tip (1722) relative to the longitudinal axis of the anvil body during rotation of anvil tip (1722) between the first and second discrete positions.

Figure 46:
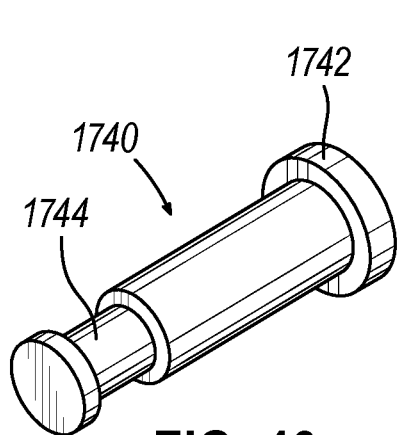
FIG. 46 depicts a perspective view of an exemplary shaft that permits rotation of the distal tip of the anvil of FIG. 45.
Figure 47:
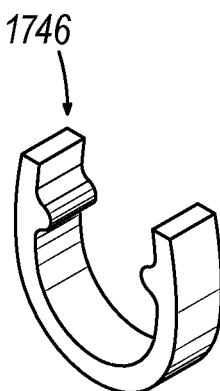
FIG. 47 depicts a perspective view of an exemplary clip configured to secure the shaft of FIG. 46 axially relative to the distal tip and a connection member of FIG. 45.

As shown in FIG. 45, connection member includes a first bore (1734) that extends obliquely to a longitudinal axis of connection member (1730) and the anvil body, and anvil tip (1722) includes a second bore (1736) that aligns coaxially with first bore (1734). A shaft (1740) provided independently of anvil tip (1722) and connection member (1730) is disposed within first and second bores (1734, 1736) and enables anvil tip (1722) to rotate relative to connection member (1730) between the first and second discreet positions. As shown in FIG. 46, a proximal end of shaft (1740) includes a radially enlarged head (1742), and a distal end of shaft (1740) includes an annular groove (1744). Shaft (1740) is configured to be received within first and second bores (1734, 1736) such that proximal head (1742) seats against an internal stop shoulder (not shown) of first bore (1734), and such that annular groove (1744) is exposed through a distal end of second bore (1736) so that a C-clip (1746), shown in FIG. 47, can be applied to annular groove (1744). The proximal portion of shaft (1740) may be received by first bore (1734) with a press-fit engagement while the distal portion of shaft (1740) is received within second bore (1736) with a slip-fit engagement, thus permitting rotation of anvil tip (1722) about anvil shaft (1740) while anvil tip (1722) is retained axially on shaft (1740) by C-clip (1746).

Figure 48:
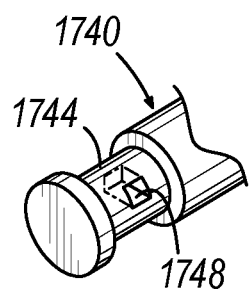
FIG. 48 depicts an enlarged perspective view of a distal portion of the shaft of FIG. 46, showing an exemplary detent feature of the tip locking mechanism of the anvil.
Figure 49:
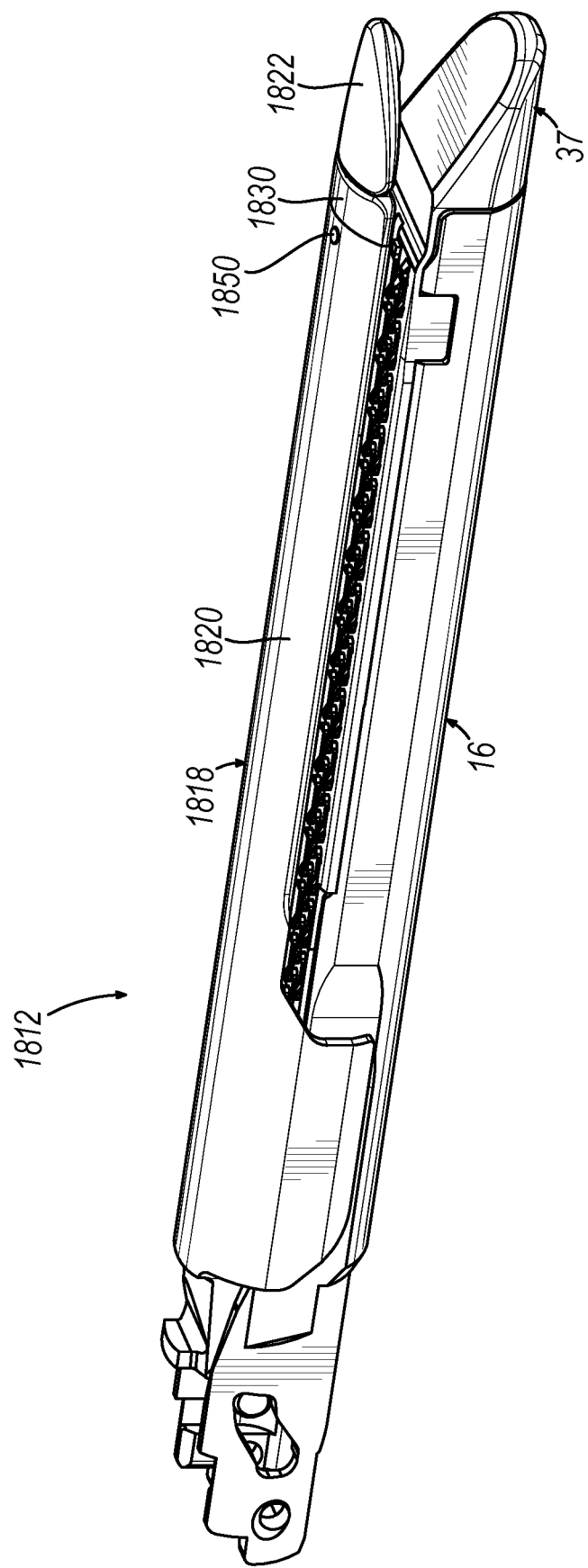
FIG. 49 depicts a perspective view of an exemplary end effector having an anvil with a toggling distal tip that is pivotable about a transverse axis, showing the distal tip in a first discrete position relative to a body of the anvil.

Anvil (1718) may further include a tip locking mechanism operable to releasably retain anvil tip (1722) in the first and second discrete positions relative to connection member (1730) and the anvil body. In the present version, as shown in FIG. 48, a detent recess (1748) is provided on the distal portion of shaft (1740) in annular groove (1744) and is configured to engage a corresponding detent protrusion (not shown) secured to anvil tip (1722). In other versions, a reverse configuration may be provided in which shaft (1740) is fixed to anvil tip (1722) and is rotatably disposed within first bore (1734) of connection member (1730), where the proximal portion of shaft (1740) provides a first detent feature and connection member (1730) provides a second detent feature. Furthermore, it will be appreciated that various other types of tip locking mechanisms may be employed.

H. Exemplary Anvils with Toggling Tip Pivotable About Transverse Axis

As discussed above in connection with FIGS. 37-48, in some instances it may be desirable to rotatably mount an adjustable anvil tip relative to an anvil body such that the tip is rotatable between discrete positions about an axis contained within a vertical plane that extends parallel to a length of the end effector. In other instances, it may be desirable to alternatively mount an adjustable anvil tip relative to the anvil body such that the tip is pivotable between discrete positions about a lateral axis that extends transversely to a length of the end effector; for example, in a manner similar to the pivoting configuration described above in connection with FIGS. 13-16, but with unique features and functionality as described below in connection with the toggling tips of FIGS. 53-71.

It will be appreciated that the exemplary features described below in connection with FIGS. 53-71 may be combined with any of the other exemplary features described herein. In that regard, the exemplary tips and related features described below may be substituted for similar components of any of the exemplary surgical instruments described herein to achieve desired performance characteristics in various types of surgical stapling procedures.

1. Toggling Tip and Connection Member Having Detent Recesses

FIGS. 49-52B illustrate an exemplary end effector (1812) that includes an anvil (1818) pivotably coupled with lower jaw (16), and staple cartridge (37) positioned within lower jaw (16). Anvil (1818) is similar to anvils (1318, 1418, 1518, 1618, 1718) described above except as otherwise described below. Like anvils (1318, 1418, 1518, 1618, 1718), anvil (1818) includes an elongate anvil body (1820) having a plurality of staple forming pockets arranged along an underside thereof, a connection member (1830) secured to a distal end of anvil body (1820) with a retaining pin (1850), and a tapered distal tip (1822) movably coupled to connection member (1730). Unlike anvil tips (1322, 1422, 1522, 1622, 1722), anvil tip (1822) is configured to pivot relative to connection member (1830) about a lateral axis that extends transversely to the longitudinal axis of anvil body (1820) and a longitudinal centerline of end effector (1812). As described below in connection with FIGS. 52A and 52B, anvil tip (1822) is configured to pivotably toggle about this transverse axis between a first discrete position in which anvil tip (1822) is angled relative to anvil body (1820) in a direction toward lower jaw (16) (see FIG. 52A); and a second discrete position in which anvil tip (1822) extends distally straight from anvil body (1820) so as to be oriented away from lower jaw (16) (see FIGS. 49 and 52B). A user may select the angled position or the straight position of anvil tip (1822) as desired to best facilitate a particular procedure being performed.

Figure 50:
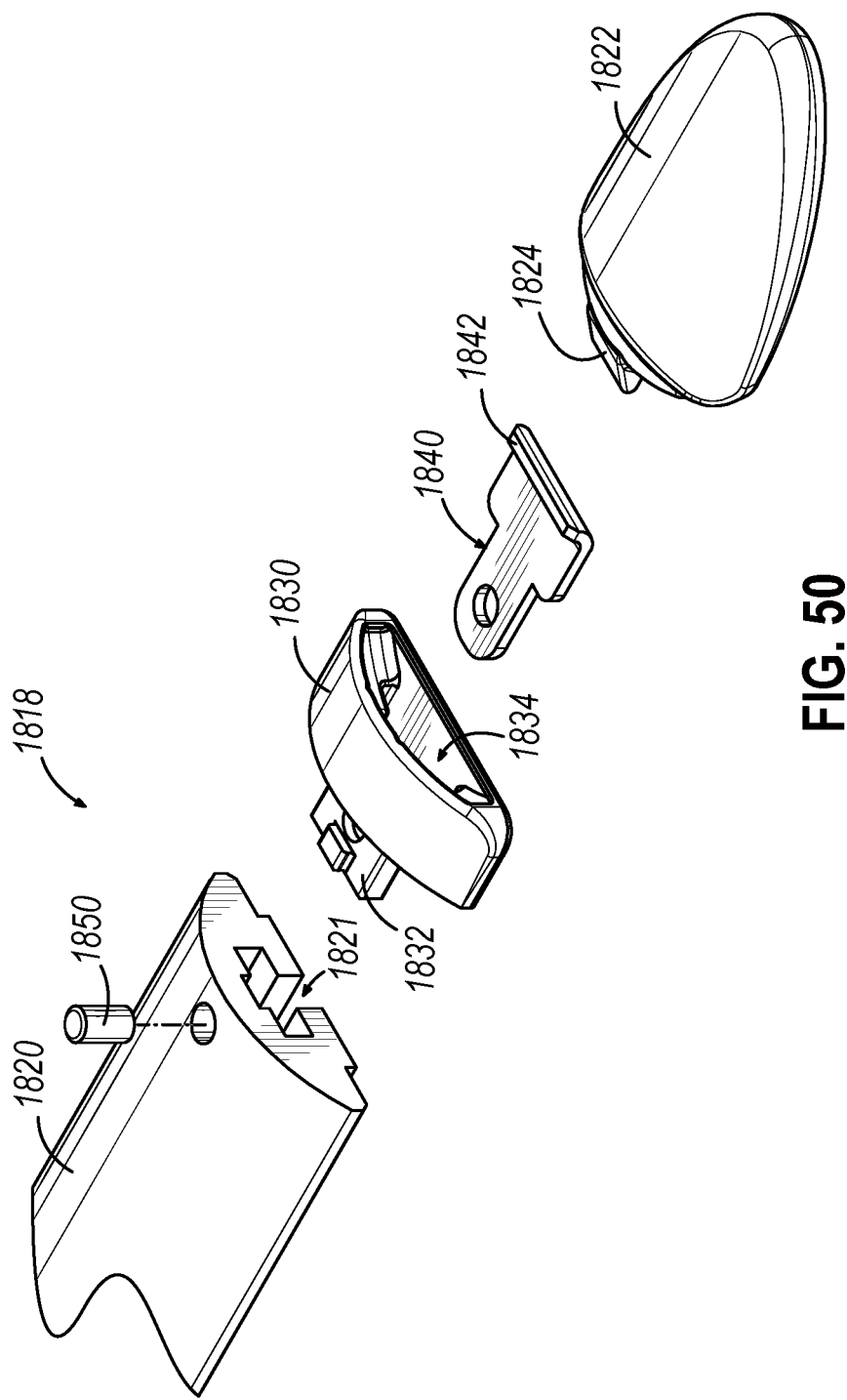
FIG. 50 depicts an exploded perspective view of a distal portion of the anvil of FIG. 49, showing the anvil body, the distal tip, a connection member, a spring plate, and a retaining pin.
Figure 51:
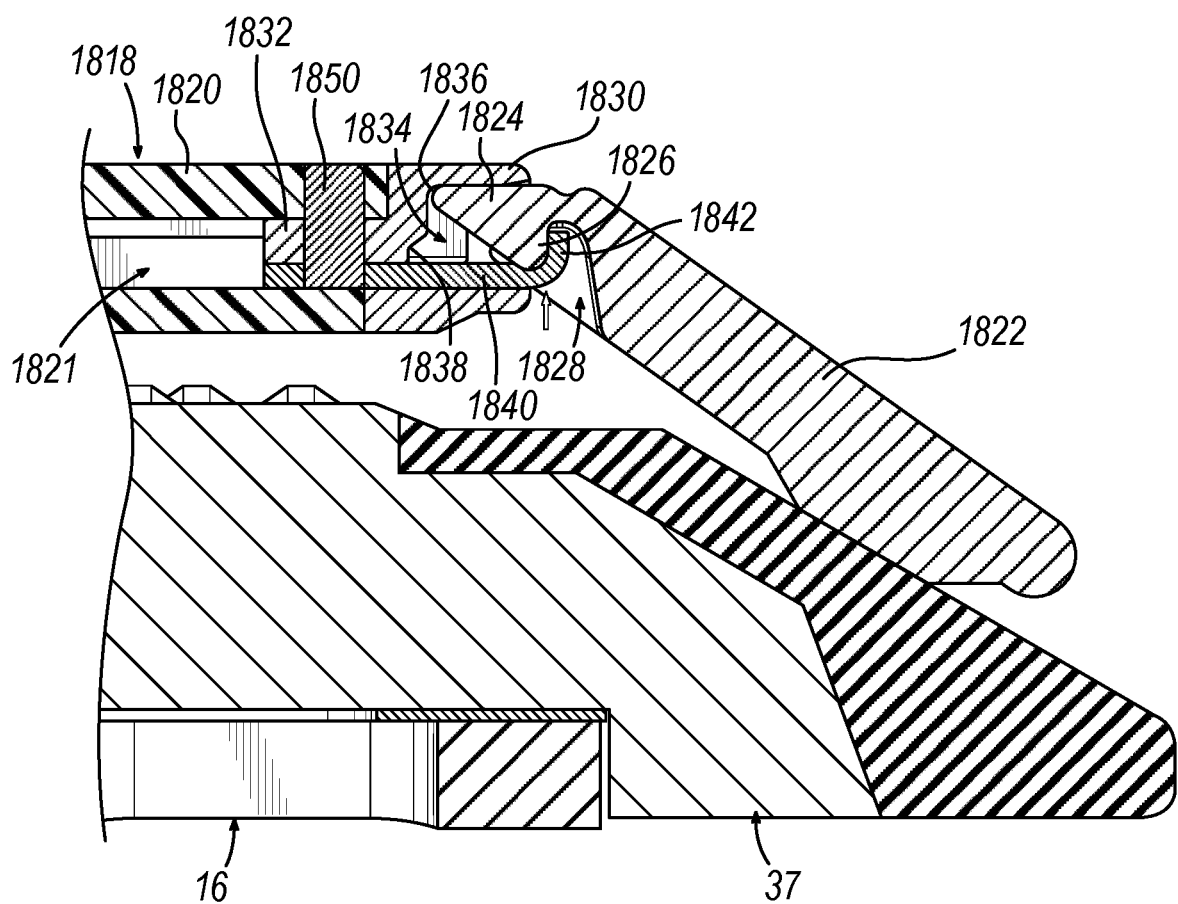
FIG. 51 depicts a side sectional view of the end effector of FIG. 49, showing the distal tip releasably retained in a second discrete position relative to the anvil body.
Figure 52A:
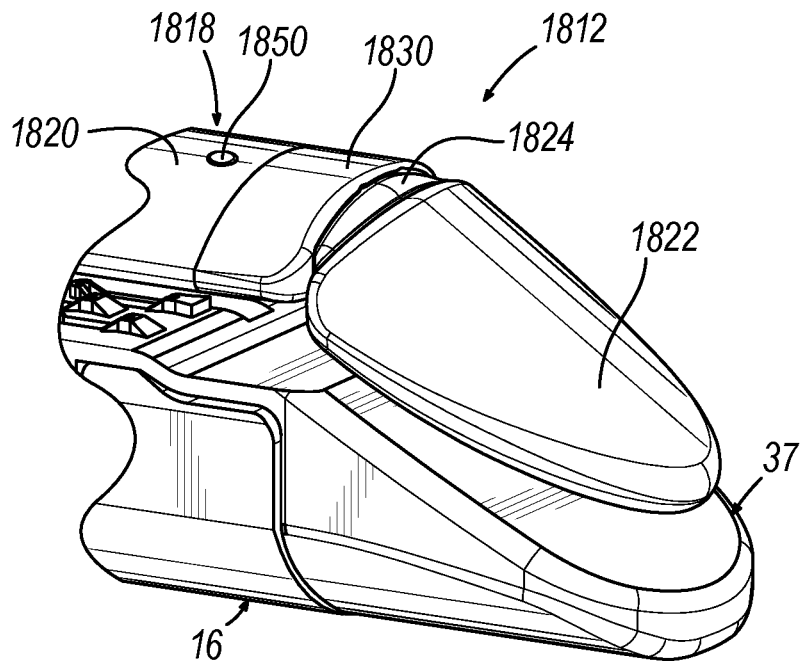
FIG. 52A depicts a perspective view of a distal portion of the end effector of FIG. 49, showing the distal tip in the second discrete position relative to the anvil body.
Figure 52B:
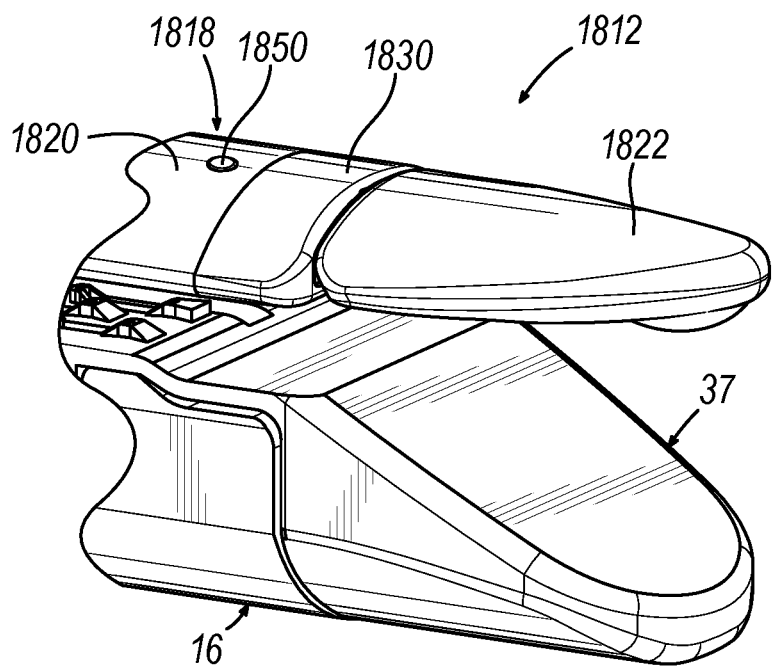
FIG. 52B depicts a perspective view of the distal portion of the end effector of FIG. 49, showing the distal tip in the first discrete position relative to the anvil body.

As shown in FIGS. 50 and 51, a proximal end of connection member (1830) (also known as a "base") includes a plug (1832) that is securely received within a longitudinal slot (1821) of anvil body (1820). Plug (1832) includes features that provide it with a generally t-shaped profiled configured to match a t-shaped profiled of longitudinal slot (1821). Connection member (1830) further includes an interior space in the form of an axially extending inner channel (1834) that communicates with an open proximal end of connection member (1830) and which is configured to receive the proximal end of a spring plate (1840) (also referred to as a "hinge plate") therein. A retaining pin (1850) extends vertically through openings formed in the distal end of anvil body (1820), connection member plug (1832), and a proximal end of spring plate (1840), thereby securing connection member (1830) and spring plate (1840) axially relative to anvil body (1820).

The proximal end of anvil tip (1822) includes a tapered protrusion (1824) that extends proximally into inner channel (1834) of connection member (1830), through the open proximal end. Tapered protrusion (1824) functions as a detent feature configured to releasably engage upper and lower detent recesses (1836, 1838), and an intermediate surface disposed therebetween, formed within the inner channel (1834). Tapered protrusion (1824) includes a lower knuckle (1826) that overlies a cavity (1828) formed in the underside of the proximal end of anvil tip (1822). A distal lip (1842) of spring plate (1840) wraps arcuately over lower knuckle (1826) and upwardly into tip cavity (1828), thereby retaining tapered protrusion (1824) of anvil tip (1822) proximally within the open proximal end of connection member (1830) and in engagement with detent recesses (1836, 1838). Distal lip (1842) also defines a lateral hinge axis about which anvil tip (1822) hinges relative to anvil body (1820).

The contact between spring plate (1840) and tapered protrusion (1824) defines a laterally extending axis about which anvil tip (1822) is configured to pivotably toggle relative to connection member (1830) and anvil body (1820) between the first and second discrete positions. In particular, anvil tip (1822) exhibits the first, angled discrete position seen in FIGS. 51 and 52A when tapered protrusion (1824) is seated within upper detent recess (1836). Conversely, anvil tip (1822) exhibits the second, straight discrete position seen in FIGS. 49 and 52B when tapered protrusion (1824) is seated within lower detent recess (1838). As shown in FIG. 51, in the present example lower detent recess (1838) is recessed proximally of upper detent recess (1836). Additionally, in some examples, the intermediate surface seen in FIG. 51 that separates upper detent recess (1836) from lower detent recess (1838) may protrude slightly distally.

Spring plate (1840) of the present example is resilient in construction and is configured to resiliently bias anvil tip (1822) toward the first and second discrete positions, away from an intermediate position. While pivoting between the first and second discrete positions, tapered protrusion (1824) of tip (1822) frictionally engages the intermediate internal surface of connection member (1830) defined between upper and lower detent recesses (1836, 1838). This contact urges lower knuckle (1826) distally against distal lip (1842) of spring plate (1840), thus forcing spring plate (1840) to resiliently deflect. In turn, distal lip (1842) exerts a proximally directed resilient bias force on lower knuckle (1826), thus urging tapered protrusion (1824) toward one of detent recesses (1836, 1838). As a result of this resilient bias imparted by spring plate (1840), anvil tip (1822) may "snap" into place upon assuming one of the first or second discrete positions.

It will be appreciated that the resilient bias imparted by spring plate (1840) is strong enough to prevent inadvertent toggling of anvil tip (1822) during a surgical procedure, and weak enough to be conveniently overcome by a user when selectively adjusting anvil tip (1822). In some versions, the input "toggle force" required to toggle anvil tip (1822) between its discrete positions may be approximately 2 lbf, for example. Accordingly, the engagement of tapered protrusion (1824) with detent recesses (1836, 1838) functions as a tip locking mechanism operable to releasably retain anvil tip (1822) in the first and second discrete positions relative to anvil body (1820).

While retaining pin (1850) described above is shown with a solid construction, retaining pin (1850) may be provided with a hollow spring pin construction in other versions. During toggling of anvil tip (1822), such a spring pin may resiliently compress in a radial direction, thereby permitting slight distal translation of spring plate (1840) relative to connection member (1830), and thus requiring less deflection of distal lip (1842) of spring plate (1840) as compared to use of a solid spring pin (1850). The stiffness of such a spring pin may be selected to tune the input toggle force required to transition anvil tip (1822) between the first and second discrete positions. In particular, a spring pin of greater stiffness may yield a higher input toggle force, while a spring pin of lesser stiffness may yield a lower input toggle force.

2. Toggling Tip and Spring Plate Having Spring Arm

As described above, tapered proximal protrusion (1824) of distal anvil tip (1822) is configured to contact a rigid structure defined by an inner surface of connection member (1830) when tip (1822) transitions between the first and second discrete positions. Accordingly, the resilient biasing forces exerted on anvil tip (1822) for urging tip (1822) toward the first and second discrete positions are imparted by distal lip (1842) of spring plate (1840), via lower knuckle (1826) at the distal end of tapered protrusion (1824). In some instances, it may be desirable to reconfigure this toggling assembly so that the resilient biasing force is exerted at the proximal end of tapered proximal protrusion (1824). FIGS. 53-60C, described below, show an exemplary version of such a configuration.

Figure 53:
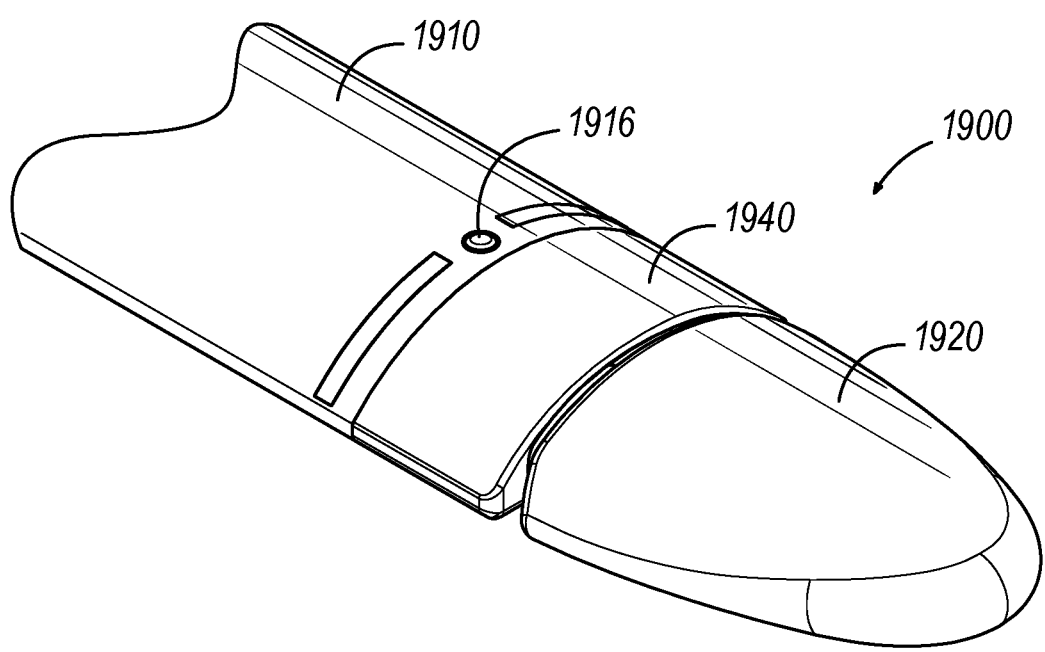
FIG. 53 depicts a perspective view of the distal portion of an anvil having a toggling distal tip that is pivotable about a transverse axis, showing the distal tip in a first discrete position relative to a body of the anvil.
Figure 54:
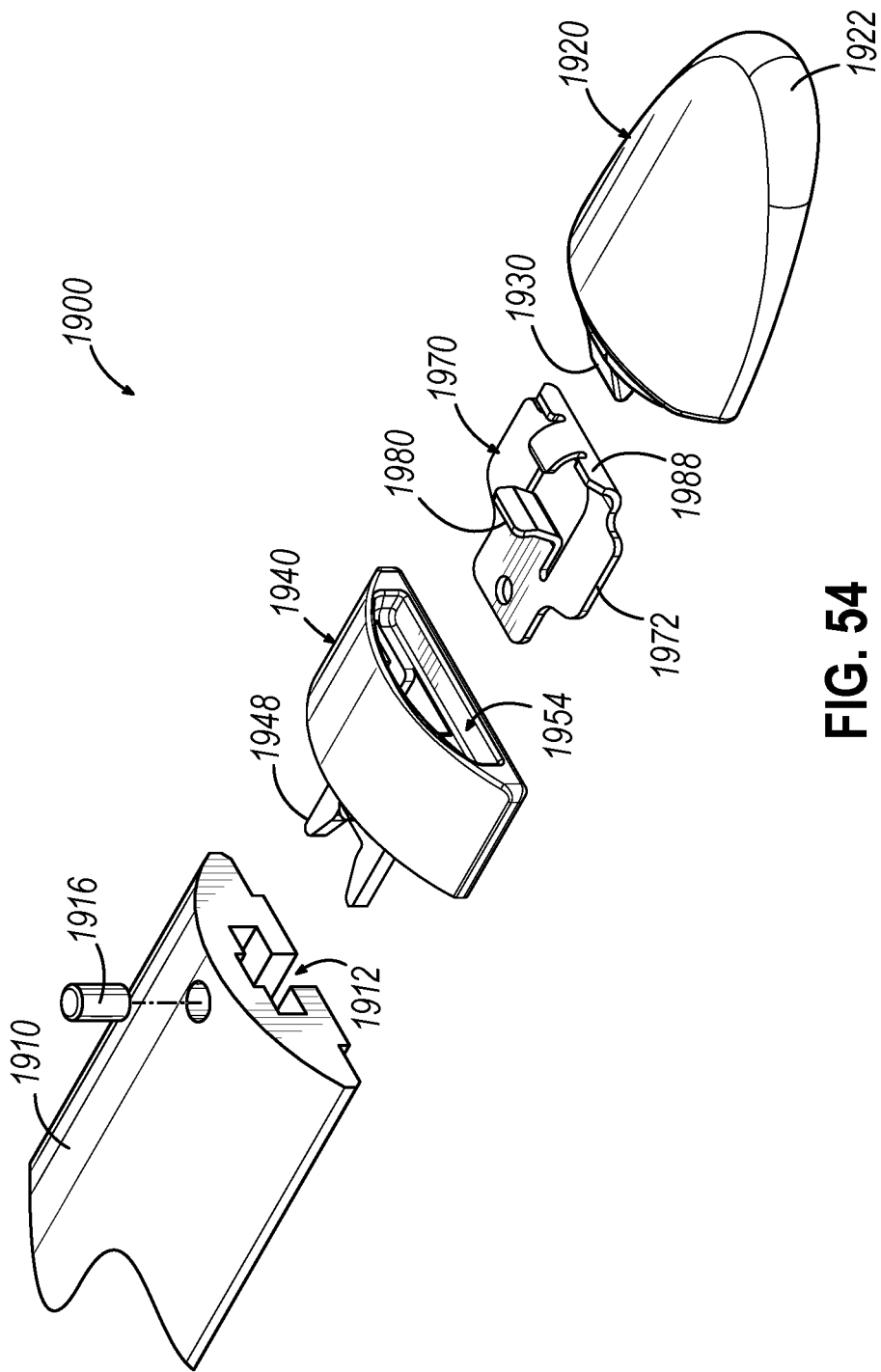
FIG. 54 depicts an exploded perspective view of the distal portion of the anvil of FIG. 53, showing the anvil body, the distal tip, a connection member, a spring plate, and a retaining pin.

FIGS. 53-60C show another exemplary anvil (1900) having a tapered distal tip (1920) configured to pivotably toggle about a transverse axis between a first discrete position and a second discrete position. Anvil (1900) is similar to anvil (1818) described above except as otherwise described below. Furthermore, anvil (1900) is configured for use with any of the exemplary end effectors and surgical instruments described herein. As shown in FIGS. 53-54, anvil (1900) includes an elongate anvil body (1910), a connection member (1940) fixedly coupled to a distal end of anvil body (1910), a spring plate (1970) housed within connection member (1940), a retaining pin (1916) that secures connection member (1940) and spring plate (1970) relative to anvil body (1910), and tapered distal tip (1920) movably coupled with connection member (1940) via spring plate (1970).

Figure 55:
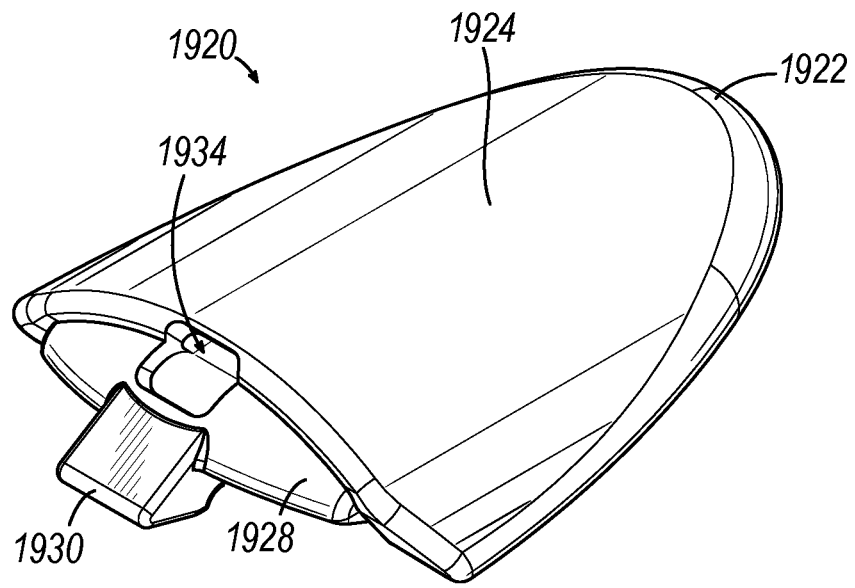
FIG. 55 depicts a proximal perspective view of an upper side of the distal tip of the anvil of FIG. 53.
Figure 56:
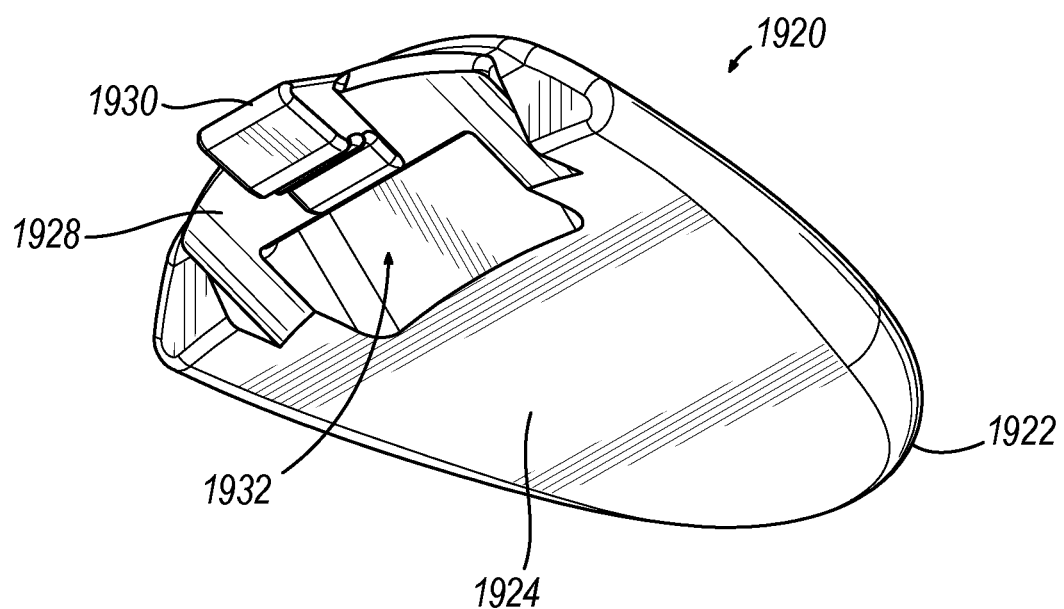
FIG. 56 depicts a proximal perspective view of an under side of the distal tip of the anvil of FIG. 53.

As shown in FIGS. 55-56, anvil tip (1920) of the present version has a distally tapered shape with a rounded distal end (1922), a generally convex upper surface (1924), and a generally concave lower surface (1926). The proximal end of anvil tip (1920) includes a plurality of features that enable tip (1920) to couple with connection member (1940) and spring plate (1970) in the manner described below. In particular, the proximal end of anvil tip (1920) includes a hinge structure (1928) recessed below convex upper surface (1924). A tapered protrusion (1930) extends proximally from hinge structure (1928) in an angularly downward direction toward concave lower surface (1926). As shown in FIG. 56, a proximal end of the underside of anvil tip (1920) includes a cavity (1932) that extends angularly upward through an underside of hinge structure (1928) and toward convex upper surface (1924). In the present version, tapered protrusion (1930) and cavity (1932) are disposed along a longitudinal centerline of anvil tip (1920). As shown in FIG. 55, an opening (1934) is formed in a rounded upper surface of hinge structure (1928) and communicates with cavity (1932).

Figure 57:
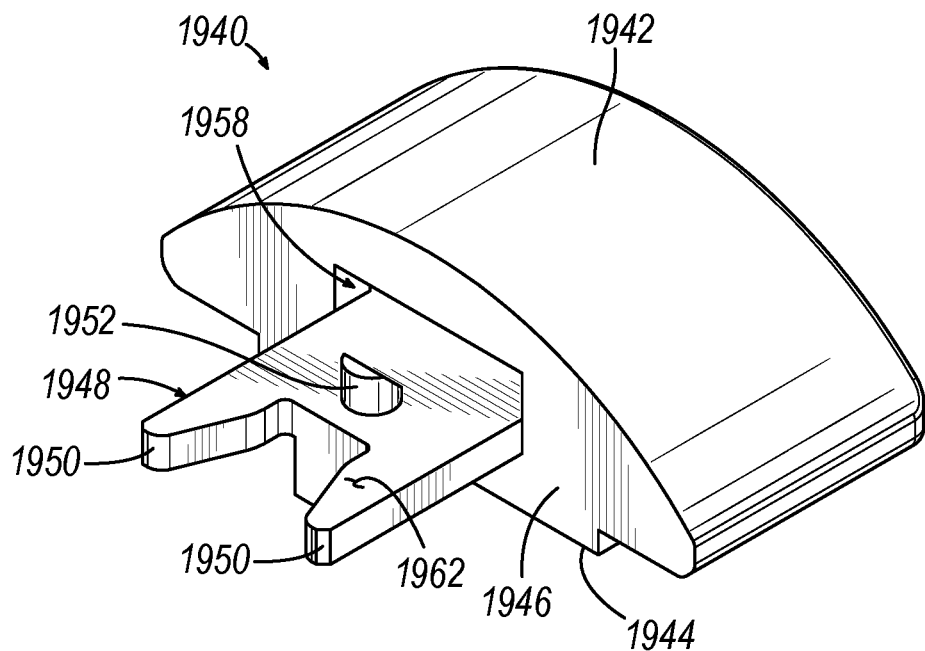
FIG. 57 depicts a proximal perspective view of the connection member of the anvil of FIG. 53.
Figure 58:
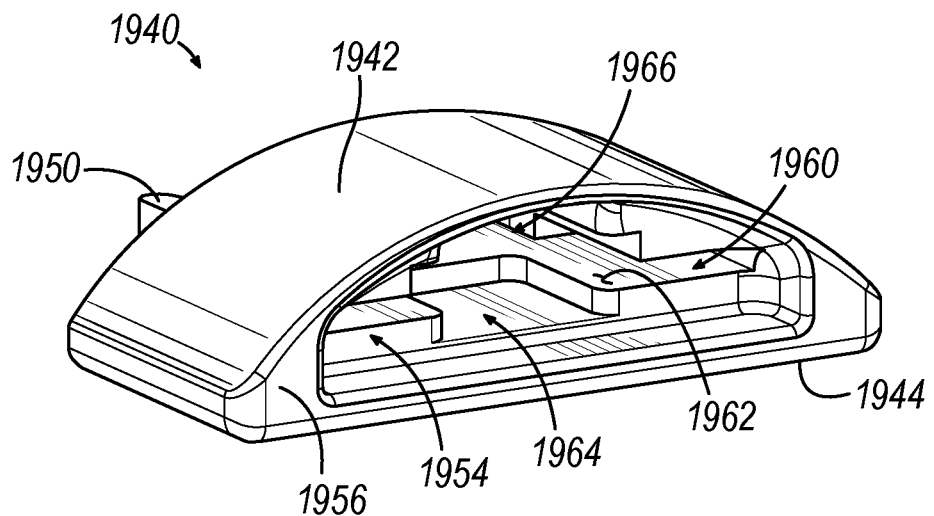
FIG. 58 depicts a distal perspective view of the connection member of the anvil of FIG. 53.

As shown in FIGS. 57-58, connection member (1940) of the present version is shaped with a cross-sectional profile that generally matches the profile of anvil body (1910). In particular, connection member (1940) includes a convex upper surface (1942) and a generally flat lower surface (1944). As shown in FIG. 57, a plug (1948) protrudes proximally from a proximal face (1946) of connection member (1940) and includes a pair of side arms (1950) that provide plug (1948) with a generally t-shaped profile that matches a t-shaped profile of a longitudinal knife slot (1912) of anvil body (1910). Accordingly, plug (1948) is configured to be received within an open distal end of longitudinal slot (1912) of anvil body (1910), for example with a friction fit. A retaining post (1952) protrudes upwardly from an upper side of plug (1948) and is configured to anchor a proximal tab (1976) of spring plate (1970) to plug (1948), as described below. In the present version, a distal side of retaining post (1952) includes a chamfer that facilitates engagement of spring plate (1970) with post (1952) during assembly.

Figure 60A:
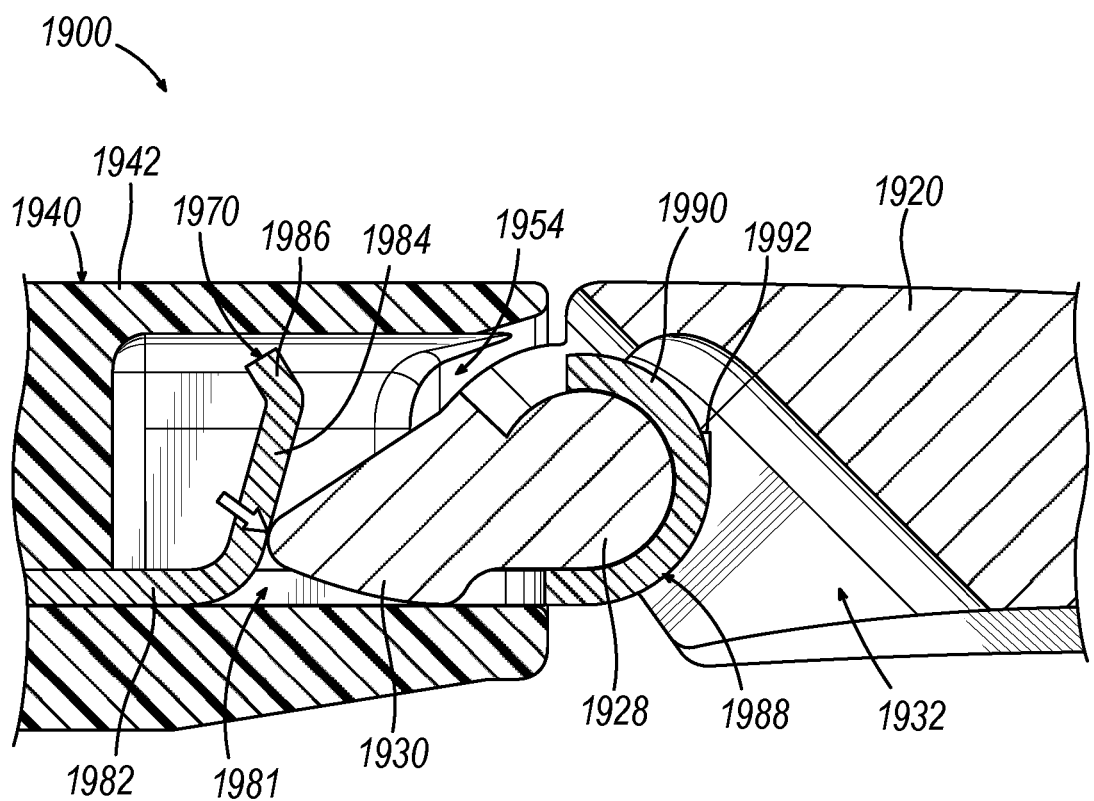
FIG. 60A depicts a side sectional view of the anvil of FIG. 53, showing the distal tip in a first discrete position in which the distal tip is parallel to the anvil body.
Figure 60B:
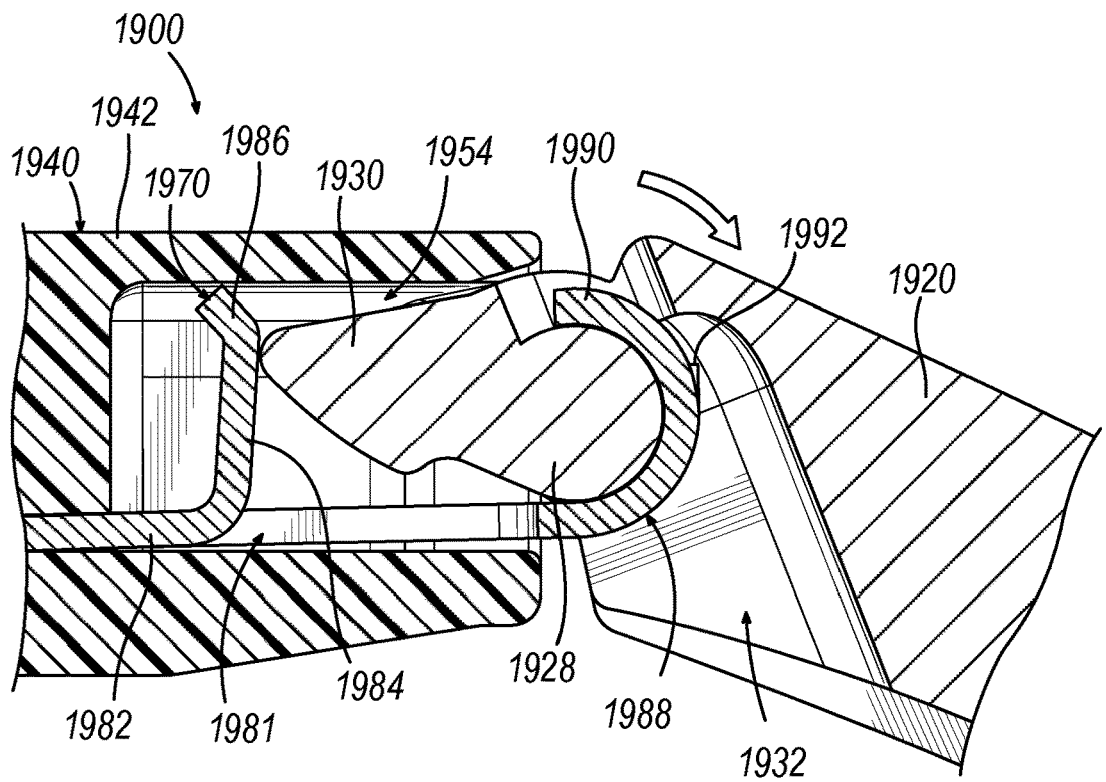
FIG. 60B depicts a side sectional view of the anvil of FIG. 53, showing the distal tip in an intermediate position in which the distal tip is transitioning from the first discrete position of FIG. 60A toward a second discrete position.
Figure 60C:
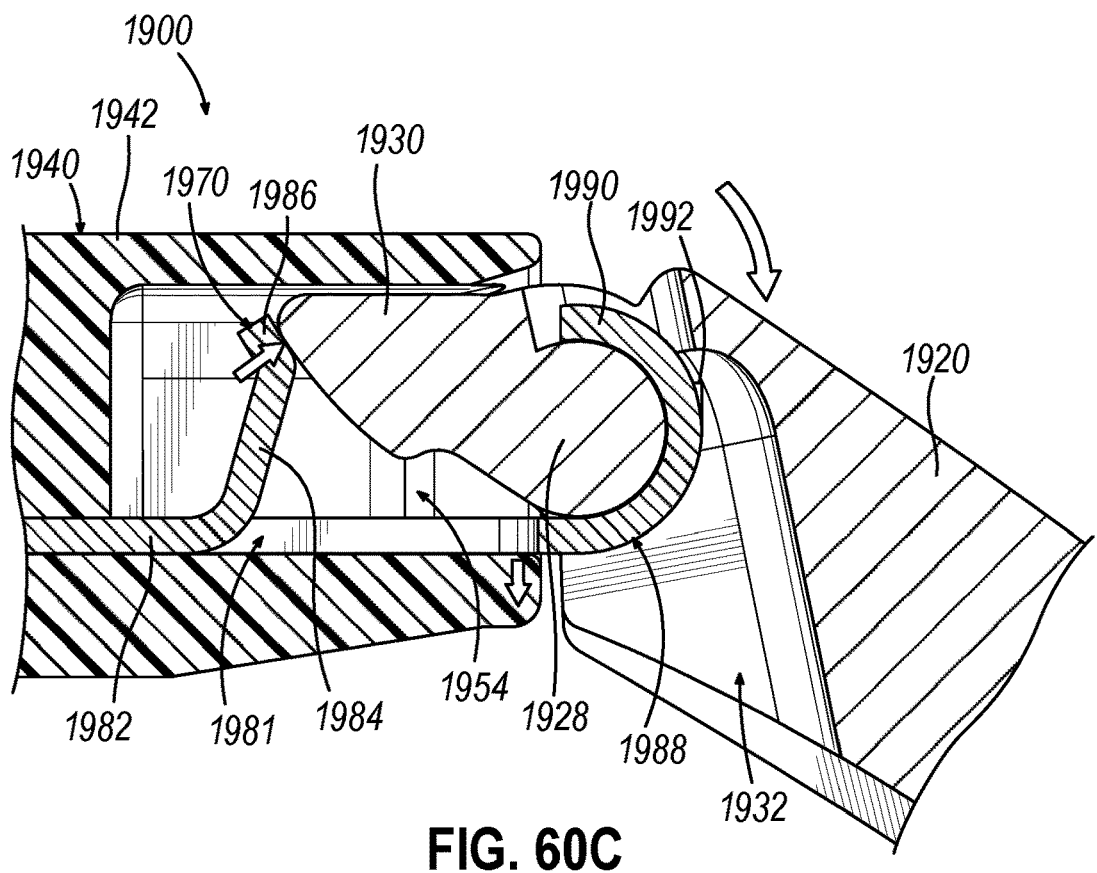
FIG. 60C depicts a side sectional view of the anvil of FIG. 53, showing the distal tip in a first discrete position in which the distal tip is parallel to the anvil body.

As shown in FIG. 58, connection member (1940) includes an inner channel (1954) that opens to a distal face (1956) of connection member (1940). Inner channel (1954) is configured to receive spring plate (1970) therein, as shown in FIGS. 60A-60C described below. As shown in FIG. 57, proximal face (1946) of connection member (1940) includes a window (1958) that communicates with inner channel (1954) and is configured to receive proximal tab (1976) of spring plate (1970) therethrough so that proximal tab (1976) may couple with post (1952). As shown best in FIG. 58, inner channel (1954) includes a generally rectangular inner cavity (1960) that is configured to receive a base plate portion (1972) of spring plate (1970), and which is bounded by a planar support surface (1962) that extends through proximal window (1958) and is configured to support a base plate portion (1972) thereon. Inner channel (1954) further includes a lower recess (1964) formed at a distal end of support surface (1962), and an upper recess (1966) positioned directly above lower recess (1964). Upper and lower recesses (1964, 1966) are configured to accommodate, and define upper and lower limits for, vertical movements of proximal tapered protrusion (1930) of anvil tip (1920) within inner channel (1954) as anvil tip (1920) pivots relative to connection member (1940) between first and second discrete positions.

Figure 59:
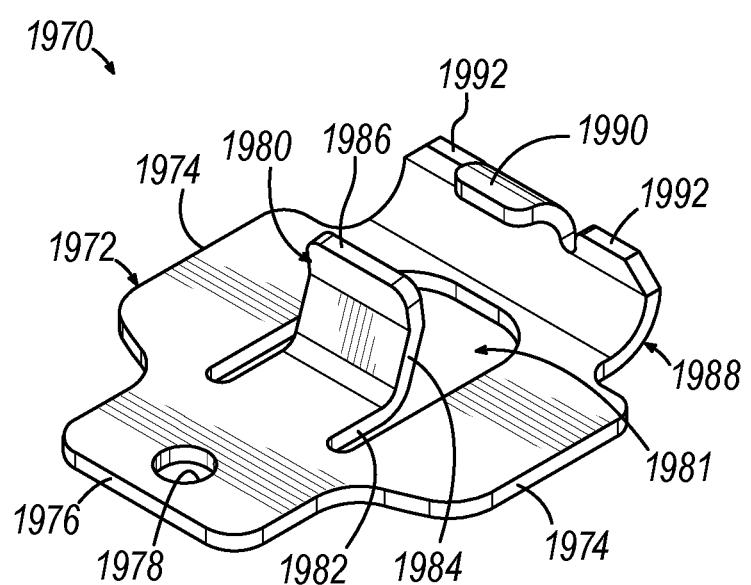
FIG. 59 depicts a perspective view of the spring plate of the anvil of FIG. 53.

As shown in FIG. 59, spring plate (1970) of the present version includes a base plate portion (1972) having a pair of laterally opposed side tabs (1974) and a proximal tab (1976) having an opening (1978). Opening (1978) is configured to receive retaining post (1952) of connection member plug (1948) upwardly therethrough, thereby fixing spring plate (1970) longitudinally relative to connection member (1940). Opening (1978) may also be configured to a receive a lower end of retaining pin (1916) downwardly therethrough, thereby more securely fixing connection member (1940) and spring plate (1970) longitudinally relative to anvil body (1910). Spring plate (1970) further includes a proximal spring arm (1980) that protrudes upwardly from a middle portion of base plate portion (1972), away from a central opening (1981) in base plate portion (1972). Proximal spring arm (1980) includes a base arm segment (1982) that extends parallel with base plate portion (1972), a medial arm segment (1984) extending angularly upward from base arm segment (1982), and an upper arm segment (1986) extending vertically upward from medial arm segment (1984). As described below, proximal spring arm (1980) is configured to resiliently deflect relative to base plate portion (1972) and thereby resiliently bias proximal tapered protrusion (1930) of anvil (1900) tip toward each of the first and second discrete positions.

As also shown in FIG. 59, a distal end of spring plate (1970) includes an arcuate hinge lip (1988) that curves upwardly from base plate portion (1972). An upper end of hinge lip (1988) includes a finger (1990) in alignment with proximal spring arm (1980) along a centerline of spring plate (1970), and a pair of pivot guide tabs (1992) disposed along the lateral sides of finger (1990). As shown in FIGS. 60A-60C, hinge lip (1988) is configured to pivotably capture hinge structure (1928) such that finger (1990) wraps circumferentially around a distal side of hinge structure (1928)

within tip cavity (1932) and extends upwardly and proximally through opening (1934). Anvil tip (1920) is thus pivotably coupled to spring plate (1970), and thus with connection member (1940) and anvil body (1910), while remaining longitudinally constrained relative to anvil body (1910) by spring plate (1970).

Hinge structure (1928) of anvil tip (1920) and hinge lip (1988) of spring plate (1970) extend laterally, thereby defining a hinge axis that is transverse to a longitudinal axis of anvil body (1910). Anvil tip (1920) is configured to pivot about this hinge axis between the first and second discrete positions. Additionally, hinge lip (1988) is configured to resiliently flex in proximal and distal directions, as well as in upward and downward directions, thereby permitting minimal degrees of translation (or "shifting") of anvil tip (1920) relative to connection member (1940), in addition to the above-described pivoting, while transitioning between the first and second discrete positions.

FIGS. 60A-60C show an exemplary progression of anvil tip (1920) being pivoted about a transverse axis between an exemplary first discrete position and an exemplary second discrete position. In the first discrete position (FIG. 60A), anvil tip (1920) is "straight" and extends parallel to a longitudinal axis of anvil body (1910). In the second discrete position (FIG. 60C), anvil tip (1920) is "angled" or "curved" relative to anvil body (1910) and extends angularly downward toward a stapler cartridge (not shown) an opposing end effector jaw (not shown). As described above, the straight configuration may be useful for "marching" the end effector across a tissue structure with sequential stapling and cutting sequences (or "firings"), while the angled configuration may be useful for gathering tissue at the distal end of the end effector for a single firing of the end effector.

As shown in FIG. 60A, anvil tip (1920) is in the straight discrete position such that the proximal end of tapered protrusion (1930) engages the lower end of medial arm segment (1984) of proximal spring arm (1980). Spring arm (1980) exerts a resilient bias force against tapered protrusion (1930) in an angularly downward direction, thereby maintaining anvil tip (1920) in the straight discrete position. Upon application of an external input force to anvil tip (1920) in a downward direction sufficient to overcome this bias force, anvil tip (1920) begins to pivot downwardly relative to spring plate (1970), connection member (1940), and anvil body (1910). This external input force may be imparted by the operator when anvil (1900) is external of the patient, or by a tissue structure against which the operator positions anvil tip (1920) when anvil (1900) is within a patient during a surgical procedure.

FIG. 60B shows tapered protrusion (1930) reaching the sharp bend between upper arm segment (1986) and medial arm segment (1984). This sharp bend serves as a "snap point," such that upon passing downwardly over the joint tapered protrusion (1930) "snaps" downwardly toward the position shown in FIG. 60C under resilient bias force exerted by medial arm segment (1984) against tapered protrusion (1930), thus providing anvil tip (1920) in the downwardly (or "curved") discrete position. This snapping effect may provide the user with an audible and/or tactile indication that anvil tip (1920) has assumed the downwardly angled discrete position, in addition to visual observation. It will be appreciated that a similar snapping effect may take place when anvil tip (1920) is actuated upwardly by an external input force to transition from the downwardly angled discrete position to the straight discrete position. Upon reaching the downwardly angled discrete position shown in FIG. 60C, upper arm segment (1986) of spring arm (1980) exerts a resilient bias force against an underside of tapered protrusion (1930) in an angularly upward direction, thereby maintaining anvil tip (1920) in the downwardly angled discrete position.

As shown in FIGS. 60A-60C, the interface between tapered protrusion (1930) of anvil tip (1920) and spring arm (1980) of spring plate (1970) is proximal to the transverse pivot axis defined by proximal hinge structure (1928) and distal hinge lip (1988). Accordingly, urging tapered protrusion (1930) upwardly within inner channel (1954) of connection member (1940) yields a downward bias of the distal end (1922) of anvil tip (1920) relative to anvil body (1910). Similarly, urging tapered protrusion (1930) upwardly within inner channel (1954) yield an upward bias of the distal end (1922) of anvil tip (1920) relative to anvil body (1910).

Spring arm (1980) of the present version includes two upwardly extending arm segments (1984, 1986) separated by a single sharp bend, thus defining two discrete positions of anvil tip (1920) relative to the anvil body (1910), separated by a single "snap point" transition. Spring arm (1980) may be suitably constructed to locate this "snap point" transition along the vertical dimension of spring arm (1980) to optimize stresses in spring plate (1970) and to tune the kinematics of the resulting transition between the first and second discrete positions of anvil tip (1920). Furthermore, it will be appreciated that spring arm (1980) may be alternatively configured in other versions with various other quantities and configurations of upwardly extending segments, each separated by a corresponding sharp bend that functions as a "snap point" transition, to achieve any desired quantity of discrete positions of anvil tip (1920) relative to anvil body (1910). Moreover, the shape and stiffness of spring arm (1980) may be selected to provide for "snapping" of anvil tip (1920) between adjacent discrete positions in response to a predetermined external input force(s).

3. Exemplary Alternative Spring Plates

In some instances, it may be desirable to alternatively configure one or more features of spring plate (1970) described above to tune various performance characteristics of spring plate (1970); for example, to provide a unique and favorable stress distribution within spring plate (1970) during resilient deflection thereof for a certain application. FIGS. 61-66 show a plurality of exemplary alternative spring plate configurations, each of which is configured for use with anvils (1818, 1900) described above and is similar to spring plate (1970) except as otherwise described below.

Figure 61:
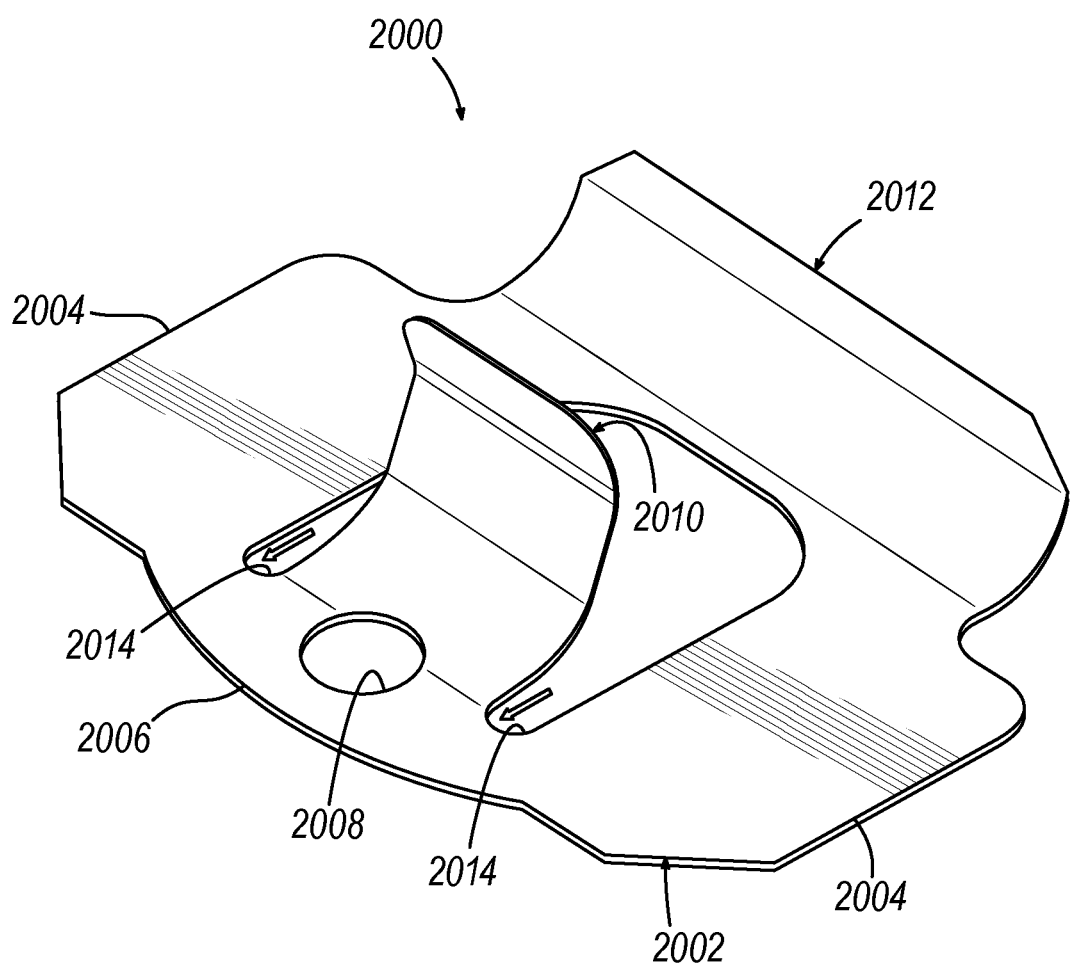
FIG. 61 depicts a schematic perspective of another exemplary spring plate configured for use with the anvil of FIG. 53.

FIG. 61 shows an exemplary spring plate (2000) that includes a base plate portion (2002) having a pair of side tabs (2004) and a proximal tab (2006) with an opening (2008), a proximal spring arm (2010), and a distal hinge lip (2012). In this version, relative to spring plate (1970), side tabs (2004) have been provided with increased surface area, proximal tab (2006) has been rounded, and longitudinal side cuts (2014) at the base of spring arm (2010) have been lengthened in a proximal direction, thereby promoting more favorable stress distribution within spring plate (2000) during its deflection. In other versions, proximal opening (2008) may be omitted and spring plate (2000) may be secured to connection member (1940) in various other suitable manners apparent to those of ordinary skill in the art in view of the teachings herein.

Figure 62:
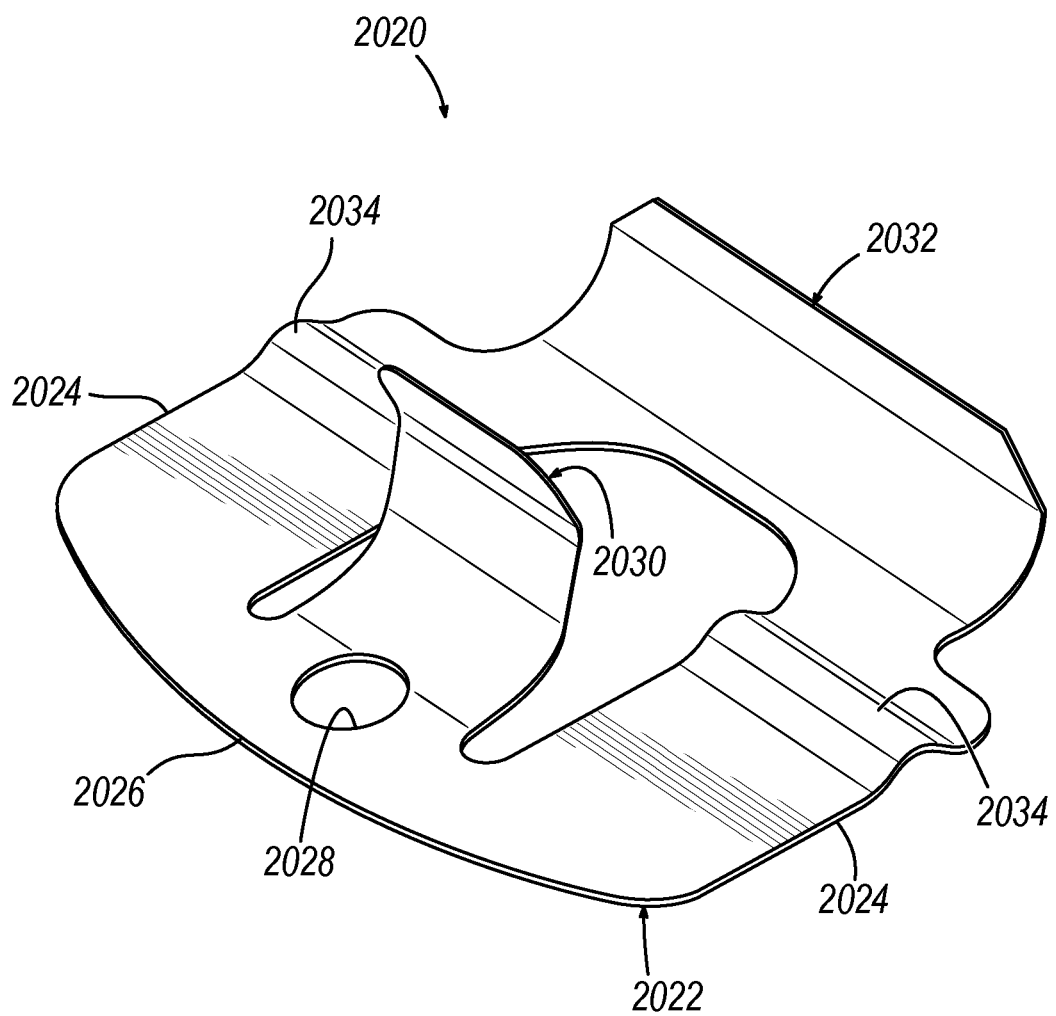
FIG. 62 depicts a schematic perspective of another exemplary spring plate configured for use with the anvil of FIG. 53.

FIG. 62 shows another exemplary spring plate (2020) that includes a base plate portion (2022) having a pair of side tabs (2024) and a rounded proximal end portion (2026) with an opening (2028), a proximal spring arm (2030), and a distal hinge lip (2032). In this version, each side tab (2024) includes a pleat (2034) that extends laterally across the side tab (2024). Pleats (2034) are configured to resiliently extend in a longitudinal direction of spring plate (2020), thereby enabling spring plate (2020) to resiliently elongate during actuation of anvil tip (1920) relative to anvil body (1910) while spring arm (2030) also resiliently deflects relative to base plate portion (2022), thereby redistributing stresses within spring plate (2020).

Figure 63:
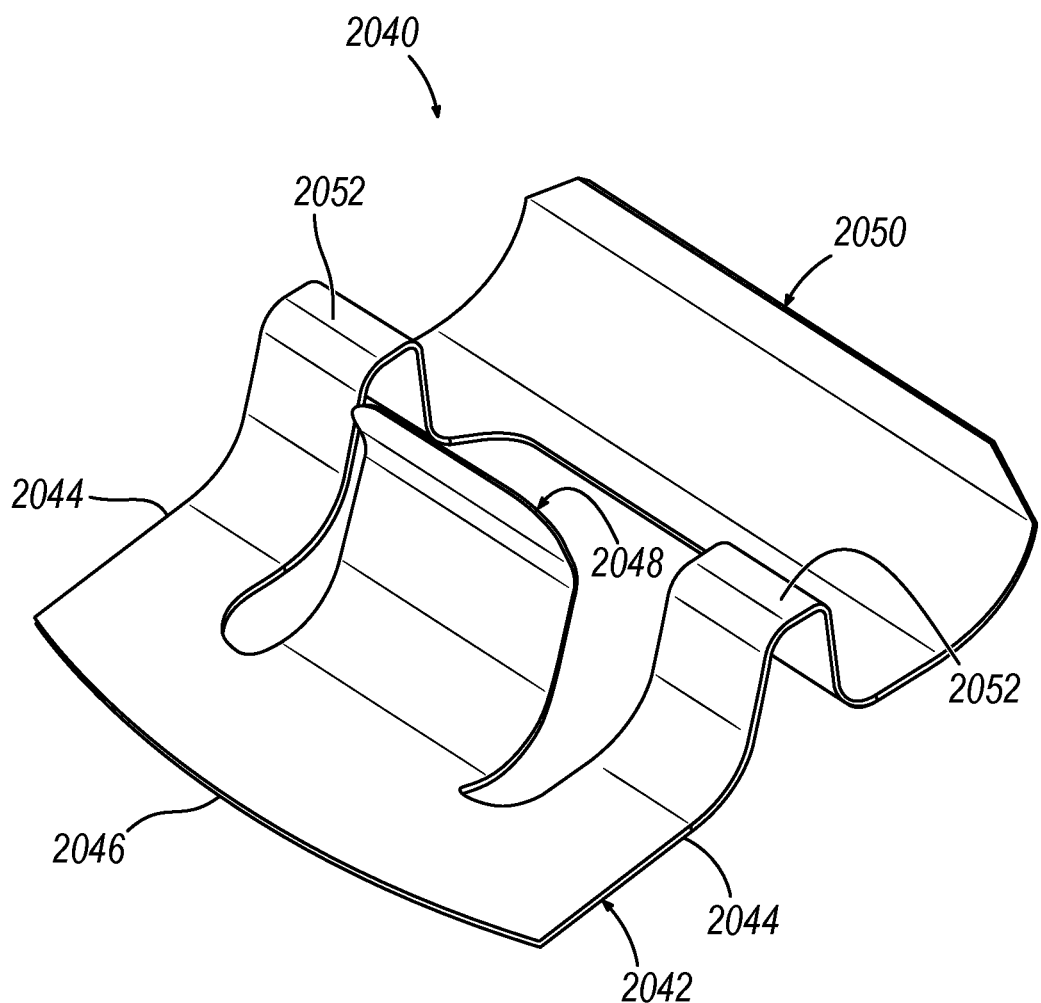
FIG. 63 depicts a schematic perspective of another exemplary spring plate configured for use with the anvil of FIG. 53.

FIG. 63 shows another exemplary spring plate (2040) that includes a base plate portion (2042) having a pair of side tabs (2044) and a rounded proximal end portion (2046), a proximal spring arm (2048), and a distal hinge lip (2050). Similar to spring plate (2020), each side tab (2044) of spring plate (2040) includes a resilient pleat (2052), but with pleats (2052) being taller than pleats (2034) of spring plate (2020).

Figure 64:
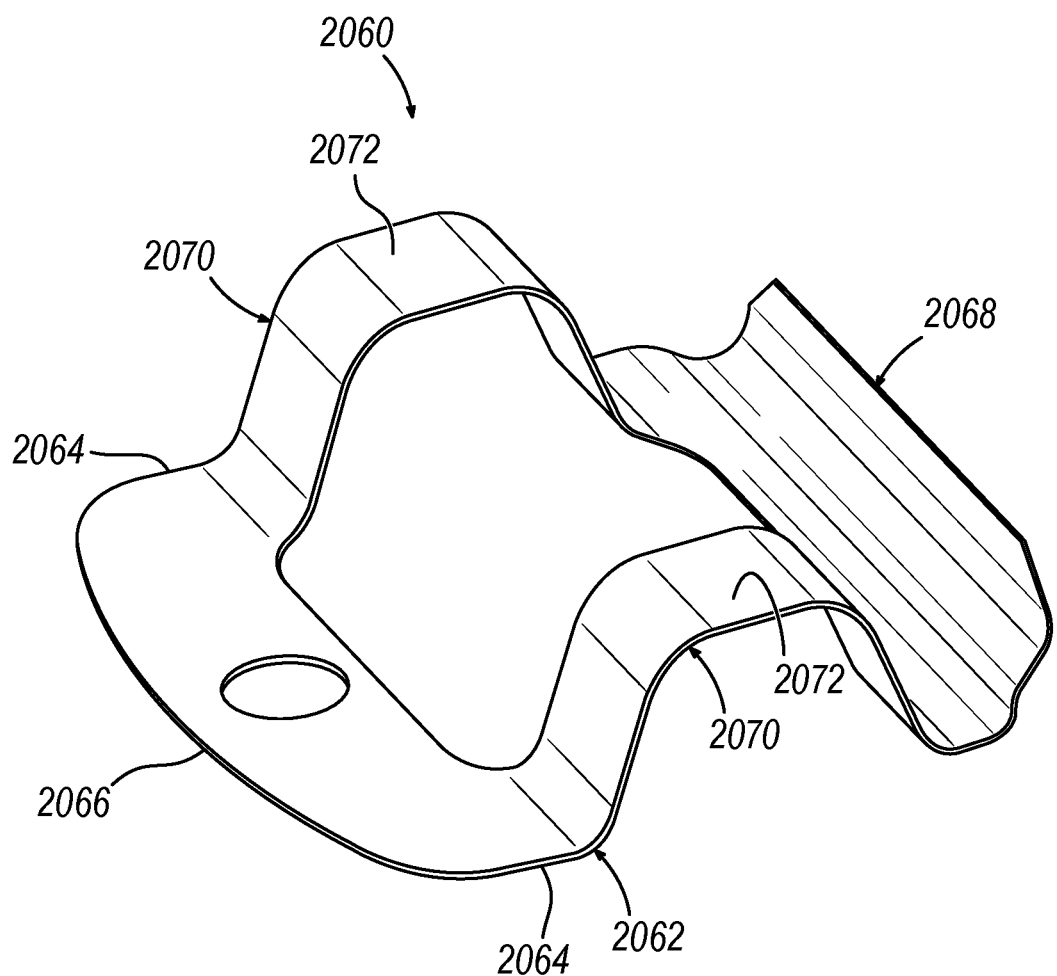
FIG. 64 depicts a schematic perspective of another exemplary spring plate configured for use with the anvil of FIG. 53.

FIG. 64 shows another exemplary spring plate (2060) that includes a base plate portion (2062) having a pair of side tabs (2064) and a rounded proximal end portion (2066), and a distal hinge lip (2068). Similar to spring plate (2040), each side tab (2064) of spring plate (2060) includes a resilient pleat (2070) of increased height relative to pleats (2034) of spring plate (2020). Each pleat (2070) further includes a flat top surface (2072). A proximal spring arm is omitted from spring plate (2060), and tapered proximal protrusion (1930) of anvil tip (1920) is instead configured to frictionally engage one or more inner surfaces of connection member (1940) to assume the first and second discrete positions, for example similar to the configuration described above in connection with anvil (1818).

Figure 65:
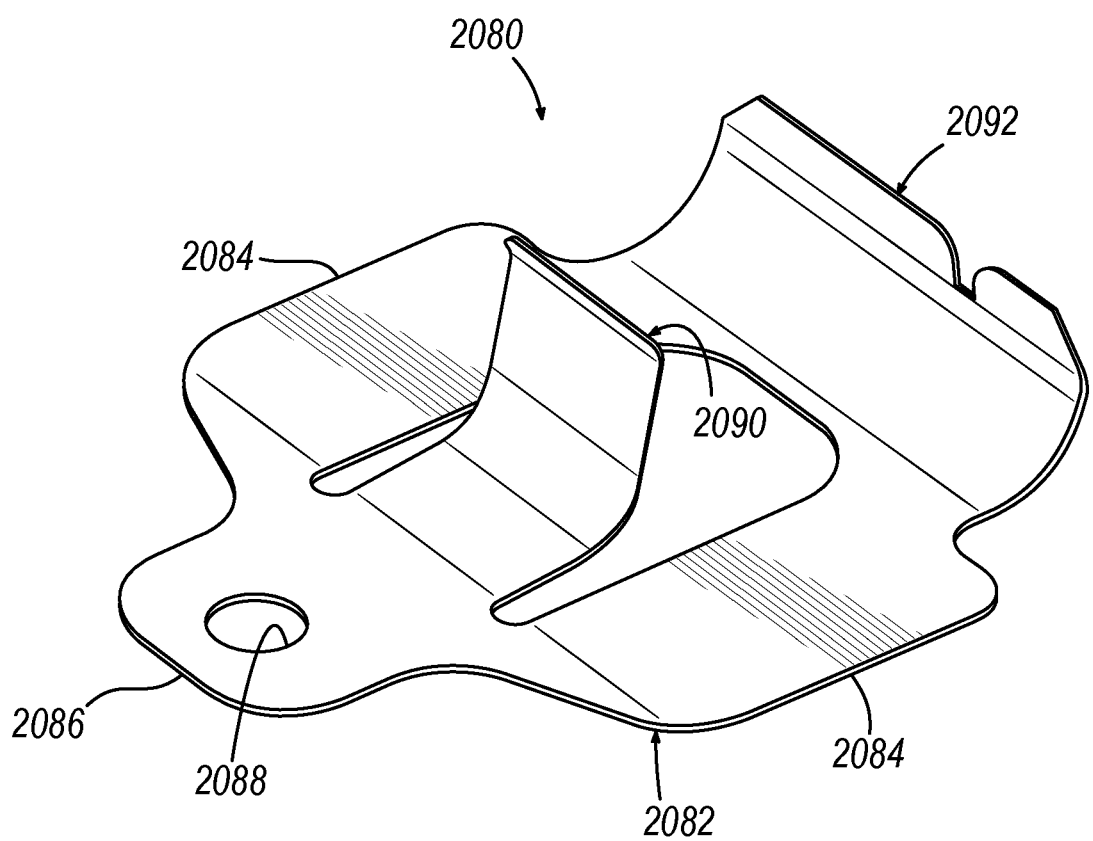
FIG. 65 depicts a schematic perspective of another exemplary spring plate configured for use with the anvil of FIG. 53.
Figure 66:
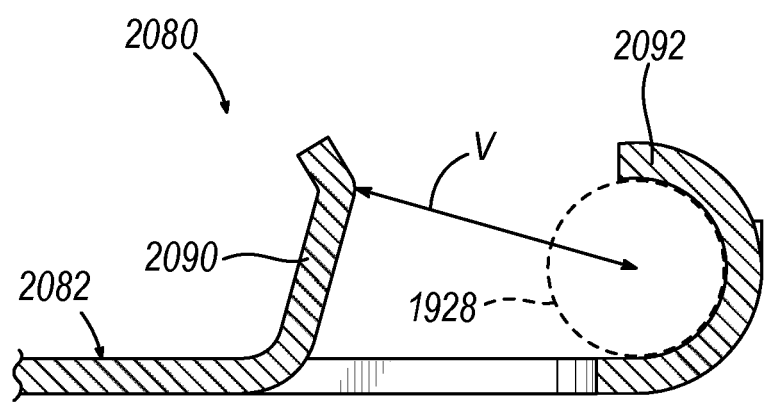
FIG. 66 depicts a schematic side view of the spring plate of FIG. 65, showing a resultant force vector that represents a force exerted by the distal tip of FIG. 53 on a proximal spring arm of the spring plate in combination with a reactive force exerted by the proximal spring arm on the distal tip.

FIG. 65 shows another exemplary spring plate (2080) that includes a base plate portion (2082) having a pair of side tabs (2084) and a proximal tab (2086) with an opening (2088), a proximal spring arm (2090), and a distal hinge lip (2092). In this version, base plate portion (2080) has been elongated relative to base plate portion (1972) of spring plate (1970). As shown in the schematic depiction of FIG. 66, this elongation of base plate portion (2082) spaces distal hinge lip (2092) at a greater distal distance from spring arm (2090). This configuration enables distal hinge lip (2092) to slightly flex upwardly relative to the proximal end of base plate portion (2082) and spring arm (2090). As a result, spring arm (2090) and tapered protrusion (1930) of anvil tip (1920) exert mutual forces on one another during tip position transition along a vector (V) that is more parallel to base plate portion (2082) and the longitudinal axis of anvil body (1910) as compared to a corresponding relationship for spring plate (1970). Such a configuration may promote more favorable stress distributions within spring arm (2090).

4. Exemplary Additional Features for Toggling Tip

Figure 67:
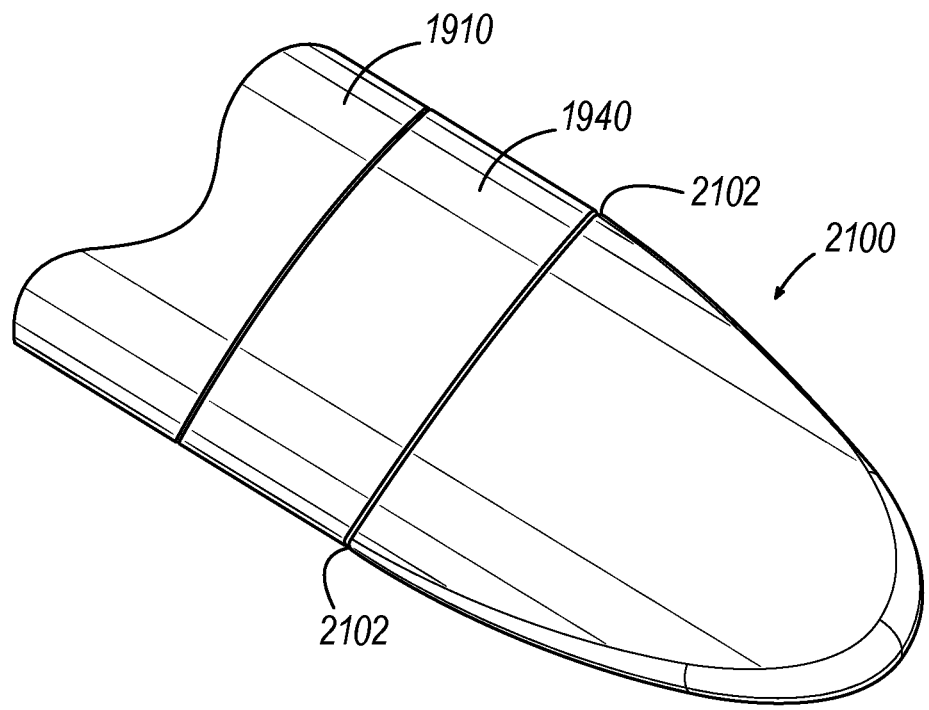
FIG. 67 depicts a perspective view of another exemplary distal tip configured to pivotably toggle relative to an anvil body.

In some instances, it may be desirable to provide anvil tip (1920) with exemplary alternative features that improve various aspects of use during a surgical procedure. FIG. 67 shows anvil body (1910) and connection member (1940) fitted with an exemplary alternative distal tip (2100). Anvil tip (2100) is similar to anvil tip (1920) described above except that that anvil tip (2100) has proximal corners (2102) that are positioned in close proximity to and directly confront the distal face of connection member (1940). This configuration thus minimizes the size of a longitudinal gap between the proximal end of anvil tip (2100) and the distal end of connection member (1940).

Advantageously, this gap minimization reduces risk of snagging tissue within the gap during toggling of anvil tip (2100) relative to connection member (1940), which might otherwise cause undesirable trauma due the tissue during a surgical procedure.

Figure 68:
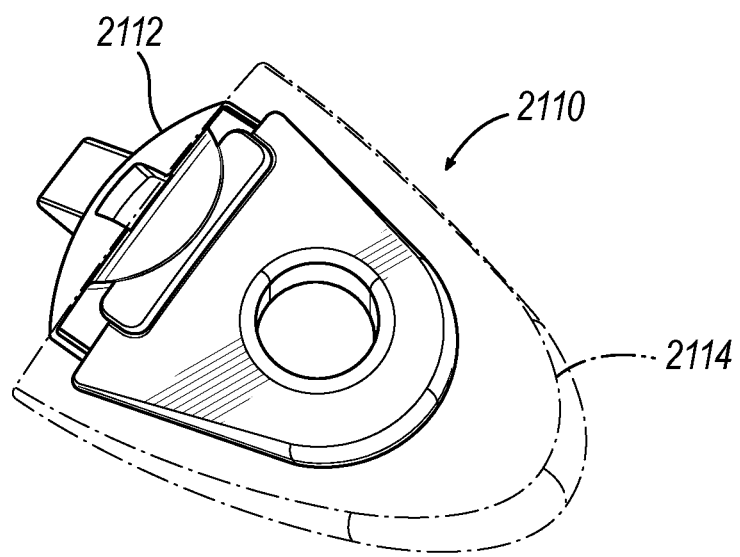
FIG. 68 depicts a perspective view of another exemplary distal tip configured to pivotably toggle relative to an anvil body.

FIG. 68 shows another exemplary alternative anvil tip (2110) configured for use with anvil (1900) in place of anvil tip (1920). Anvil tip (2110) is similar to anvil tip (1920) except that anvil tip (2110) includes an inner core member (2112) and a polymeric jacket (2114) overmolded over inner core member (2112) to define the same general shape as anvil tip (1920). Polymeric jacket (2114) may be formed of silicone, for example, and may provide tip (2100) with enhanced flexibility and a resulting more-atraumatic construction relative to anvil tip (1920).

5. Toggling Tip Unit with Integrated Living Hiving

Figure 69:
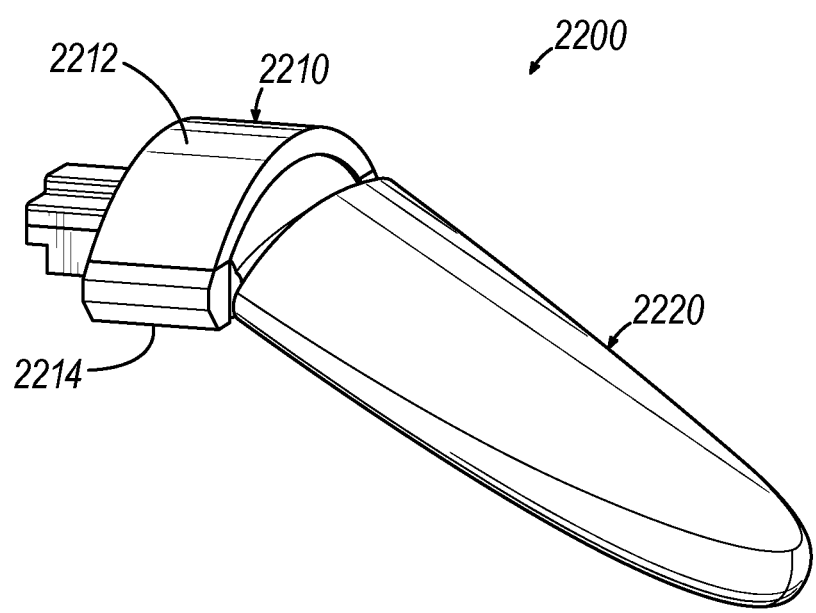
FIG. 69 depicts a perspective view of an exemplary distal tip unit configured to couple to the distal end of an anvil body, showing the distal tip unit in an assembled state.

In some instances, it may be desirable to form anvil tip (1920) and connection member (1940) as a single integral component, attachable to anvil body (1910), while still enabling anvil tip (1920) to pivot relative to connection member (1940) between first and second discrete positions. FIGS. 69-70B show an exemplary toggling tip unit (2200) that exhibits such a construction. In particular, tip unit (2200) includes a proximal connection portion (2210) and a distal tip portion (2220) that is configured to pivot relative to proximal connection portion (2210) via a living hinge (2202) formed integrally therebetween.

Figure 70A:
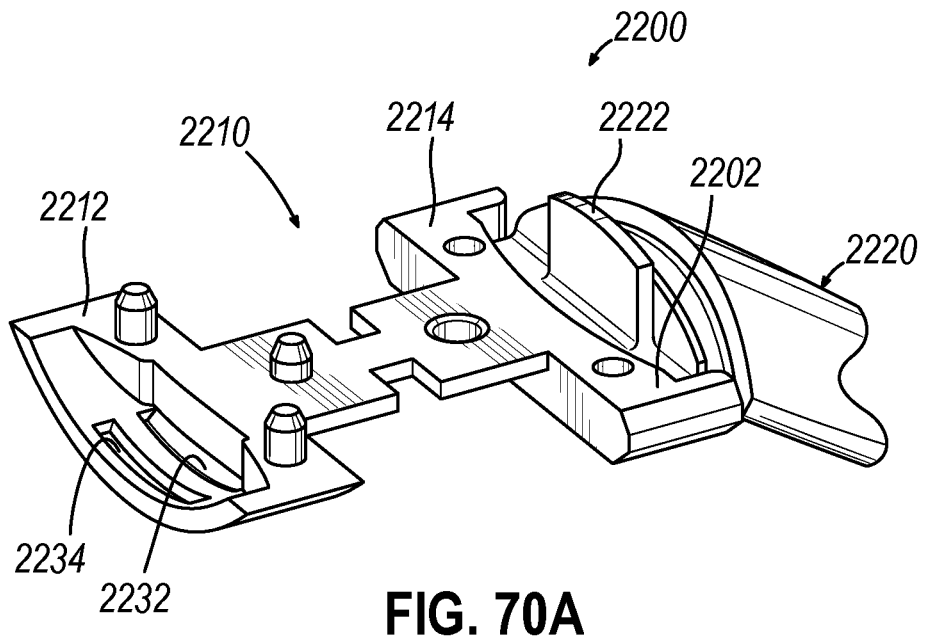
FIG. 70A depicts a perspective view of the distal tip unit of FIG. 69 in a pre-assembled state, showing an integrated living hinge of the distal tip unit.
Figure 70B:
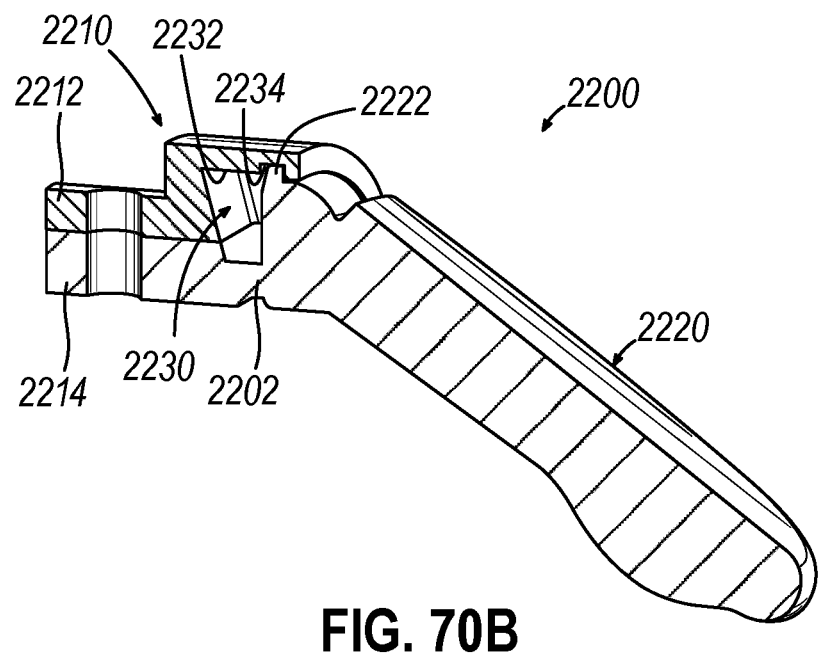
FIG. 70B depicts a side sectional view of the distal tip of FIG. 69 in the assembled state, also showing the integrated living hinge.

FIG. 70A shows tip unit (2200) in a pre-assembled state in which a first segment (2212) of connection portion (2210) resides in the same plane as a second segment (2214) of connection portion (2210) with which first segment (2212) is hingedly coupled. As shown in FIGS. 70A-70B, first segment (2212) is flipped over the hinge coupling to mate with a top side of second segment (2214), thereby capturing an upward protrusion (2222) formed at a proximal end of tip portion (2220) in an interior space in the form of a cavity (2230) formed between the first and second connection portion segments (2212, 2214). Tip portion (2220) is then selectively pivotable relative to connection portion (2210) about living hinge (2202) between first and second discrete positions. In particular, a top wall of cavity (2230) defined by first segment (2212) includes a proximal detent recess (2232) and a distal detent recess (2234) configured to releasably capture upward protrusion (2222) of tip portion (2220) therein. Positioning upward protrusion (2222) within proximal detent recess (2232) provides tip portion (2220) in a straight configuration relative to connection portion (2210). Positioning upward protrusion (2222) within distal detent recess (2232) provides tip portion (2220) in a downwardly angled position, as shown in FIGS. 69 and 70B.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument end effector, comprising: A surgical instrument end effector, comprising: (a) a first jaw configured to receive a staple cartridge; (b) a second jaw comprising an anvil having a plurality of staple forming pockets, wherein the first and second jaws are operable to clamp and staple tissue positioned therebetween; and (c) a tip member movably disposed at a distal end of the anvil, wherein the tip member is configured to toggle relative to the anvil between a first discrete position and a second discrete position, wherein the tip member in the first discrete position is oriented angularly toward the first jaw, wherein the tip member in the second discrete position is oriented angularly away from the first discrete position.

Example 2

The surgical instrument end effector of Example 1, wherein the anvil defines a longitudinal axis, wherein the tip member is configured to extend parallel with the longitudinal axis in the second discrete position.

Example 3

The surgical instrument end effector of any of the preceding Examples, wherein the tip member is movable relative to the anvil about a transverse axis between the first and second discrete positions.

Example 4

The surgical instrument end effector of any of the preceding Examples, wherein the tip member is configured to maintain each of the first and second discrete positions independently of an external input force.

Example 5

The surgical instrument end effector of any of the preceding Examples, wherein a proximal end of the tip member includes a tapered protrusion, wherein the tapered protrusion is movable relative to the anvil between the first and second discrete positions.

Example 6

The surgical instrument end effector of any of the preceding Examples, further comprising a resilient member configured to bias the tip member toward each of the first and second discrete positions.

Example 7

The surgical instrument end effector of Example 6, wherein the resilient member is configured to constrain the tip member longitudinally relative to the anvil while permitting the tip member to move relative to the anvil between the first and second discrete positions.

Example 8

The surgical instrument end effector of any of Examples 6 through 7, wherein the tip member is pivotably coupled with a distal end of the resilient member, wherein the tip member is pivotable relative to the resilient member between the first and second discrete positions.

Example 9

The surgical instrument end effector of any of Examples 6 through 8, wherein the tip member includes a cavity, wherein a distal end of the resilient member is received within the cavity.

Example 10

The surgical instrument end effector of any of Examples 6 through 9, wherein the resilient member includes a spring arm, wherein a proximal end of the tip member is configured to engage a first portion of the spring arm in the first discrete position and a second portion of the spring arm in the second discrete position.

Example 11

The surgical instrument end effector of any of Examples 6 through 10, wherein a proximal end of the resilient member is longitudinally fixed relative to the anvil.

Example 12

The surgical instrument end effector of any of Examples 6 through 11, further comprising a connection member that couples the tip member with the anvil body, wherein the resilient member is at least partially housed within the connection member.

Example 13

The surgical instrument end effector of Example 12, wherein the connection member includes an inner channel, wherein a proximal end of the tip member is movably received within the inner channel.

Example 14

The surgical instrument end effector of any of the preceding Examples, further comprising a connection member that couples the tip member with the anvil body, wherein the connection member includes an inner channel that movably receives a proximal end of the tip member therein.

Example 15

A surgical instrument, comprising: (a) a body; (b) a shaft extending distally from the body; and (c) the end effector of any of the preceding Examples, wherein the end effector is disposed at a distal end of the shaft.

Example 16

A surgical instrument end effector, comprising: (a) a first jaw configured to receive a staple cartridge; (b) a second jaw comprising an anvil having a plurality of staple forming pockets, wherein the first and second jaws are operable to clamp and staple tissue positioned therebetween; and (c) a tip member movably disposed at a distal end of the anvil, wherein the tip member is movable relative to the anvil about a transverse axis between a first discrete position and a second discrete position, wherein the tip member in the first discrete position is configured to maintain the first discrete position until acted upon by an external input force, wherein the tip member in the second discrete position is configured to maintain the second discrete position until acted upon by an external input force.

Example 17

The surgical instrument end effector of Example 16, wherein a proximal end of the tip member includes a protrusion, wherein the protrusion is movable relative to the anvil between the first and second discrete positions.

Example 18

The surgical instrument end effector of any of Examples 16 through 17, further comprising a resilient member configured to bias the tip member toward each of the first discrete position and the second discrete position.

Example 19

An anvil configured for use with a surgical instrument end effector, comprising:
(a) an anvil body; (b) a plurality of staple forming pockets provided on the anvil body; (c) a tip member movably coupled with a distal end of the anvil body, wherein the tip member is movable relative to the anvil body between a first discrete position and a second discrete position; and (d) a resilient member, wherein the resilient member is configured to releasably maintain the tip member in the first discrete position when the tip member is in the first discrete position and in the second discrete position when the tip member is in the second discrete position.

Example 20

The anvil of Example 19, wherein the resilient member is configured to at least partially constrain the tip member longitudinally relative to the anvil body while permitting the tip member to pivot relative to the anvil body.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 16/729,559, entitled "Surgical Stapler with Deflectable Distal Tip," filed on Dec. 30, 2019, issued as U.S. Pat. No. 11,304,697 on Apr. 19, 2022; and/or U.S. patent application Ser. No. 16/729,557, entitled "Surgical Stapler with Rotatable Distal Tip," filed on Dec. 30, 2019, issued as U.S. Pat. No. 11,317,912 on May 3, 2022. The disclosure of each of these U.S. patent applications is incorporated by reference herein.

It should also be understood that the teachings herein may be readily combined with various teachings in U.S. Pat. No. D836,198, entitled "Surgical Stapler End Effector with Varying Deck Height and Tissue Gripping Features," issued Dec. 18, 2018; U.S. Pat. No. D833,010, entitled "Circular Surgical Stapler End Effector with Varying Deck Height and Tissue Gripping Features," issued Nov. 6, 2018; U.S. Pat. Pub. No. 2018/0235610, entitled "Surgical Stapler with Insertable Distal Anvil Tip," published Aug. 23, 2018, issued as U.S. Pat. No. 10,729,434 on Aug. 4, 2020; U.S. Pat. Pub. No. 2018/0235611, entitled "Surgical Stapler with Cooperating Distal Tip Features on Anvil and Staple Cartridge," published Aug. 23, 2018, issued as U.S. Pat. No. 10,806,451 on Oct. 20, 2020; U.S. Pat. No. D836,199, entitled "Surgical Stapler with Bent Anvil Tip and Angled Staple Cartridge Tip," issued Dec. 18, 2018; U.S. Pat. Pub. No. 2018/0235619, entitled "Surgical Stapler with Bent Anvil Tip, Angled Staple Cartridge Tip, and Tissue Gripping Features," published Aug. 23, 2018, issued as U.S. Pat. No. 10,758,231 on Sep. 1, 2020; U.S. Pat. Pub. No. 2019/0000481, entitled "Method of Surgical Stapling with End Effector Component Having a Curved Tip," published Jan. 3, 2019; U.S. patent application Ser. No. 16/235,617, entitled "Method of Applying Buttresses to Surgically Cut and Stapled Sites," filed Dec. 28, 2018, issued as U.S. Pat. No. 11,033,269 on Jun. 15, 2021; U.S. patent application Ser. No. 16/035,872, entitled "Permanent Attachment Means for Curved Tip of Component of Surgical Stapling Instrument," filed Jul. 16, 2018, issued as U.S. Pat. No. 10,973,515 on Apr. 13, 2021; U.S. patent application Ser. No. 16/035,803, entitled "Surgical Stapling End Effector Component with Deformable Tip Having Void," filed Jul. 16, 2018, issued as U.S. Pat. No. 10,786,252 on Sep. 29, 2020; U.S. patent application Ser. No. 16/035,821, entitled "Surgical Stapling End Effector Component with Deformable Tip Skewing in Multiple Planes," filed Jul. 16, 2018, issued as U.S. Pat. No. 11,179,154 on Nov. 23, 2021; U.S. patent application Ser. No. 16/035,825, entitled "Surgical Stapling End Effector Component with Articulation and Asymmetric Deformable Tip," filed Jul. 16, 2018, issued as U.S. Pat. No. 11,160,550 on Nov. 2, 2021; U.S. patent application Ser. No. 16/035,831, entitled "Permanent Attachment Means for Curved Tip of Component of Surgical Stapling Instrument," filed Jul. 16, 2018, issued as U.S. Pat. No. 10,912,558 on Feb. 9, 2021; U.S. patent application Ser. No. 16/035,834, entitled "Buttress Applier Cartridge for Surgical Stapler Having End Effector with Deflectable Curved Tip," filed Jul. 16, 2018, issued as U.S. Pat. No. 10,912,561 on Feb. 9, 2021. Various suitable ways in which the teachings herein may be combined with the teachings of the above U.S. patents, U.S. Patent Publications, and U.S. patent applications will be apparent to those of ordinary skill in the art. The disclosure of each of the above-cited U.S. Patents, U.S. patent Publications, and U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument end effector, comprising:
   (a) a first jaw configured to receive a staple cartridge;
   (b) a second jaw comprising an anvil body having a plurality of staple forming pockets, wherein the first and second jaws are operable to clamp and staple tissue positioned therebetween; and
   (c) a tip member movably disposed distal to a distal end of the anvil body, wherein the tip member is configured to pivotably toggle relative to the anvil body about a transverse axis between a first discrete position and a second discrete position such that a proximal end of the tip member is movable relative to the distal end of the anvil body while the tip member remains longitudinally constrained relative to the anvil body,
   wherein the tip member in the first discrete position is oriented angularly toward the first jaw,
   wherein the tip member in the second discrete position is oriented away from the first discrete position.

2. The surgical instrument end effector of claim 1, wherein the anvil body defines a longitudinal axis, wherein the tip member is configured to extend parallel with the longitudinal axis in the second discrete position.

3. The surgical instrument end effector of claim 1, wherein the tip member is configured to maintain each of the first and second discrete positions independently of an external input force.

4. The surgical instrument end effector of claim 1, wherein the proximal end of the tip member includes a tapered protrusion, wherein the tapered protrusion is movable relative to the anvil body between the first and second discrete positions.

5. The surgical instrument end effector of claim 1, further comprising a resilient member configured to exert a bias force on the tip member and thereby bias the tip member toward each of the first and second discrete positions.

6. The surgical instrument end effector of claim 5, wherein the resilient member is configured to constrain the tip member longitudinally relative to the anvil body while permitting the tip member to move relative to the anvil body between the first and second discrete positions.

7. The surgical instrument end effector of claim 5, wherein the tip member is pivotably coupled with a distal end of the resilient member, wherein the tip member is pivotable relative to the resilient member between the first and second discrete positions.

8. The surgical instrument end effector of claim 5, wherein the tip member includes a cavity, wherein a distal end of the resilient member is received within the cavity.

9. The surgical instrument end effector of claim 5, wherein the resilient member includes a spring arm, wherein the proximal end of the tip member is configured to engage a first portion of the spring arm in the first discrete position and a second portion of the spring arm in the second discrete position.

10. The surgical instrument end effector of claim 5, wherein a proximal end of the resilient member is longitudinally fixed relative to the anvil body.

11. The surgical instrument end effector of claim 5, further comprising a connection member that couples the tip member with the anvil body, wherein the resilient member is at least partially housed within the connection member, wherein the connection member includes an inner channel that movably receives the proximal end of the tip member.

12. A surgical instrument, comprising:
    (a) a body;
    (b) a shaft extending distally from the body; and
    (c) the end effector of claim 1, wherein the end effector is disposed at a distal end of the shaft.

13. The surgical instrument of claim 1, wherein the proximal end of the tip member is movable within an inner channel of the surgical instrument end effector as the tip member transitions between the first and second discrete positions.

14. A surgical instrument end effector, comprising:
    (a) a first jaw configured to receive a staple cartridge;
    (b) a second jaw comprising an anvil body having a plurality of staple forming pockets, wherein the first and second jaws are operable to clamp and staple tissue positioned therebetween;

(c) a structure located distal to the plurality of staple forming pockets and defining an interior space; and (d) a tip member pivotably disposed distal to the anvil body, wherein the tip member is pivotable relative to the anvil body about a transverse axis between a first discrete position and a second discrete position such that a proximal end of the tip member is movable within the interior space, wherein the tip member in the first discrete position is configured to maintain the first discrete position until acted upon by an external input force, wherein the tip member in the second discrete position is configured to maintain the second discrete position until acted upon by an external input force.

15. The surgical instrument end effector of claim 14, wherein a proximal end of the tip member includes a protrusion, wherein the protrusion is movable within the interior space and relative to the anvil body between the first and second discrete positions.

16. The surgical instrument end effector of claim 14, further comprising a resilient member configured to bias the tip member toward each of the first discrete position and the second discrete position.

17. The surgical instrument end effector of claim 14, wherein the structure comprises a connection member that couples the tip member with the anvil body, wherein the connection member defines the interior space.

18. An anvil configured for use with a surgical instrument end effector, comprising:

(a) an anvil body;

(b) a plurality of staple forming pockets provided on the anvil body;

(c) a tip member movably coupled with a distal end of the anvil body, wherein the tip member is movable relative to the anvil body between a first discrete position and a second discrete position; and (d) a resilient member separate from and configured to exert a bias force on the tip member, wherein the resilient member is configured to releasably maintain the tip member in the first discrete position when the tip member is in the first discrete position and in the second discrete position when the tip member is in the second discrete position.

19. The anvil of claim 18, wherein the resilient member is configured to at least partially constrain the tip member longitudinally relative to the anvil body while permitting the tip member to pivot relative to the anvil body.

20. The anvil of claim 19, wherein a proximal end of the tip member is movable relative to the anvil body as the tip member transitions between the first discrete position and the second discrete position.

* * * * *